United States Patent
Nicolaou et al.

(10) Patent No.: US 6,531,497 B1
(45) Date of Patent: Mar. 11, 2003

(54) EPOTHILONE DERIVATIVES AND THEIR SYNTHESIS AND USE

(75) Inventors: Kyriacos Costa Nicolaou, La Jolla, CA (US); Nigel Paul King, Hitchin (GB); Maruice Raymond Verschoyle Finlay, Macclesfield (GB); Yun He, Carlsbad, CA (US); Frank Roschangar, Chapel Hill, NC (US); Dionisios Vourloumis, San Diego, CA (US); Hans Vallberg, Huddinge (SE); Antony Bigot, Paris (FR)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/720,070
(22) PCT Filed: Jun. 21, 1999
(86) PCT No.: PCT/EP99/04287
§ 371 (c)(1), (2), (4) Date: Apr. 19, 2001
(87) PCT Pub. No.: WO99/67252
PCT Pub. Date: Dec. 29, 1999

(51) Int. Cl.[7] .................. A61K 31/425; A61K 31/415; C07D 277/04; C07D 277/18
(52) U.S. Cl. .............. 514/370; 514/390; 548/182; 548/186; 548/184; 548/193
(58) Field of Search ............... 548/203, 182, 548/184, 186, 193; 514/365, 369, 370

(56) References Cited

FOREIGN PATENT DOCUMENTS

| DE | 41 38 042 | 5/1993 |
|---|---|---|
| WO | WO93/10121 | 5/1993 |
| WO | 9310121 | 5/1993 |
| WO | 9719086 | 5/1997 |
| WO | 9808849 | 3/1998 |
| WO | 9822461 | 5/1998 |
| WO | 982929 | 6/1998 |
| WO | 9825929 | 6/1998 |
| WO | WO 9825929 * | 6/1998 |
| WO | 9838192 | 9/1998 |
| WO | 9901124 | 1/1999 |
| WO | 9902514 | 1/1999 |
| WO | 9907692 | 2/1999 |
| WO | 99077692 | 2/1999 |

OTHER PUBLICATIONS

Nicolaou, et al., "Total Synthesis of 26–Hydroxy–Epothilone B and Related Analogs via a Macrolactonization Based Strategy", *Tetrahdron 54:* 7127–7166 (1998).

May, et al., "Total Synthesis of (–)–epothilone B", *Chem. Commun.*: 1597–1598 (1998).

Nicolaou, et al., "Total Synthesis of 26–hydroxyepothilone B and Related Analogues", *Chem. Commun.*: 2343–2344 (1997).

Su, et al., "Structure–Activity Relationships of the Epothilones and the First in vivo Comparison with Paclitaxel", *Angew. Chem. Int. Ed. Engl 36:* 2093–2096 (1997).

Meng, et al., "Total Syntheses of Epothilones A and B", *J. Amer. Chem. Soc. 119:* 10073–10092 (1997).

Nicolaou, et al., "Synthesis of Epotnilones A and B in Solid and Solution Phase", *Nature 387:* 268–272 (1997).

Nicolaou, et al., "Total Syntheses of Epothilones A and B via a Macrolactonization–Based Strategy", *J. Amer. Chem. Soc. 119:* 7974–7991 (1997).

Balog, et al., "Stereoselective Syntheses and Evaluation of Compounds in the 8–Desmethylepothilone A Series: Some Surprising Observations Regarding their Chemical and Biological Properties", *Tetr. Lett. 38:* 4529–4532 (1997).

Schiff, et al., "Promotion of Microtubule Assembly in vitro by Taxols", *Nature 277:* 665–667 (1979).

Balog, et al., "Total Synthesis of (–)-Epothilone A", *Ang. Chem. Int. Ed. Engl.35 (23/24):* 2801–2803 (1996).

Hofle, et al., "Epothilone A and B–Novel 16–Membered Macrolides with Cytotoxic Activity: Isolation, Crystal Structure, and Conformation in Solution", *Ang. Chem. Int. Ed. Engl. 35 (13/14):* 1567–1568 (1996).

Nicolaou, et al., "An Approach to Epothilones Based on Olefin Metathesis", *Ang. Chem. Int. Ed. Engl. 35 (20):* 2399–2401 (1996).

(List continued on next page.)

Primary Examiner—Alan L. Rotman
Assistant Examiner—Binta Robinson
(74) Attorney, Agent, or Firm—Donald G. Lewis

(57) ABSTRACT

The invention relates to epothilone analog represented by formula (I) wherein (i) $R_2$ is absent or oxygen; "a" can be either a single or double bond; "b" can be either absent or a single bond; and "c" can be either absent or a single bond, with the proviso that if $R_2$ is oxygen then "b" and "c" are both a single bond and "a" is a single bond; if $R_2$ is absent then "b" and "c" are absent and "a" is a double bond; and if "a" is a double bond, then $R_2$, "b" and "c" are absent; $R_3$ is a radical selected from the group consisting of hydrogen; lower alkyl; —CH=CH$_2$; —C≡CH; —CH$_2$F; —CH$_2$Cl; —CH$_2$—OH; —CH$_2$—O—(C$_1$–C$_6$-alkyl); and —CH$_2$—S—(C$_1$–C$_6$-alkyl); $R_4$ and $R_5$ are independently selected from hydrogen, methyl or a protecting group; and $R_1$ is as defined in the specification, or a salt of a compound of formula (I) where a salt-forming group is present. A further aspect of the invention is related to the synthesis of epothilone E. These compounds have inter alia microtubuli depolymerization inhibiting activity and are e.g. useful against proliferative diseases (I)

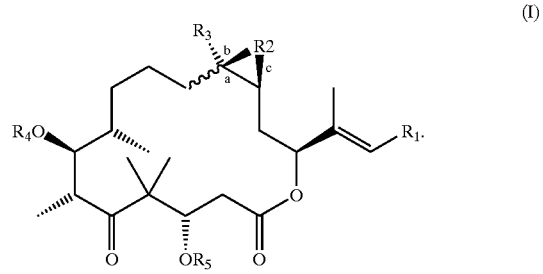

17 Claims, No Drawings

OTHER PUBLICATIONS

Nicolaou, et al., "Total Synthesis of Epothilone A: The Macrolactonization Approach", *Ang. Chem. Int. Ed. Engl.* 36 (5): 525–527 (1997).

Nicolaou, et al., "Chemistry and Biology of Taxol", *Ang. Chem. Int. Ed. Engl.* 33: 15–44 (1994).

Winkler, et al., "A Model for the Taxol (Paclitaxel)/Epothilone Pharmacophore", *Bioorg. Med. Chem. Int. Ed. Engl.* 33: 2963–2966 (1996).

Nicolaou, et al., "Designed Epothilones: Combinatorial Synthesis, Tubulin Assembly Properties, and Cytotoxic Action against Taxol–Resistant Tumor Cells", *Ang. Chem. Int. Ed. Engl.* 36 (19): 2097–2103 (1997).

Nicolaou, et al., "The Olefin Metathesis Approach to Epothilone A and its Analogues", *J. Amer. Chem. Soc.* 119: 7960–7973 (1997).

Schinzer, et al., "Total Synthesis of (–)-Epothilone A", *Ang. Chem. Int. Ed.. Engl.* 36(5): 523–524 (1997).

Yang, et al., "Total Synthesis of Epothilone A: The Olefin Metathesis Approach", *Ang. Chem. Int. Ed. Engl.* 36: 166–168 (1997).

Bollag, et al., "Epothilones, a New Class of Microtubule–stabilizing Agents with a Taxol–like Mechanism of Action", *Cancer Res.* 55: 2325–2333 (1995).

Meng, et al., "Remote Effects of Macrolide Formation through Ring–Forming Olefin Metathesis: An Application to the Synthesis of Fully Active Epothilone Congeners", *Amer. Chem. Soc.* 119: 2733–2734 (1997).

Grever, et al., "The National Cancer Institute: Cancer Drug Discovery and Development Program", *Seminars Oncol.* 19: 622–638 (1992).

Mulzer, et al., "Synthesis of the C(1)–C(9) Segment of the Cytotoxic Macrolides Epothilon A and B", *Tetr. Lett.* 37(51): 9179–9182 (1996).

Claus, et al., "Synthesis of the C1–C9 Segment of Epothilons", *Tetr. Lett.* 38(8): 1359–1362 (1997).

Gabriel, et al., "The Chromium–Reformatsky Reaction: Asymmetric Synthesis of the Aldol Fragment of the Cytotoxic Epothilons from 3–(2–Bromoacyl)–2–oxazolidinones", *Tetr. Lett.* 38(8): 1363–1366 (1997).

Meng, et al., "Studies toward a Synthesis of Epothilone A: Use of Hydropyran Templates for the Management of Acyclic Stereochemical Relationships", *Org. Chem.* 61: 7998–7999 (1996).

Bertinato, et al., "Studies toward a Synthesis of Epothilone A: Stereocontrolled Assembly of the Acyl Region and Models for Macrocyclization", *J. Org. Chem.* 61: 8000–8001 (1996).

Kowalski, et al., "Activities of the Microtubule–stabilizing Agents Epothilones A and B with Purified Tubulin and in Cells Resistant to Paclitaxel (Taxol)", *J. Biol. Chem.* 272: 2534–2541 (1997).

Schinzer, et al., "Total Synthesis of (–) Epothilone A", *Angew. Chem. Int. Ed. Engl.,* 36:523–524 (1997).

Yang, et al., "Total Synthesis of Epothilone A: The Olefin Metathesis Approach", *Angew. Chem. Int. Ed. Engl.,* 36:166–168 (1997).

Bolag, et al., "Epothilones, a New Class of Microtubule–stabilizing Agents with a Taxol–like Mechanism of Action", *Cancer Research,* 55:2325–2333 (1995).

Meng, et al., "Remote Effects in Macrolide Formation through Ring–Forming Olefin Metathesis: . . . ", *J. Am. Chem. Soc.,* 119:2733–2734 (1997).

Grever, et al., "The National Cancer Institute: Cancer Drug Discovery and Development Program", *Seminars in Oncology,* 19:622–638 (1992).

Mulzer, et al., "Synthesis of the C(1)–C(9) Segment of the Cytotoxic Macrolides Epothilon A and B", *Tetrahedron Letters,* 37:9179–9182 (1996).

Claus, et al, "Synthesis of the C1–C9 Segment of Epothilons", *Tetrahedron Letters,* 38:1359–1362 (1997).

Gabriel, et al, "The Chromium–Reformatsky Reaction: Asymmetric Synthesis . . . " *Tetrahedron Letters,* 38:1363–1366 (1997).

Meng, et al., "Studies toward a Synthesis of Epothilone A: Use of Hydropyran Templates . . . ", *J. Org. Chem.,* 61:7998–7999 (1996).

Bertinato, et al, "Studies toward a Synthesis of Epothilon A: Stereo–controlled Assembly . . . ", *J. Org. Chem.,* 61:8000–8001 (1996).

Kowalski, et al., "Activities of the Microtubule–stabilizing Agents Epothilones A and B . . . ", *Journ. Biol. Chem.,* 272:2534–2541 (1997).

Schiff, et al., "Promotion of Microtubule Assembly in vitro by Taxol", *Nature,* 277:665–667 (1979).

Balog, et al., "Total Synthesis of (–)-Epothilone A", *Angew. Chem. Int. Ed. Eng.,* 35:2801–2803 (1996).

Hofle, et al., "Epothilone A and B–Novel 16–Membered Macrolides with Cytotoxid Activity: . . . ", *Angew. Chem. Int. Ed. Engl.,* 35:1567–1569 (1996).

Nicolaou, et al., "An Approach to Epothilones Based on Olefin Metathesis", *Angew. Chem. Int. Ed. Engl.,* 35:2399–2401 (1996).

Nicolaou, et al., "Total Synthesis of Epothilone A: The Macrolactonization Approach", *Angew. Chem. Int. Ed. Engl.,* 36:525–527 (1997).

Nicolaou, et al., "Chemistry and Biology Taxol", *Angew. Chem. Int. Ed. Engl.,* 33:15–44 (1994).

Nicolaou, et al., "Chemical Biology of Epothilones", *Angew. Chem. Int. Ed. Engl.* 37: 2014–2045 (1998).

White, et al., "Improved Synthesis of Epothilone B Employing Alkylation of an Alkyne for Assembly of Subunits", *Org. Lett.* 1: 1431–1434 (1999).

Sinha, et al., "Sets of Aldolase Antibodies with Antipodal Reactivities. Formal Synthesis of Epothilone E by Large–Scale Antibody–Catalyzed Resolution of Thiazole Aldol", *Org. Lett.* 1: 1623–1626 (1999).

Sawada, et al., "Enantioselective Total Synthesis of Epothilone A Using Multifunctional Asymmetric Catalyses", *Angew. Chem. Int. Ed. Engl.* 39: 209–213 (2000).

Martin, et al., "How Stable are Epoxides? A Novel Synthesis of Epothilone B", *Angew. Chem. Int. Ed. Engl.* 39: 581–583 (2000).

Taylor, et al., "Towards the Synthesis of Epothilone A: Enantioselective Preparation of the Thiazole Sidechain and Macrocyclic Ring Closure", *Tet. Lett.* 38: 2061–2064 (1997).

Su, et al., "Total Synthesis of (–)-Epothilone B: An Extension of the Suzuki Coupling Method and Insights into Structure–Activity Relationships of the Epothilones", *Angew. Chem. Int. Ed. Engl.* 36: 757–759 (1997).

Schinzer, et al., "Studies Towards the Total Synthesis of Epothilones: Asymmetric Synthesis of the Key Fragments", *Chem. Eur. J.* 2: 1477–1482 (1996).

Nicolaou, et al., "Total Synthesis of Oxazole and Cyclopropane–Containing Epothilone A Analogues by the Olefin Metathesis Approach", *Chem. Eur. J. 3:* 1957–1970 (1997).

Nicolaou, et al., "Total Synthesis of Oxazole– and Cyclopropane–Containing Epothilone B Analogues by the Macrolactonization Approach", *Chem. Eur. J. 3:* 1971–1986 (1997).

Nicolaou, et al., "Probing the Ring Size of Epothilones: Total Synthesis of [14]–, [15]–, [17]–, and [18]Epothilones", *Angew. Chem. Int. Ed. Engl. 37:* 81–84 (1998).

Nicolaou, et al., "Total Synthesis of Epothilone E and Analogues with Modified Side Chains through the Stille Coupling Reaction", *Angew. Chem. Int. Ed. Engl. 37:* 84–87 (1998).

Nicolaou, et al., "Total Synthesis of Epothilone E and Related Side–Chain Modified Analogues via a Stille Coupling Based Strategy", *Bioorg. Med. Chem. 7:* 665–697 (1999).

* cited by examiner

EPOTHILONE DERIVATIVES AND THEIR SYNTHESIS AND USE

GOVERNMENT RIGHTS

This invention was made with government support under Grant Nos. CA 46446 and CA 78045 by the National Institutes of Health. The government has certain rights in the invention.

CROSS-REFERENCE

This application is a 371 of PCT/EP 99/04287 filed Jun. 21, 1999.

SUMMARY OF THE INVENTION

The present invention relates to epothilone analogs having side chain modifications and to methods for producing such compounds, their use in the therapy of diseases or for the manufacture of pharmaceutical preparations for the treatment of diseases, as well as to novel intermediates used in the synthesis of such analogs and new methods of synthesis.

BACKGROUND OF THE INVENTION

The epothilones (1–5) are natural substances which exhibit cytotoxicity even against paclitaxel-resistant tumor cells by promoting the polymerization of α- and β-tubulin subunits and stabilizing the resulting microtubule assemblies. Epothilones displace paclitaxel (the active principle of TAXOL™) from its microtubuli binding site and are reported to be more potent than paclitaxel with respect to the stabilization of microtubules.

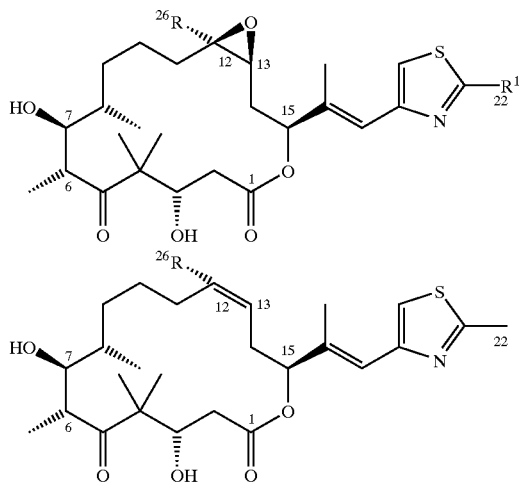

1: R = H, $R^1$ = Me: epothilone A
2: R = Me, $R^1$ = Me: epothilone B
3: R = H, $R^1$ = $CH_2OH$: epothilone E
4: R = H: epothilone C
5: R = Me: epothilone D What is needed are analogs of epothilone A and B that exhibit superior pharmacological properties, especially one or more of the following properties: an enhanced therapeutic index (e.g. a larger range of cytotoxic doses against e.g. proliferative diseases without toxicity to normal cells), better pharmakokinetic properties, better pharmacodynamic properties, better solubility in water, better efficiency against tumor types that are or become resistant to treatment with one or more other chemotherapeutics, better properties to facilitate manufacture of formulations, e.g. better solubility in polar solvents, especially those comprising water, enhanced stability, convenient manufacture of the compounds as such, improved inhibition of proliferation at the cellular level, high levels of microtubule stabilizing effects, and/or specific pharmacologic profiles.

DETAILED DESCRIPTION OF THE INVENTION

The present invention relates to new compounds that surprisingly have one or more of the above-mentioned advantages.

One major aspect of the invention relates to an epothilone analog compound represented by the formula I

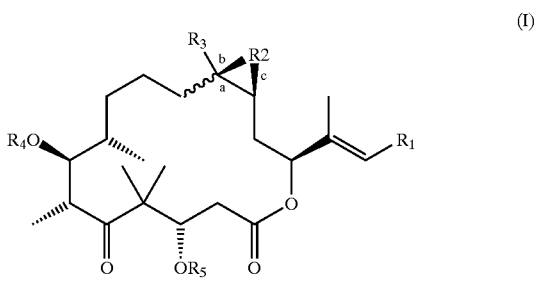

(I)

wherein the waved bond indicates that bond "a" is present either in the cis or in the trans form;

(i) $R_2$ is absent or oxygen; "a" can be either a single or double bond; "b" can be either absent or a single bond; and "c" can be either absent or a single bond, with the proviso that if $R_2$ is oxygen then "b" and "c" are both a single bond and "a" is a single bond; if $R_2$ is absent then "b" and "c" are absent and "a" is a double bond; and if "a" is a double bond, then $R_2$, "b" and "c" are absent;

$R_3$ is a radical selected from the group consisting of hydrogen; lower alkyl, especially methyl, ethyl, n-propyl, iso-propyl, n-butyl, iso-butyl, tert-butyl, n-pentyl, n-hexyl; —CH=$CH_2$; —C≡CH; —$CH_2$F; —$CH_2$Cl; —$CH_2$—OH; —$CH_2$—O—($C_1$–$C_6$-alkyl), especially —$CH_2$—O—$CH_3$; and —$CH_2$—S— ($C_1$–$C_6$-alkyl), especially —$CH_2$—S—$CH_3$;

$R_4$ and $R_5$ are independently selected from hydrogen, methyl or a protecting group, preferably hydrogen; and $R_1$ is a radical selected from the following structures:

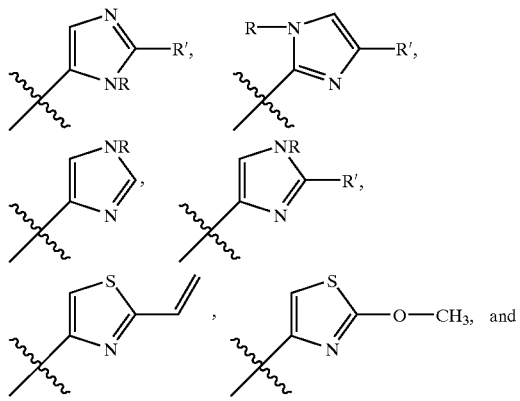

-continued

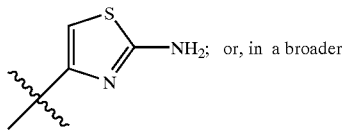
NH₂; or, in a broader aspect of the invention, of the formula

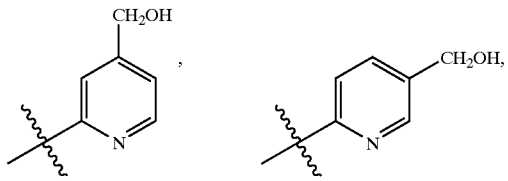

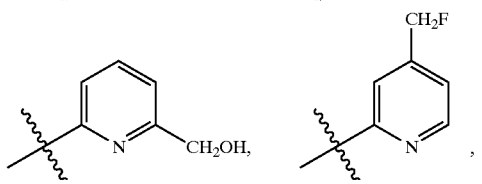

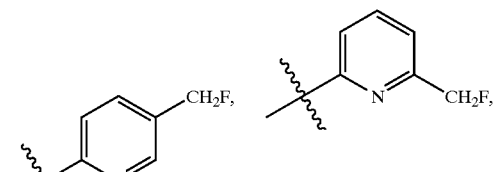

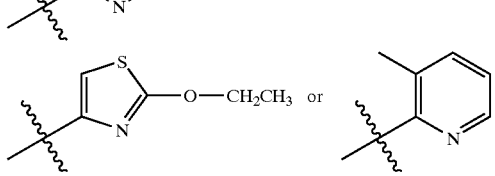

wherein R and R' are lower alkyl, especially methyl, or, in a broader aspect of the invention, furthermore R' is hydroxymethyl or fluoromethyl and R is hydrogen or methyl;

(ii) and, if $R_3$ is lower alkyl, especially methyl, ethyl, n-propyl, iso-propyl, n-butyl, iso-butyl, tert-butyl, n-pentyl, n-hexyl; —CH=CH₂; —C≡CH; —CH₂F; —CH₂Cl; —CH₂—OH; —CH₂—O—($C_1$-$C_6$-alkyl), especially —CH₂—O—CH₃; or —CH₂—S—($C_1$-$C_6$-alkyl), especially —CH₂—S—CH₃, and the other symbols except $R_1$ have the meanings given above, $R_1$ can also be a radical selected from the following structures:

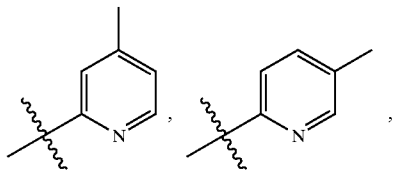

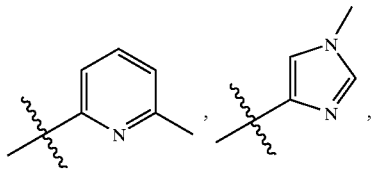

-continued

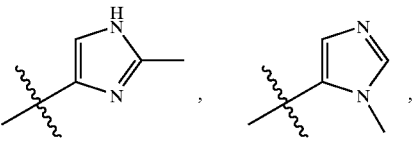

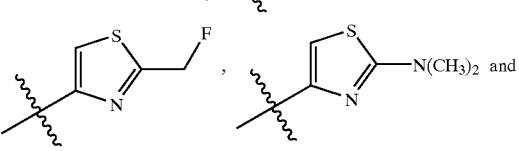

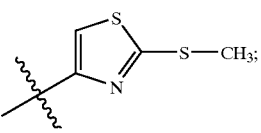

or, if $R_3$ has one of the meanings given in the definition of $R_3$ above under (ii) other than methyl, $R_1$ can also be a radical of the formula

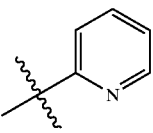

(iii) and, if $R_3$ is hydrogen, lower alkyl, especially methyl, ethyl, n-propyl, iso-propyl, n-butyl, iso-butyl, tert-butyl, n-pentyl, n-hexyl; —CH=CH₂; —C≡CH; —CH₂F; —CH₂Cl; —CH₂—OH; —CH₂—O—($C_1$-$C_6$-alkyl), especially —CH₂—O—CH₃; or —CH₂—S—($C_1$-$C_6$-alkyl), especially —CH₂—S—CH₃, and $R_2$ is oxygen, "b" and "c" are each a single bond and "a" is a single bond, then $R_1$ can also be a radical of the partial formula:

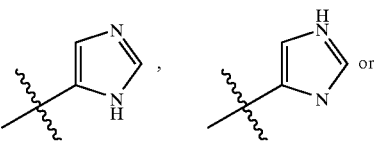

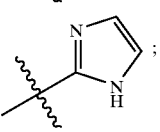

(iv) and, if $R_3$ is lower alkyl other than methyl, especially ethyl, n-propyl, iso-propyl, n-butyl, iso-butyl, tert-butyl, n-pentyl, n-hexyl; or preferably is —CH=CH₂; —C≡CH; —CH₂F; —CH₂Cl; —CH₂—OH; —CH₂—O—($C_1$-$C_6$-alkyl), especially —CH₂—O—CH₃; or —CH₂—S—($C_1$-$C_6$-alkyl), especially —CH₂—S—CH₃; and the other symbols except for $R_1$ have the meanings given above under (i), $R_1$ can also be a moiety of the formula

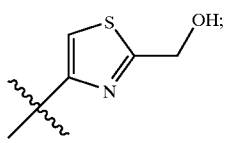

or a salt of a compound of the formula I where a salt-forming group is present.

A further aspect of the invention relates to a method of synthesis of a compound of the formula

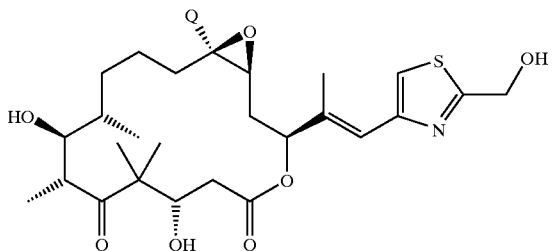

(wherein Q is hydrogen or preferably methyl) and/or a method of synthesis of a compound of the formula

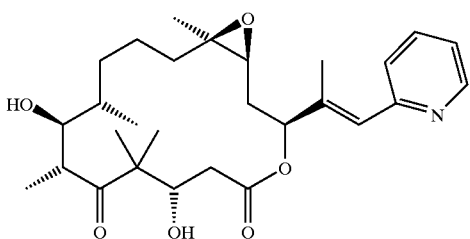

The general terms used hereinbefore and hereinafter preferably have within the context of this disclosure the following meanings, unless otherwise indicated:

The term "lower" means that the respective radical preferably has up to and including 7, more preferably up to and including 4 carbon atoms.

Lower alkyl can be linear or branched one or more times and has preferably up to and including 7, more preferably up to and including 4 carbon atoms. Preferably, lower alkyl is methyl, ethyl, n-propyl, iso-propyl, n-butyl, iso-butyl, tert-butyl or further n-pentyl or n-hexyl.

A protecting group is preferably a standard protecting group. If one or more other functional groups, for example carboxy, hydroxy, amino, or mercapto, are or need to be protected in a compound of formulae I, because they should not take part in the reaction, these are such groups as are usually used in the synthesis of peptide compounds, and also of cephalo-sporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974. Especially preferred protecting groups are hydroxy protecting groups, such as tert-butyldimethylsilyl or trityl.

$R_4$ and $R_5$ are preferably hydrogen.

The waved bond starting from the carbon atom bearing $R_3$ means that bond "a" is present in the trans- or preferably the cis-form.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, maleic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The term "about" in connection with numerical values, e.g. "about 2-fold molar excess" or the like, is preferably intended to mean that the given numerical value may deviate from the given number by up to ±10%, more preferably by up to ±3%; most preferably, the numerical value is exactly as given.

In a preferred embodiment of the invention, the compounds of formula I as described under (iv) above

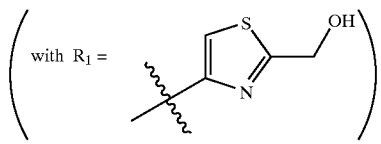

are excluded from the scope of the invention.

Also, a group of compounds of the formula I without a compound of the formulae I wherein $R_1$ is a moiety of any one of the formulae

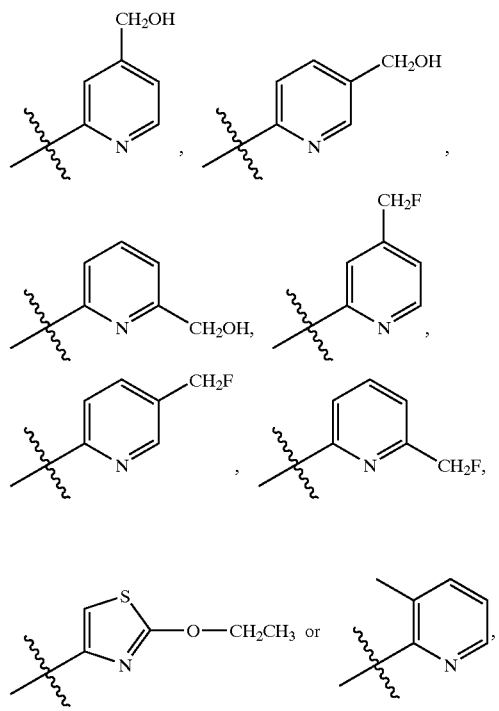

is preferred (the remaining symbols having the meanings defined for a compound of the formula I).

Especially preferred is either a free compound of the formula I, or a salt thereof.

Bioactivity: The compound(s) of the invention can be used for the treatment of a proliferative disease, especially a cancer, like cancers of the lung, especially non-small lung cell lung carcinoma, of the prostate, of the intestine, e.g. colorectal cancers, epidermoid tumors, such as head and/or neck tumors, or breast cancer, or other cancers like cancers of the bladder, pancreas or brain or melanoma, including especially the treatment of cancers that are multidrug-resistant (e.g. due to the expression of p-glycoprotein=P-gp) and/or refractory to treatment with paclitaxel (e.g. in the form of TAXOL).

Biological Evaluation

The ability of the compounds of the present invention to block the depolymerization of microtubuli can be shown by the following assay:

Microtubule assays are carried out following literature procedures and evaluate synthesized compounds for their ability to form and stabilize microtubules. Cytotoxicity studies are carried out as well.

The compounds of formula I are tested for their action on tubulin assembly using purified tubulin with an assay developed to amplify differences between compounds more active than Taxol. Compounds of the formula I are found to have a high level of cytotoxic and tubulin polymerization activity, as compared to Epothilones A and B. (Lin et al. Cancer Chemother. Pharmacol. 38, 136–140 (1996); Rogan et al. Science 244, 994–996 (1984)).

Filtration Colorimetric Assay

Microtubule protein (0.25 ml of 1 mg/ml) is placed into an assay tube and 2.5 $\mu$l of the test compound are added. The sample is mixed and incubated at 37° C. for 30 min. Sample (150 $\mu$l) is transferred to a well in a 96-well Millipore Multiscreen Durapore hydrophilic 0.22 $\mu$m pore size filtration plate which has previously been washed with 200 $\mu$l of MEM buffer under vacuum. The well is then washed with 200 $\mu$l of MEM buffer. To stain the trapped protein on the plate, 50 $\mu$l amido black solution [0.1% naphthol blue black (Sigma)/45% methanol/10% acetic acid] are added to the filter for 2 min; then the vacuum is reapplied. Two additions of 200 $\mu$l amido black destain solution (90% methanol/2% acetic acid) are added to remove unbound dye. The signal is quantitated by the method of Schaffner and Weissmann et al. *Anal. Biochem.*, 56: 502–514, 1973 as follows: 200 $\mu$l of elution solution (25 mM NaOH-0.05 mm EDTA-50% ethanol) are added to the well and the solution is mixed with a pipette after 5 min. Following a 10-min incubation at room temperature, 150 $\mu$l of the elution solution are transferred to the well of a 96-well plate and the absorbance is measured on a Molecular Devices Microplate Reader.

Cytotoxicity experiments with 1A9, 1A9PTX10 ($\alpha$-tubulin mutant), and 1A9PTX22 ($\alpha$-tubulin mutant) cell lines can reveal the cytotoxic activity of the compounds of formula I. Like the naturally occurring epothilones 1 and 2, compounds of the formula I show significant activity against the altered $\alpha$-tubulin-expressing cell lines 1A9PTX10 and 1A9PTX22. For compounds of the formula I, the preferred IC50 values (concentration where half-maximal growth inhibition of tumor cells is found in comparison with a control without added inhibitor of the formula I) can lie in the range of 1 to 1000 nM, preferably from 1 to 200 nM.

The ability of the compounds of the present invention to inhibit tumor growth can be shown by the following assays with the following cell lines:

Colorimetric Cytotoxicity Assay for Anticancer-Drug Screening

The calorimetric cytotoxicity assay used is adapted from Skehan et al (*Journal of National Cancer Inst* 82:1107–1112, 19901). The procedure provides a rapid, sensitive, and inexpensive method for measuring the cellular protein content of adherent and suspension cultures in 96-well microtiter plates. The method is suitable for the National Cancer Institute's disease-oriented in vitro anticancer-drug discovery screen.

In particular, cultures fixed with trichloroacetic acid are stained for 30 minutes with 0.4% (wt/vol) sulforhodamine B (SRB) dissolved in 1% acetic acid. Unbound dye is removed by four washes with 1% acetic acid, and protein-bound dye is extracted with 10 mM unbuffered Tris base [tris (hydroxymethyl)aminomethane] for determination of optical density in a computer-interfaced, 96-well microtiter plate reader. The SRB assay results are linear with the number of cells and with values for cellular protein measured by both the Lowry and Bradford assays at densities ranging from sparse subconfluence to multilayered supraconfluence. The signal-to-noise ratio at 564 nm is approximately 1.5 with 1,000 cells per well.

The SRB assay provides a calorimetric end point that is nondestructive, indefinitely stable, and visible to the naked eye. It provides a sensitive measure of drug-induced cytotoxicity. SRB fluoresces strongly with laser excitation at 488 nm and can be measured quantitatively at the single-cell level by static fluorescence cytometry (Skehan et al (*Journal of National Cancer Inst* 82:1107–1112, 19901)).

Alternatively, the efficiency of the compounds of the formula I as inhibitors of microtubuli depolymerisation can be demonstrated as follows:

Stock solutions of the test compounds are made in DMSO and stored at −20° C. Microtubuli-protein is obtained from pig brain by two cycles of temperature dependent depolymerisation/polymerisation, as described (see Weingarten et al., Biochemistry 1974; 13: 5529–37). Working stock solutions of microtubule protein (meaning tubulin plus microtubuli-associated proteins) are stored at −70° C. The degree of the microtubuli protein polymerisation induced by a test compound is measured essentially as known from the literature (see Lin et al., Cancer Chem. Pharm. 1996; 38:136–140). In short, 5 μl stock solution of the test compound are pre-mixed in the twenty-fold of the desired final concentration with 45 μl of water at room temperature, and the mixture is then placed on ice. An aliquot of the working stock solution of pig brain microtubuli protein is thawed quickly and then diluted to 2 mg/ml with ice-cold 2× MEM buffer (200 ml MES, 2 mM EGTA, 2 mM $MgCl_2$, pH 6.7) (MES=2-morpholinoethanesulfonic acid, EGTA=ethylenglycol-bis-(2(2-aminoethyl)-tetraacetic acid). The polymerisation reaction is then started by the addition of each time 50 μl diluted microtubuli-protein to the test compound, followed by incubation of the sample in a water bath with room temperature. Then the reaction mixtures are placed in an Eppendorf microcentrifuge and incubated for additional 15 min at room temperature. The samples are then centrifuged for 20 min at 14000 rpm at room temperature for separating polymerized from non-polymerized microtubuli protein. As indirect measure for the tubulin-polymerisation the protein concentration of the supernatant (which contains the rest of the un-polymerised, soluble microtubuti protein) is determined according to the Lowry method (DC Assay Kit, Bio-Rad Laboratories, Hercules, Calif.), and the optical density (OD) of the color reaction is determined at 750 nm with a spectrometer (SpectraMax 340, Molecular Devices, Sunnyvale, Calif.). The differences in the OD's between samples treated with a test compound and vehicle-treated controls are compared with those of test incubations which contain 25 μM Epothilon B (positive controls). The degree of polymerisation that is induced by a test compound is expressed relatively to the positive controls (100%). By comparison of several concentrations the EC50 (concentration where 50% of the maximal polymerisation is found) can be determined. For compounds of the formula I the EC50 lies preferably in the range of 1 to 200, preferably 1 to 50 μM. The induction of tubulin polymerisation of test compound of the formula I in 5 μM concentration as parentage in comparison to 25 μM epothilone B preferably lies in the range of 50 to 100%, especially 80 to 100%.

The efficiency against tumor cells can also be shown in the following way:

Stock solutions of the test compound of formula I 10 mM) in DMSO are prepared and stored at −20° C. Human KB-31 and (multidrug-resistant, P-gp 170 overexpressing) KB-8511 epidermoid carcinoma cells are from Dr. M. Baker, Roswell Park Memorial Institute (Buffalo, N.Y., USA) (for description see also Akiyama et al., Somat. Cell. Mol. Genetics 11, 117–126 (1985) und Fojo A., et al., Cancer Res. 45, 3002–3007 (1985)—KB-31 and KB-8511 both are derivatives of the KB-cell line (American Type Culture Collection) and are human epidermoid carcinoma cells. KB-31 cells can be cultivated in mono-layers using calf serum (M.A. Bioproducts), L-glutamine (Flow), penicillin (50 Units/ml) and streptomycin (50 μg/ml (Flow); they then grow with a doubling rate of about 22 hours, and the relative efficiency of plating them out lies at about 60%. KB-8511 is a variant derived from the KB-31 cell line which has been obtained by treatment cycles with colchicine, and it shows an about 40-fold relative resistance against colchicin in comparison to KB-31 cells). The cells are incubated at 37° C. in an incubator with 5% v/v $CO_2$ and at 80% relative atmospheric humidity in MEM Alpha-medium which contains ribonucleosides and desoxyribonucleosides (Gibco BRL), complemented with 10 IU Penicillin, 10 μg/ml Streptomycin and 5% fetal calf serum. The cells are spread in an amount of $1.5 \times 10^3$ cells/well in 96-well-microtiter plates and incubated overnight. Serial dilutions of the test compounds in culture medium are added at day 1. The plates are then incubated for an additional period of four days, after which the cells are fixed using 3.3% v/v glutaraldehyde washed with water and finally stained with 0.05% w/v methylen blue. After washing again, the stain is eluted with 3% HCl and the optical density at 665 nm is measured with a SpectraMax 340 (Molecular Devices, Sunnyvale, Calif.). IC50-values are determined by mathematically fitting the data to curves using the SoftPro2.0 program (Molecular Devices, Sunnyvale, Calif.) and the formula

[(*OD* treated)−(*OD* start)]/[(*OD* control)−(*OD* start)]×100.

The IC50 is defined as the concentration of a test compound at the end of the incubation period that leads to 50% of the number of cells in comparison to controls without test compound (concentration at halfmaximal inhibition of cell growth). Compounds of the formula I preferably show here and IC50 in the range from $0.1 \times 10^{-9}$ to $500 \times 10^{-9}$ M, preferably between 0.1 and 60 nM.

Comparable testing can also be made with other tumor cell lines, such as A459 (lung; ATCC CCL 185), NCIH460 (lung), Colo 205 (colon; ATCC No. CCL 222) (HCT-15 (colon; ATCC CCL 225—ATCC=American Type Culture Collection (Rockville, Md., USA)), HCT-116 (colon), Du145 (prostate; ATCC No. HTB 81; see also Cancer Res. 37, 4049–58 [1978]), PC-3M (prostate-hormone-insensitive derivative obtained from Dr. I. J. Fidler (M D Anderson Cancer Center, Houston, Tex., USA) and derived from PC-3 that is a cell line available from ATCC (ATCC CRL 1435)), MCF-7 (breast; ATCC HTB 22) or MCF-7/ADR (breast, multidrug resistant; for description see Blobe G. C.et al., J. Biol. Chem. (1983), 658–664; the cell line is highly resistant (360- to 2400-fold) to doxorubicin and Vinca alkaloids compared over MDR-7 "wild type" cells)), where similar results are obtained as with KB-31 and KB-8511 cells. Compounds of the formula I preferably show here and IC50 in the range from $0.1 \times 10^{-9}$ to $500 \times 10^{-9}$ M, preferably between 0.1 and 60 nM.

Based on these properties, the compounds of the formula I (meaining also salts thereof) are appropriate for the treatment of proliferative diseases, such as especially tumor diseases, including also metastasis where present, for example of solid tumors, such as lung tumor, breast tumor, colorectal cancer, prostate cancer, melanoma, brain tumor, pancreas tumor, head-and-neck tumor, bladder cancer, neuroblastoma, pharyngeal tumor, or also of proliferative diseases of blood cells, such as leukaemia; or further for the treatment of other diseases that respond to treatment with microtubuli depolymerisation inhibitors, such as psoriasis. The compounds of formula I, or salts thereof, are also appropriate for covering medical implants (useful in prophylaxis of restenosis) (see WO 99/16416, priority Sep. 29, 1997).

The in vivo activity of a compound of the invention can be demonstrated with the following animal model:

Female or male BALB/c nu/nu (nude) mice are kept under sterile conditions (10 to 12 mice per Type III cage) with free access to food and water. Mice weigh between 20 and 25 grams at the time of tumor implantation. Tumors are established by subcutaneous injection of cells (minimum $2 \times 10^6$ cells in 100 µl PBS or medium) in carrier mice (4–8 mice per cell line). The resulting tumors are serially passaged for a minimum of three consecutive transplantations prior to start of treatment. Tumor fragments (approx. 25 mg) are implanted s.c. into the left flank of animals with a 13-gauge trocar needle while the mice are exposed to Forene (Abbott, Switzerland) anesthesia.

Tumor growth and body weights are monitored once or twice weekly. All treatments are administered intravenously (i.v.) and are initiated when a mean tumor volume of approximately 100 to 250 mm³ is attained, depending upon the tumor type. Tumor volumes are determined using the formula (L×D×π)/6 (see Cancer Chemother. Pharmacol. 24:148–154, [1989]). Treatments with epothilones of the formula I vary the dose and the frequency of administration. Comparator agents are administered according to previously determined optimal treatment regimens. In addition to presenting changes in tu-mor volumes over the course of treatment, antitumor activity is expressed as T/C% (mean increase of tumor volumes of treated animals divided by the mean increase of tumor volu-mes of control animals multiplied by 100). Tumor regression (%) represents the smallest mean tumor volume compared to the mean tumor volume at the start of treatment, accor-ding to the formula Regression (%)=(1−Vend/Vstart)×100 (Vend=final mean tumor volume, Vstart=mean tumor volume at the start of treatment.

With this model, the inhibitory effect of a compound of the invention on growth e.g. of tumors derived from the following cell lines can be tested:

Human colorectal adenocarcinoma cell line HCT-15 (ATCC CCL 225) is from the American Type Culture Collection (Rockville, Md., USA), and the cells are cultivated in vitro as recommended by the supplier. HCT-15 is an epithelial-like cell line (Cancer Res. 39: 1020–25 [1979]) that is multi-drug resistant by virtue of over-expression of P-glycoprotein (P-gp, gp170, MDR-1; Anticancer Res. 11: 1309–12 [1991]; J. Biol. Chem. 264: 18031–40 [1989]; Int. J. Cancer 1991; 49: 696–703 [1991]) and glutathione-dependent resistance mechanisms (Int. J. Cancer 1991; 49: 688–95.[1991]). The Colo 205 cell line is also a human colon carcinoma cell line (ATCC No. CCL 222; see also Cancer Res. 38, 1345–55 [1978] which was isolated from ascitic fluid of a patient, dis-plays epithelial-like morphology and is generally considered to be drug-sensitive. A human androgen-independent prostate cancer cell line is used to establish subcutaneous and orthotopic models in mice. The human metastatic prostate carcinoma PC-3M is obtained from Dr. I. J. Fidler (M D Anderson Cancer Center, Houston, Tex., USA) and is cultured in Ham's F12K media supplemented with 7% v/v FBS. The PC-3M cell line is the result of isolation from liver metastasis produced in nude mice subsequent to intrasplenic injection of PC-3 cells [ATCC CRL 1435; American Type Culture Collection (Rockville, Md., USA)], and they can grow in Eagle's MEM supplemented with 10% fetal bovine serum, sodium pyruvate, non-essential amino acids, L-glutamine, a two-fold vitamin solution (Gibco Laboratories, Long Island, N.Y.) and penicillin-streptomycin (Flow Laboratories, Rockville, Md.). The PC-3M cell line is hormone-insensitive (that is, it grows in the absence of androgens). The PC-3 cell line is androgen receptor negative, as is presumably the derived PC-3M cell line. PC-3 is a cell line available from ATCC (ATCC CRL 1435) and corresponds to a grade IV prostatic adenocarcinoma isolated from a 62-year-old Caucasian male; the cells exhibit low acid phosphatase and testosterone-5-a-reductase activity. The cells are near-triploid with a modal number of 62 chromosomes. No normal Y chromosomes can be detected by Q-band analysis. Human lung adenocarcinoma A549 (ATCC CCL 185; isolated as explant culture from lung carcinoma tissue from a 58-year-old Caucasian male); shows epithelial morphology and can synthesize lecithin with a high percentage of desaturated fatty acids utilizing the cytidine diphosphocholine pathway; a subtelocentric marker chromosome involving chromosome 6 and the long arm of chromosome 1 is found in all metaphases. The human breast carcinoma ZR-75-1 (ATCC CRL 1500; isolated from a malignant ascitic effusion of a 63-year-old Caucasian female with infiltrating ductal carcinoma); is of mammary epithelial origin; the cells possess receptors for estrogen and other steroid hormones and have a hypertriploid chromosome number. The human epidermal (mouth) carcinoma cell line KB-8511 (a P-gp over-expressing cell line derived from the epidermoid (mouth) KB-31 carcinoma cell line) is obtained from Dr. R. M. Baker, Roswell Park Memorial Institute (Buffalo, N.Y., USA) (for description see Akiyama et al., Somat. Cell. Mol. Genetics 11, 117–126 (1985) and Fojo A., et al., Cancer Res. 45, 3002–3007 (1985)) and is cultured as previously described (Meyer, T., et al., Int. J. Cancer 43, 851–856 (1989)). KB-8511 cells, like KB-31, are derived from the KB cell line (ATCC) and they are human epidermal carcinoma cells; KB-31 cells can be grown in mono-layer using Dulbecco's modified Eagle's medium (D-MEM) with 10% fetal calf serum (M.A. Bioproducts), L-glutamine (Flow), penicillin (50 units/ml) and streptomycin (50 mg/ml (Flow); they then grow with a doubling time of 22 h, and their relative plating efficiency is approximately 60%. KB-8511 is a cell line derived from the KB-31 cell line by use of colchicine treatment cycles; it shows about a 40-fold relative resistance against colchicine when compared with the KB-31 cells; it can be grown under the same conditions as KB-31."

Solubility: The water solubility is determined as follows, for example: the compounds of formula I, or the salts thereof, are stirred with water at room temperature until no further compound dissolves (about 1 hour). The solubilities found are preferably between 0.01 and 1% by weight.

Within the groups of preferred compounds of formula I mentioned hereinafter, definitions of substituents from the general definitions mentioned hereinbefore may reasonably be used, for example, to replace more general definitions with more specific definitions or especially with definitions characterised as being preferred.

The invention preferably relates to a compound of the formula I wherein $R_2$ is absent or oxygen; "a" can be either a single or double bond; "b" can be either absent or a single bond; and "c" can be either absent or a single bond, with the proviso that if $R_2$ is oxygen then "b" and "c" are both a single bond and "a" is a single bond; if $R_2$ is absent then "b" and "c" are absent and "a" is a double bond; and if "a" is a double bond, then $R_2$, "b" and "c" are absent;

$R_3$ is a radical selected from the group consisting of hydrogen; lower alkyl, especially methyl, ethyl, n-propyl, iso-propyl, n-butyl, iso-butyl, tert-butyl, n-pentyl, n-hexyl; —CH=CH$_2$; —C≡CH; —CH$_2$F; —CH$_2$Cl; —CH$_2$—OH; —CH$_2$—O—(C$_1$-C$_6$-alkyl), especially —CH$_2$—O—CH$_3$; and —CH$_2$—S—(C$_1$-C$_6$-alkyl), especially —CH$_2$—S—CH$_3$;

R$_4$ and R$_5$ are independently selected from hydrogen, methyl or a protecting group, preferably hydrogen; and R$_1$ is a radical selected from the following structures:

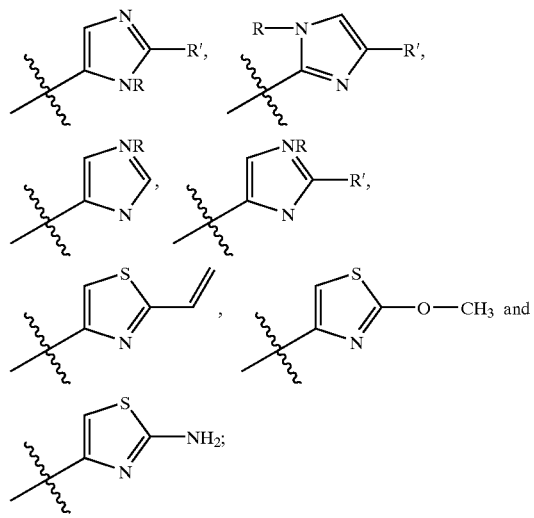

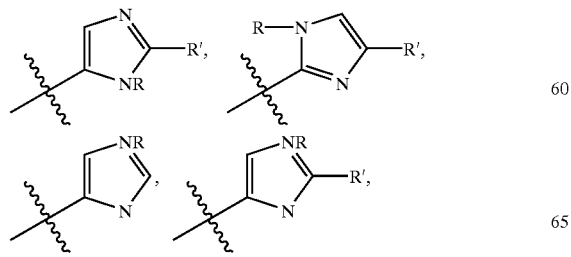

wherein R and R' are lower alkyl, especially methyl; or a salt thereof where salt-forming groups are present.

The invention preferably also relates to a compound of the formula I wherein

R$_2$ is absent or oxygen; "a" can be either a single or double bond; "b" can be either absent or a single bond; and "c" can be either absent or a single bond, with the proviso that if R$_2$ is oxygen then "b" and "c" are both a single bond and "a" is a single bond; if R$_2$ is absent then "b" and "c" are absent and "a" is a double bond; and if "a" is a double bond, then R$_2$, "b" and "c" are absent;

R$_3$ is a radical selected from the group consisting of hydrogen; lower alkyl, especially methyl, ethyl, n-propyl, iso-propyl, n-butyl, iso-butyl, tert-butyl, n-pentyl, n-hexyl; —CH=CH$_2$; —C≡CH; —CH$_2$F; —CH$_2$Cl; —CH$_2$—OH; —CH$_2$—O—(C$_1$-C$_6$-alkyl), especially —CH$_2$—O—CH$_3$; and —CH$_2$—S—(C$_1$-C$_6$-alkyl), especially —CH$_2$—S—CH$_3$;

R$_4$ and R$_5$ are independently selected from hydrogen, methyl or a protecting group, preferably hydrogen; and R$_1$ is a radical selected from the following structures:

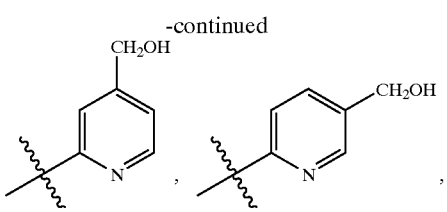

-continued

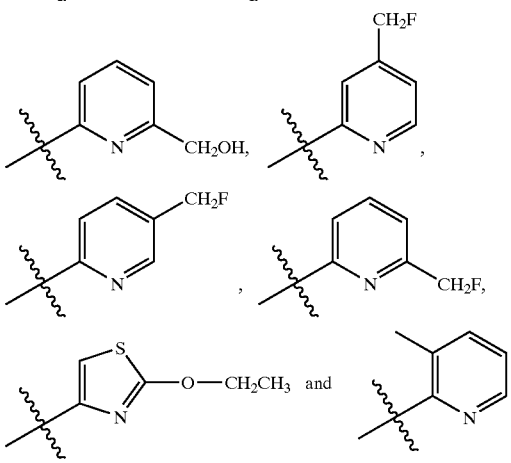

wherein R' is hydroxymethyl or fluoromethyl and R is hydrogen or methyl;

or a salt thereof where a salt-forming group is present.

The invention preferably also relates to a compound of the formula I wherein

R$_2$ is absent or oxygen; "a" can be either a single or double bond; "b" can be either absent or a single bond; and "c" can be either absent or a single bond, with the proviso that if R$_2$ is oxygen then "b" and "c" are both a single bond and "a" is a single bond; if R$_2$ is absent then "b" and "c" are absent and "a" is a double bond; and if "a" is a double bond, then R$_2$, "b" and "c" are absent;

R$_3$ is a radical selected from the group consisting of lower alkyl, especially methyl, ethyl, n-propyl, iso-propyl, n-butyl, iso-butyl, tert-butyl, n-pentyl, n-hexyl; —CH=CH$_2$; —C≡CH; —CH$_2$F; —CH$_2$Cl; —CH$_2$—OH; —CH$_2$—O—(C$_1$-C$_6$-alkyl), especially —CH$_2$—O—CH$_3$; and —CH$_2$—S—(C$_1$-C$_6$-alkyl), especially —CH$_2$—S—CH$_3$, R$_4$ and R$_5$ are independently selected from hydrogen, methyl or a protecting group, preferably hydrogen; and R$_1$ is a radical selected from the following structures:

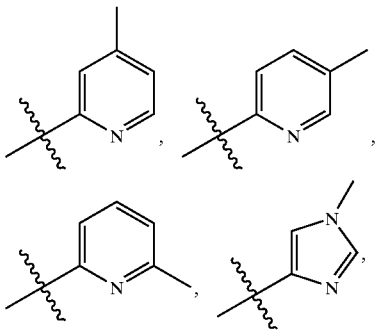

-continued

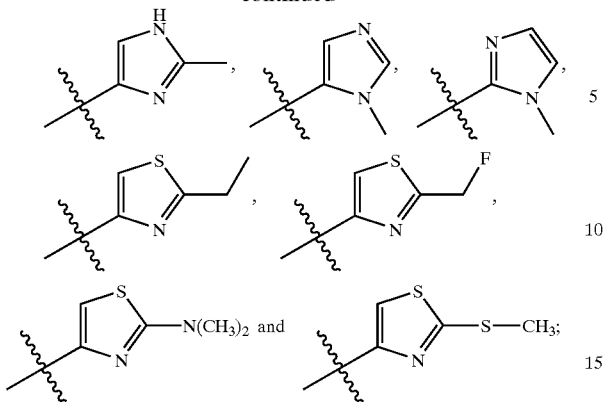

or a salt thereof where one or more salt-forming groups are present.

The invention preferably also relates to a compound of the formula I wherein

R₂ is absent or oxygen; "a" can be either a single or double bond; "b" can be either absent or a single bond; and "c" can be either absent or a single bond, with the proviso that if R₂ is oxygen then "b" and "c" are both a single bond and "a" is a single bond; if R₂ is absent then "b" and "c" are absent and "a" is a double bond; and if "a" is a double bond, then R₂, "b" and "c" are absent;

R₃ is a radical selected from the group consisting of lower alkyl other than methyl, especially ethyl, n-propyl, iso-propyl, n-butyl, iso-butyl, tert-butyl, n-pentyl, n-hexyl; —CH=CH₂; —C≡CH; —CH₂F; —CH₂Cl; —CH₂—OH; —CH₂—O—(C₁-C₆-alkyl), especially —CH₂—O—CH₃; and —CH₂—S—(C₁-C₆-alkyl), especially —CH₂—S—CH₃, R₄ and R₅ are independently selected from hydrogen, methyl or a protecting group, preferably hydrogen; and R₁ is a radical of the formula

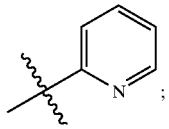

or a salt thereof if one or more salt-forming groups are present.

The invention preferably also relates to a compound of the formula I wherein

R₂ is oxygen, "b" and "c" are each a single bond and "a" is a single bond,

R₃ is a radical selected from the group consisting of lower alkyl, especially methyl, ethyl, n-propyl, iso-propyl, n-butyl, iso-butyl, tert-butyl, n-pentyl, n-hexyl; —CH=CH₂; —C≡CH; —CH₂F; —CH₂Cl; —CH₂—OH; —CH₂—O—(C₁-C₆-alkyl), especially —CH₂—O—CH₃; and —CH₂—S—(C₁-C₆-alkyl), especially —CH₂—S—CH₃, R₄ and R₅ are independently selected from hydrogen, methyl or a protecting group, preferably hydrogen; and R₁ is a radical selected from the group consisting of the following structures:

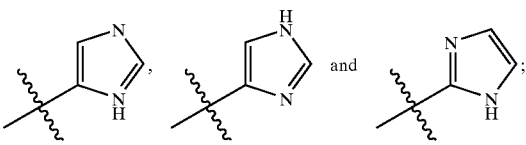

or a salt thereof where one or more salt-forming groups are present.

The invention preferably also relates to a compound of the formula I wherein

R₂ is absent or oxygen; "a" can be either a single or double bond; "b" can be either absent or a single bond; and "c" can be either absent or a single bond, with the proviso that if R₂ is oxygen then "b" and "c" are both a single bond and "a" is a single bond; if R₂ is absent then "b" and "c" are absent and "a" is a double bond; and if "a" is a double bond, then R₂, "b" and "c" are absent;

R₃ is a radical selected from the group consisting of lower alkyl other than methyl, especially ethyl, n-propyl, iso-propyl, n-butyl, iso-butyl, tert-butyl, n-pentyl or n-hexyl; —CH=CH₂; —C≡CH; —CH₂F; —CH₂Cl; —CH₂—OH; —CH₂—(C₁-C₆-alkyl), especially —CH₂—O—CH₃; and —CH₂—S—(C₁-C₆-alkyl), especially —CH₂—S—CH₃, R₄ and R₅ are independently selected from hydrogen, methyl or a protecting group, preferably hydrogen; and R₁ is a radical of the formula

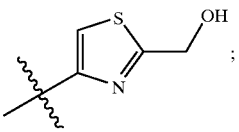

or a salt of a compound of the formula I where a salt-forming group is present.

More preferably, the invention relates to a compound of the formula Ia, (Ia)

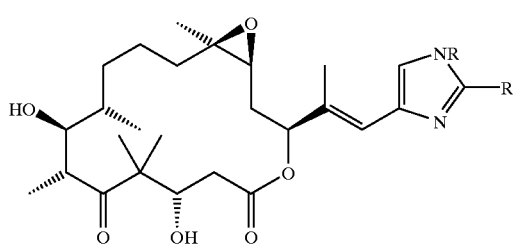

wherein, independent of each other, the R moieties are hydrogen or methyl, or a salt thereof.

More preferably, the invention also relates to a compound of the formula Ib,

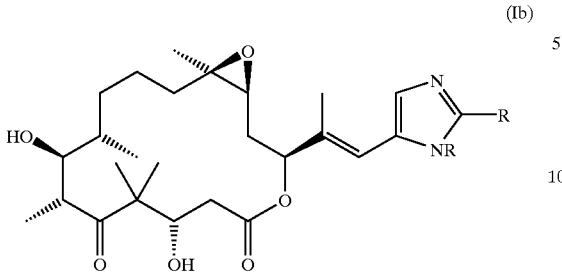

(Ib)

wherein, independent of each other, the R moieties are hydrogen or methyl, or a salt thereof.

The invention most specifically also relates to a compound of the formula Ic

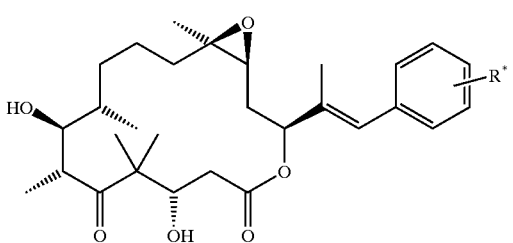

(Ic)

wherein R* is methyl.

The invention most specifically also relates to a compound of the formula Id

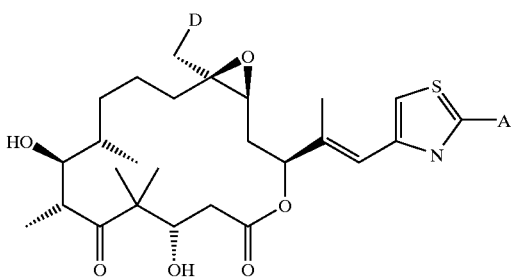

(Id)

wherein A is ethyl, fluoromethyl, methoxy, methylthio or ethenyl (—CH=CH$_2$) and D is hydrogen, fluoro, hydroxy or methyl, especially hydrogen.

The invention most specifically also relates to a compound of the formula Ie

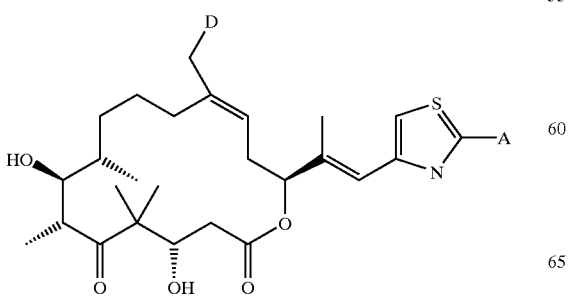

(Ie)

wherein A is ethyl, fluoromethyl, methoxy, methylthio or ethenyl (—CH=CH$_2$) and D is hydrogen, fluoro, hydroxy or methyl.

The invention most specifically relates to the compounds of the formula I given in the examples, or the pharmaceutically acceptable salts thereof where one or more salt-forming groups are present.

Most preferably, the invention relates to a compound selected from the group consisting of compound D (Example 1), the compound of Example 2 A), the compound of Example 2C, compound 18b (see Example 4), compound 19b (see Example 4), compound 46 (see Example 4), compound 50 (see Example 4), compound 52 (see Example 4), compound 53 (see Example 4), compound 58 (see Example 4), compound 59 (see Example 4), compound 66 (see Example 4), compound 67 (see Example 4), and compound 68 (see Example 4), or a pharmaceutically acceptable salt thereof if one or more salt-forming groups are present.

The compounds of the invention can be synthesized using methods in analogy to methods that are known in the art, preferably by a method characterized by a) reacting a iodide of the formula II,

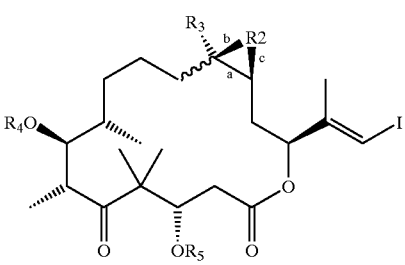

(II)

wherein R$_2$, R$_3$, R$_4$, R$_5$, a, b and c and the waved bond have the meanings given under formula I, with a tin compound of the formula III,

R$_1$—Sn(R)$_3$    (III)

wherein R$_1$ has the meanings given under formula I and R is lower alkyl, especially methyl or n-butyl, or b) reacting a tin compound of the formula IV,

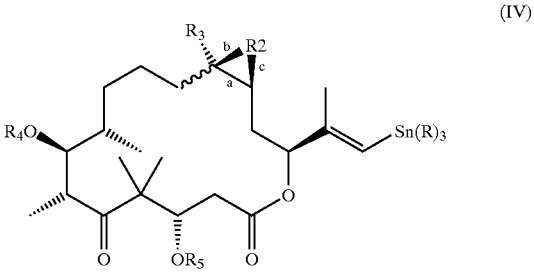

(IV)

wherein $R_2$, $R_3$, $R_4$, $R_5$, a, b and c and the waved bond have the meanings given under formula I, with a iodide of the formula V, $$R_1-I \qquad (V)$$

wherein $R_1$ has the meanings given under formula I; and, if desired, a resulting compound of the formula I is converted into a different compound of the formula I, a resulting free compound of the formula I is converted into a salt of a compound of the formula I, and/or a resulting salt of a compound of the formula I is converted into a free compound of the formula I or into a different salt of a compound of the formula I, and/or a stereoisomeric mixture of compounds of formula I is separated into the corresponding isomers.

DETAILED DESCRIPTION OF THE PREFERRED PROCESS CONDITIONS

In all starting materials, where required, functional groups that shall not participate in the reaction are protected by protecting groups, especially standard protecting groups. The protecting groups, their introduction and their cleavage are known in the art, for example, they are described in the standard references mentioned above.

Reaction a): The reaction (a (preferably improved) Stille coupling) preferably takes place under standard conditions; more preferably, the reaction takes place (i) in an appropriate solvent, e.g. toluene, at elevated temperature, especially about 90 to about 100° C., preferably with an excess of the tin compound of the formula III, preferably in the 1.1- to 3-, e.g. the 1.5- to 2-fold molar excess; and a catalytic amount, preferably of about 1 to 30%, preferably 5 to 10%, of Pd(PPh$_3$)$_4$; or (ii) in an appropriate solvent, e.g. dimethylformamide (DMF), at temperatures of from 10 to 40° C., especially at 25° C., preferably with an excess of the tin compound of the formula III, preferably in the 1.1- to 3-, e.g. the 1.5- to 2.3-fold molar excess; in the presence of a catalytic amount, preferably of 10 to 50%, especially 20 to 30%, of Pd(MeCN)$_2$Cl$_2$. Alternative conditions for this coupling also comprise the use of the following reagents and/or conditions:

(iii). cuprous 2-thiophene carboxylate, N-methyl-2-pyrrolidine.

(iv). PdCl$_2$(MeCN)$_2$ (cat.), DMF, 50–150° (with or without additon of tertiary base).

(v). Pd(PPh$_3$)$_4$/CuI (cat), DMF, 50–150° (with or without addition of tertiary base)

Reaction b): The reaction (an improved Stille coupling) preferably takes place under standard conditions; more preferably, the reaction takes place in an appropriate solvent, especially DMF, at temperatures of from 50 to 100, preferably from 80 to 85° C., preferably with an excess of the iodide of the formula V, in the presence of a catalytic amount of AsPh$_3$, preferably about 0.4 equivalents, CuI, preferably about 0.1 equivalents, and PdCl$_2$(MeCN)$_2$, preferably about 0.2 equivalents.

Especially preferred are the reaction conditions mentioned in the examples.

Conversions of Compounds/salts

Compounds of the formula I can be converted into different compounds of formula I by standard or novel methods.

For example, a compound of the formula I wherein $R_2$ is absent, b and c are absent and a is a double bond, and the other moieties are as described for compounds of the formula I, can be converted into the corresponding epoxide wherein $R_2$ is O and b and c are present while a is a single bond. Preferably, the epoxidation takes place in the presence of (+)-diethyl-D-tartrate ((+)-DET) (preferably about 0.5 equivalents), Ti(i-PrO)$_4$ (preferably about 0.5 equivalents), tert-butylhydroperoxide (preferably about 2.2 equivalents) and molecular sieve, especially 4 Å molecular sieves, in an appropriate solvent, e.g. methylene chloride and optionally an alkane, such as decane, at low temperatures, preferably -78 to 0° C., especially about -40° C.; or in presence of hydrogen peroxide (preferably about 30 equivalents), acetonitrile (preferably about 60 equivalents), a base, especially KHCO$_3$ (preferably about 10 equivalents) in an appropriate solvent, e.g. an alcohol, preferably methanol, at preferred temperatures between 10 and 40° C., e.g. at about 25° C.

A compound of the formula I wherein $R_3$ is hydroxymethyl can be converted into a compound of formula I wherein $R_3$ is fluoromethyl, e.g. by treatment with DAST (preferably 1.05 to 1.4 equivalents) in an appropriate solvent, e.g. methylene chloride, at low temperatures, preferably at -95 to 0° C., especially at about -78° C. DAST is diethylamino-sulfur trifluoride.

A compound of the formula I wherein $R_3$ is iodomethyl can be converted into a compound of formula I wherein $R_3$ is methyl, e.g. by treatment with cyanoborohydride (preferably about 10 equivalents) in HMPA (hexamethylphosphoric triamide) at elevated temperatures, e.g. at 40 to 45° C.

Other conversions can be made in accordance with known procedures, e.g. those given in PCT application WO 98/25929, which is herewith incorporated by reference.

Salts of a compound of formula I with a salt-forming group may be prepared in a manner known per se. Acid addition salts of compounds of formula I may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

The resulting free compounds can then, if desired, be converted into different salts as described for the formation of salts from the free compounds.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Starting Materials

Starting materials and intermediates are known in the art, commercially available, and/or prepared in accordance with methods known in the art or in analogy thereto.

Compounds of the formula II and of the formula III can, for example, be synthesized as described in PCT application WO 98/25929, which is herewith incorporated by reference, or as described or in analogy to the methods in the examples.

Compounds of the formula IV are accessible by reaction of the respective compounds of the formula II, for example by reaction of a compound of the formula II with $(R)_6Sn_2$, wherein R is lower alkyl, especially methyl or n-butyl, in the presence of an appropriate nitrogen base, e.g. Hünig's base, and in the presence of catalytic amount (preferably about 0.1 equivalents) of $Pd(PPh_3)_4$ in an appropriate solvent, e.g. toluene, at elevated temperatures, e.g. 30 to 90° C., especially 80 to 85° C. Iodides of the formula V are known and can be obtained according to literature procedures, or they are commercially available. For example, 2-iodo-6-methyl pyridine can be obtained according to Klei, E.; Teuben, J. H. J. Organomet. Chem. 1981, 214, 53–64; 2-iodo-5-methyl pyridine according to Talik, T.; Talik, Z. Rocz. Chem. 1968, 42, 2061–76; and 2-iodo-4-methyl pyridine according to Talik, T.; Talik, Z. Rocz. Chem. 1968, 42, 2061–76, Yamamoto, Y.; Yanagi, A. Heterocycles 1981, 16, 1161–4 or Katritzky, A. R.; Eweiss, N. F.; Nie, P.-L. JCS, Perkin Trans I 1979, 433–5. The corresponding hydroxymethyl-substituted compounds of formula V are available for example by oxidation of the methyl groups of the iodides mentioned above with $SeO_2$ and subsequent reduction, e.g. with $NaBH_4$ or DIBALH) of the aldehyde or by oxidation of the methyl group to form the acid (for example with $KMnO_4$) and subsequent reduction of the ester e.g. with DIBAL.

Preferably, new or also known starting materials and intermediates can be prepared in accordance with or in analogy to the methods described in the examples, where the amounts, temperatures and the like of the respective reactions can be modified, e.g. by varying in the range of ±99%, preferably ±25%, and other appropriate solvents and reagents can be used.

The invention relates also to all new intermediates, especially those mentioned in the Examples.

The invention also relates to a method of synthesis of a compound of the formula VI

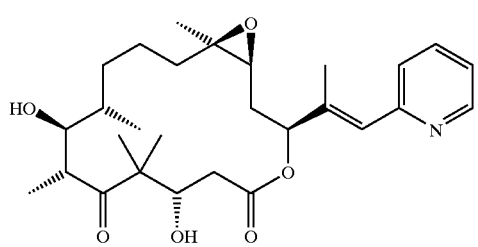

(VI)

which is characterized in that a compound of the formula VII

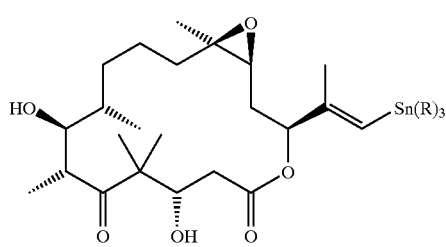

(VII)

wherein $R_3$ is lower alkyl, especially methyl or n-butyl, is coupled with a iodide of the formula VIII,

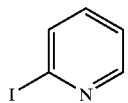

(VIII)

(commercially available, e.g. from TCI, USA), especially under Stille coupling and analogous/modified conditions; especially in an appropriate solvent, especially a di-lower alkyl-lower alkanoyl amide, preferably dimethyl formamide or -acetamide; the compound of formula VIII preferably being in slight molar excess over the compound of the formula VII, e.g. in the 1.1- to 5-fold, especially in the 1.5 to 2.5-fold excess, for example in 2.1-fold excess; in the presence of catalytic amounts of $AsPh_3$ (especially about 0.4 equivalents), $PdCl_2(MeCN)_2$ (especially about 0.2 equivalents) and CuI (especially about 0.1 equivalents); at elevated temperatures, e.g. in the range of 50 to 90° C., preferably about 80 to about 85° C. For further reaction conditions see the detailed description under process variant (a) ("Reaction a)") above for the synthesis of a compound of the formula I. The reaction conditions can be optimized for the particular substrates in accordance with the know-how of the person havin skill in the art.

The invention also relates to the inverted method wherein instead of the compound of the formula VII an analogue is used where instead of the $Sn(R)_3$ moiety a iodine is present and instead of the compound of the formula VIII an analogue is used that has the moiety $Sn(R)_3$ instead of the iodine. The reaction conditions are then analogous to those under method a) presented above for the synthesis of a compound of the formula I.

The invention also relates to a method of synthesis for epothilones E and especially F of the formula IX,

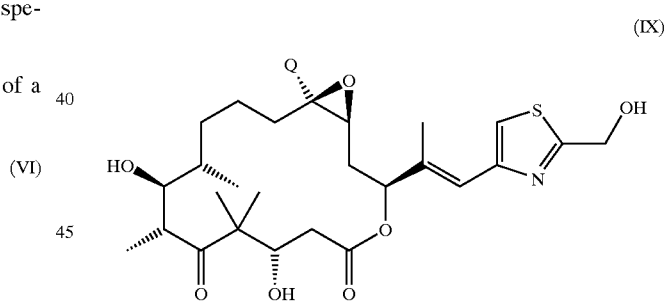

(IX)

wherein Q is hydrogen (epothilone E) or methyl (epothilone F), which is characterized in that a compound of the formula X

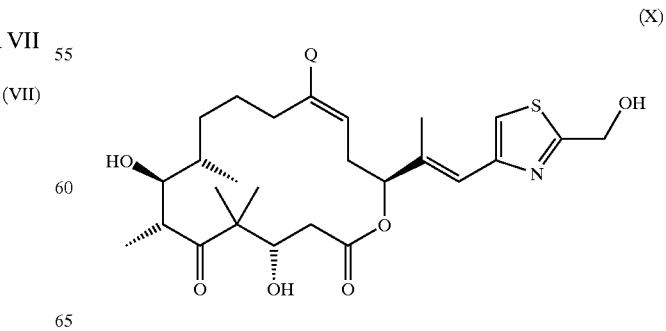

(X)

is epoxidized in the presence of a peroxide to the compound of the formula IX, preferably by using standard reaction conditions for epoxidation, more preferably by epoxidation in the presence of $H_2O_2$, a base, especially $KHCO_3$, acetonitrile and an appropriate solvent, especially an alcohol, e.g. methanol, at temperatures preferably in the range of 0 to 50° C., especially about 25° C. (in-situ-formation if methylperoxycarboximidic acid); or in the presence of (+)-diethyl-D-tartrate and titanium isopropoxide, then t-butyl hydroperoxide in an appropriate solvent, e.g. methylenchloride and optionally decane at low temperatures, e.g. −78 to 0° C., especially about −40° C.

These reactions have inter alia the advantage to provide the final products in high yield and good isomeric purity.

Pharmaceutical Preparations

The present invention also relates to the use of a compound of the formula I for the manufacture of a pharmaceutical formulation for use against a proliferative disease as defined above; or to a pharmaceutical formulation for the treatment of said proliferative disease comprising a compound of the invention and a pharmaceutically acceptable carrier.

The compounds of the formula I are called active ingredient hereinafter.

The invention relates also to pharmaceutical compositions comprising an active ingredient as defined above, for the treatment of a proliferative disease, especially as defined above, and to the preparation of pharmaceutical preparations for said treatment.

The invention relates also to a pharmaceutical composition that is suitable for administration to a warm-blooded animal, especially a human, for the treatment of a proliferative disease as defined hereinbefore, comprising an amount of an active ingredient, which is effective for the treatment of said proliferative disease, together with at least one pharmaceutically acceptable carrier. The pharmaceutical compositions according to the invention are those for enteral, such as nasal, rectal or oral, or preferably parenteral, such as intramuscular or intravenous, administration to a warm-blooded animal (human or animal), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration; preferably, the dose is one of the preferred doses as defined below, being accommodated appropriately where pediatric treatment is intended.

The pharmaceutical compositions comprise from about 0.00002 to about 95%, especially (e.g. in the case of infusion dilutions that are ready for use) of 0.0001 to 0.02%, or (for example in case of infusion concentrates) from about 0.1% to about 95%, preferably from about 20% to about 90%, active ingredient (weight by weight, in each case). Pharmaceutical compositions according to the invention may be, for example, in unit dose form, such as in the form of ampoules, vials, suppositories, dragees, tablets or capsules.

The pharmaceutical compositions of the present invention are prepared in a manner known per se, for example by means of conventional dissolving, lyophilizing, mixing, granulating or confectioning processes.

Solutions of the active ingredient, and also suspensions, and especially isotonic aqueous solutions or suspensions, are preferably used, it being possible, for example in the case of lyophilized compositions that comprise the active ingredient alone or together with a pharmaceutically acceptable carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of anti-oxidants, for example vitamin E, betacarotene or 3,5-di-tert-butyl-4-hydroxytoluene. The alcohol component of those fatty acid esters has a maximum of 6 carbon atoms and is a mono- or polyhydroxy, for example a mono-, di- or tri-hydroxy, alcohol, for example methanol, ethanol, propanol, butanol or pentanol or the isomers thereof, but especially glycol and glycerol.

The injection or infusion compositions are prepared in customary manner under sterile conditions; the same applies also to introducing the compositions into ampoules or vials and sealing the containers.

Preferred is an infusion formulation comprising an active ingredient and a pharmaceutically acceptable organic solvent.

The pharmaceutically acceptable organic solvent used in a formulation according to the invention may be chosen from any such organic solvent known in the art. Preferably the solvent is selected from alcohol, e.g. absolute ethanol or ethanol/water mixtures, more preferably 70% ethanol, polyethylene glycol 300, polyethylene glycol 400, polypropylene glycol or N-methylpyrrolidone, most preferably polypropylene glycol or 70% ethanol or polyethylene glycol 300.

The active ingredient may preferably be present in the formulation in a concentration of about 0.01 to about 100 mg/ml, more preferably about 0.1 to about 100 mg/ml, still more preferably about 1 to about 10 mg/ml (especially in infusion concentrates).

The active ingredient may be used as pure substances or as a mixture with another active ingredient. When used in its pure form it is preferable to employ a concentration of active ingredient of 0.01 to 100, more preferably 0.05 to 50, still more preferably 1 to 10 mg/ml (this number makes reference especially to an infusion concentrate that, before treatment, is diluted accordingly, see below).

Such formulations are conveniently stored in vials or ampoules. Typically the vials or ampoules are made from glass, e.g. borosilicate or soda-lime glass. The vials or ampoules may be of any volume conventional in the art, preferably they are of a size sufficient to accommodate 0.5 to 5 ml of formulation. The formulation is stable for periods of storage of up to 12 to 24 months at temperatures of at least 2 to 8° C.

Formulations must be diluted in an aqueous medium suitable for intravenous administration before the formulation of the active ingredient can be administered to a patient. The infusion solution preferably must have the same or essentially the same osmotic pressure as body fluid.

Accordingly, the aqueous medium preferably contains an isotonic agent which has the effect of rendering the osmotic pressure of the infusion solution the same or essentially the same as body fluid.

The isotonic agent may be selected from any of those known in the art, e.g. mannitol, dextrose, glucose and sodium chloride. Preferably the isotonic agent is glucose or sodium chloride. The isotonic agents may be used in amounts which impart to the infusion solution the same or essentially the same osmotic pressure as body fluid. The precise quantities needed can be determined by routine experimentation and will depend upon the composition of the infusion solution and the nature of the isotonic agent. Selection of a particular isotonic agent is made having regard to the properties of the active agent.

The concentration of isotonic agent in the aqueous medium will depend upon the nature of the particular isotonic agent used. When glucose is used it is preferably used in a concentration of from 1 to 5% w/v, more particularly 5% w/v. When the isotonic agent is sodium chloride it is preferably employed in amounts of up to 1% w/v, in particular 0.9% w/v.

The infusion formulation may be diluted with the aqueous medium. The amount of aqueous medium employed as a diluent is chosen according to the desired concentration of active ingredient in the infusion solution. Preferably the infusion solution is made by mixing a vial or ampoule of infusion concentrate afore-mentioned with an aqueous medium, making the volume up to between 20 ml and 200 ml, preferably between about 50 and about 100 ml, with the aqueous medium.

Infusion solutions may contain other excipients commonly employed in formulations to be administered intravenously. Excipients include antioxidants. Infusion solutions may be prepared by mixing an ampoule or vial of the formulation with the aqueous medium, e.g. a 5% w/v glucose solution in WFI or especially 0.9% sodium chloride solution in a suitable container, e.g. an infusion bag or bottle. The infusion solution, once formed, is preferably used immediately or within a short time of being formed, e.g. within 6 hours. Containers for holding the infusion solutions may be chosen from any conventional container which is nonreactive with the infusion solution. Glass containers made from those glass types afore-mentioned are suitable although it may be preferred to use plastics containers, e.g. plastics infusion bags.

The invention also relates to a method of treatment of a warm-blooded animal, especially a human, that is in need of such treatment, especially of treatment of a proliferative disease, comprising administering a compound of the formula I, or a pharmaceutically acceptable salt thereof, to said warm-blooded animal, especially a human, in an amount that is sufficient for said treatment, especially effective against said proliferative disease.

Dosage forms may be conveniently administered intravenously in a dosage of from 0.01 mg up to 100 mg/m$^2$ of active ingredient, preferably from 0.1 to 20 mg/m$^2$ of active ingredient. The exact dosage required and the duration of administration will depend upon the seriousness of the condition, the condition of the patient and the rate of administration. The dose may be administered daily or preferably with intervals of some days or weeks, for example weekly or every 3 weeks. As the dose may be delivered intravenously, the dose received and the blood concentration can be determined accurately on the basis of known in vivo and in vitro techniques.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can be used alone or in combination with other pharmaceutically active substances, e.g. with other chemotherapeutics, such as classical cytostatics. In the case of combinations with an other chemotherapeutic, a fixed combination of two or more components or two or more independent formulations (e.g. in a kit of part) are prepared as described above, or the other chemotherapeutics are used in standard formulations that are marketed and known to the person of skill in the art, and the compound of the present invention and any other chemotherapeutic are administered at an interval that allows for a common, additional or preferably synergistic effect for tumor treatment.

The following examples are intended to illustrate the present invention without being intended to limit the scope of the invention.

EXAMPLE 1

5-Methylpyridine Analogue D of Epothilone B

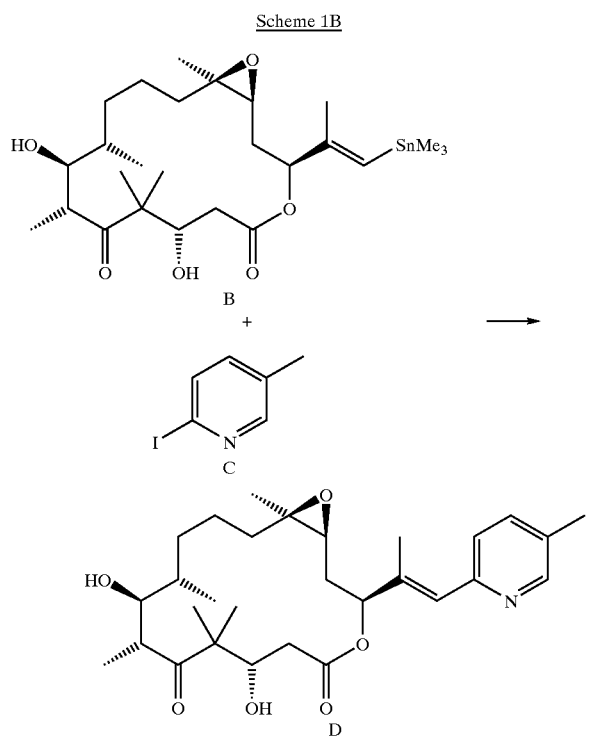

To a solution of B (20 mg, 0.035 mmol) in degassed dimethyl formamide (=DMF; 350 μl, 0.1 M) is added C (17 mg, 0.077 mmol, 2.1 equivalents) followed by AsPh$_3$ (4 mg, 0.4 equivalents), PdCl$_2$(MeCN)$_2$ (2 mg, 0.2 equivalents) and CuI (1 mg, 0.1 equivalents) and the resulting slurry is placed in an oil bath at 80–85° C. for 25 minutes. The reaction mixture is then cooled to room temperature and the DMF removed by distillation. The residue is taken up in ethyl acetate, filtered through a small plug of silica, and eluted with hexane/ethyl acetate (1/1, v/v). The solution is then concentrated in vacuo and purified by preparative TLC (hexane/ethyl acetate 1/2) to give compound D: MS (Electrospray): expected: $(M+H)^+=502$, found: 502. $^1$H-NMR (600 MHz, CDCl$_3$): 8.37 (s, 1H, pyridine H); 7.50 (d, I=7.5 Hz, 1H, pyridine H); 7.19 (d, I=7.5 Hz, 1H, pyridine H), 6.59 (s, 1H, =CH pyridine).

Starting Materials

To a solution of 7002 (see Scheme 11 below) (55 mg, 0.1 mmol) in toluene (1 ml, 0.1 M), Hünig's base is added (4 μl, 0.2 equivalents.), as well as Pd(PPh$_3$)$_4$ (12 mg, 0.1 equivalents) and (Me$_6$)Sn$_2$ (91 μl, 5 equivalents). This solution is then warmed to 80–85° C. for 15 minutes, and then cooled to room temperature. The yellow solution is then filtered through a small plug of silica, and eluted with hexane/ethyl acetate (1/1, v/v). The solution is then concentrated on vacuo and the residue is purified by flash chromatography (hexane/diethyl-ether 1/1 to hexane/ethyl acetate 1/1) to give B (20.2 mg, 34.4%) as a waxy solid. Data for B: HRMS (FAB Cs): Expected: M+Cs=703/705/707.1276, found: 703/705/707.1402. $^1$H-NMR (600 MHz, CDCl$_3$): 5.88 (t, J$_{H-Sn}$=40.6 Hz, 1H, =CH—SnMe$_3$) and 0.18 (t, J$_{H-Sn}$=40.6 Hz, 9H, SnMe$_3$).

EXAMPLE 2

In Analogy to Example 1 the Following Examples are Prepared

Scheme 1A

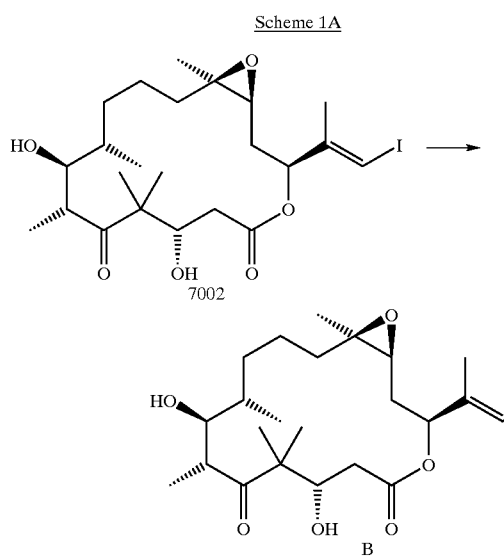

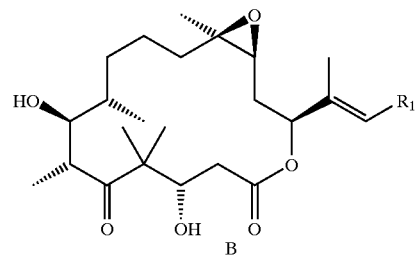

| Compound | R$_1$ | Physical Data | Starting Material |
|---|---|---|---|
| Example 2 A) | 2-pyridyl | Yield = 40%; MS (FAB) Expected (M + Cs): 620.1988, found; 620.2010; $^1$H-NMR (500 MHz, CDCl$_3$): 8.53 (d, J = 4.4 Hz, 1H, pyridine H); 7.72 (t, J = 7.4 Hz, 1H, pyridine H); 7.31 (d, J = 7.7 Hz, 1H, pyridine H); 7.17 (t, J = 6.6 Hz, 1H, pyridine H); 6.65 (s, 1H, =CH pyridine). | B plus 2-iodopyridine |
| Example 2 B) | 3-methyl-2-pyridyl | Yield = 14%; MS (FAB): expected (M + Cs): 634.2145; found 634.2122; $^1$H-NMR (500 MHz, CDCl$_3$): 8.36 (d, J = 4.4 Hz, 1H, pyridine H); 7.53 (d, J = 7.4 Hz, 1H, pyridine H); 7.13 (dd, J = 4.4, 7.4 Hz, 1H, pyridine H); 6.64 (s, 1H, =CH pyridine). | 2-iodo-3-methylpyridine |
| Example 2 C) | 4-methyl-2-pyridyl | Yield = 20%; MS (FAB) expected (M + Cs): 634.2145; found 634.2124; $^1$H-NMR (500 MHz, CDCl$_3$): 8.38 (d, J = 4.8 Hz, 1H, pyridine H); 7.11 (s, 1H, pyridine H); 6.98 (d, J = 4.8 Hz, 1H, pyridine H); 6.59 (s, 1H, =CH pyridine). | 2-iodo-4-methylpyridine |

EXAMPLE 3

Total Synthesis of Epothilone E and Related Side-Chain Modified Analogs via a Stille Coupling Based Strategy The first total synthesis of epothilone E (3) is accomplished by a strategy in which the key step is a Stille coupling (Stille et al. Angew. Chem. Int. Ed. Engl. 1986, 25, 508–524; Farina et al. J. Org. React. 1997, 50, 1–65) between vinyl iodide 7 and the thiazole moiety (8h, Scheme 2a). The macrolactone core fragment 7, which is prepared via ring-closing olefin metathesis (RCM), is subsequently used to provide convenient and flexible access to a variety of side-chain modified epothilone analogs (9) for biological evaluation (Scheme 2b). The RCM reaction used to access 7 also provides trans-macrolactone (11, Scheme 2b) which serves as an alternative template for the Stille coupling process and provides an additional array of analogs 10.

Scheme 2 a) Retrosynthetic analysis and strategy for the total synthesis of epothilone E

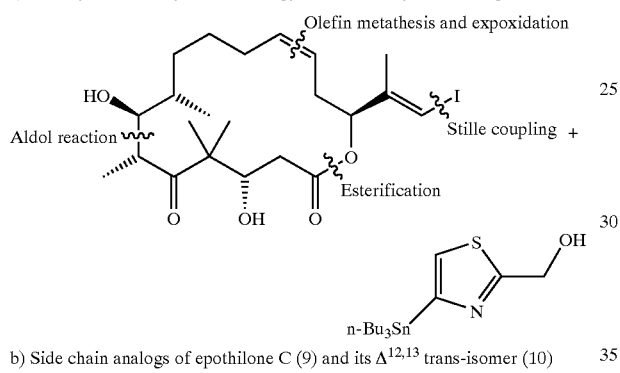

b) Side chain analogs of epothilone C (9) and its $\Delta^{12,13}$ trans-isomer (10)

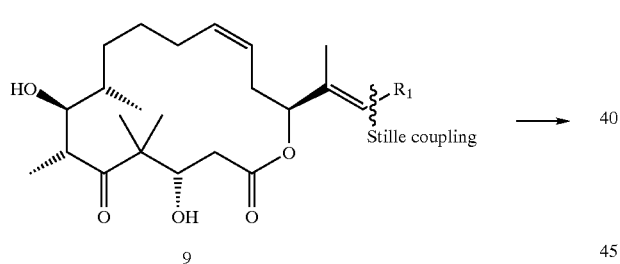

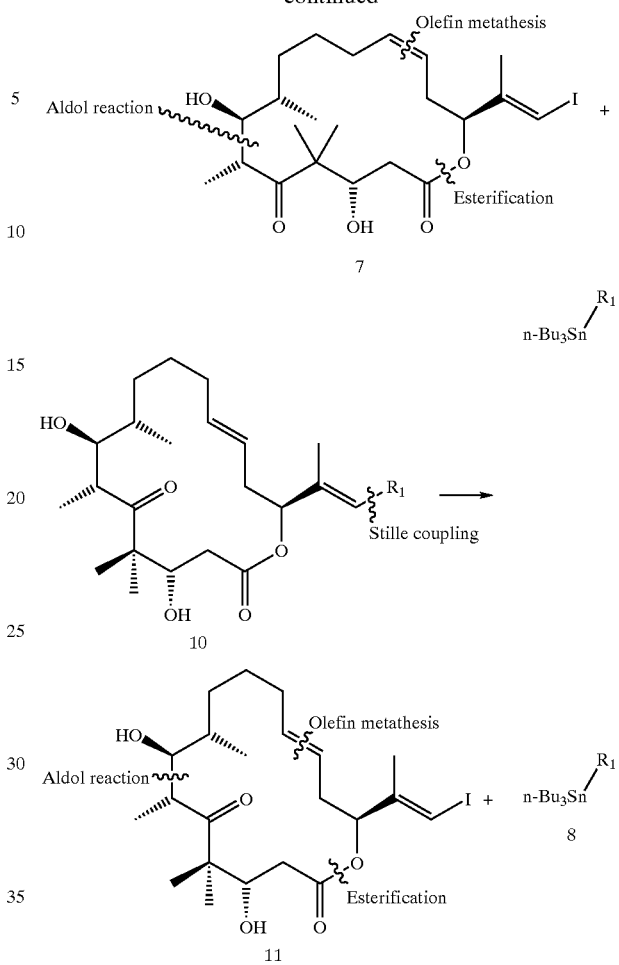

The chemical synthesis of the requisite vinyl iodides 7 and 11 is delineated in PCT application WO 98/25929.

The stannane coupling partners used in the Stille reaction are shown in Scheme 3.

Scheme 3

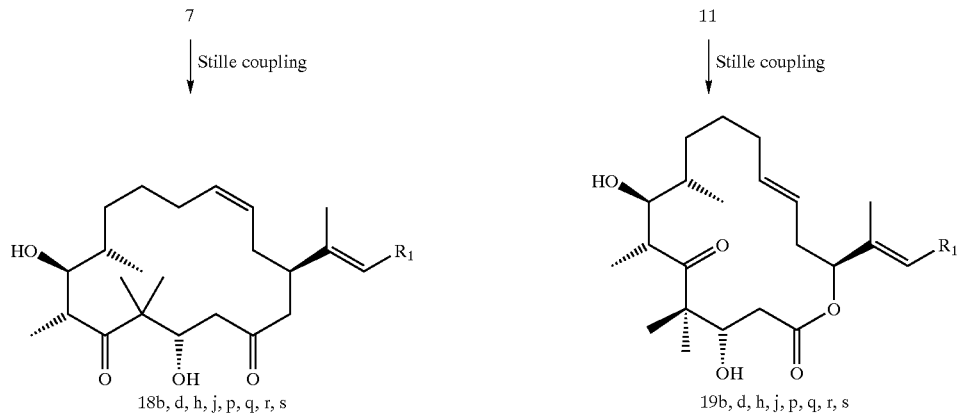

-continued

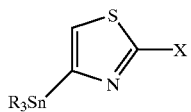

8b: X = SMe, R = Me
8d: X = OEt, R = n-butyl
8p: X = OMe, R = Me

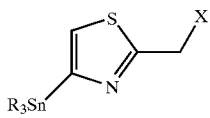

8h: X = OH, R = n-butyl
8j: X = F, R = n-butyl

Stille coupling: Procedure A: 2.0 equiv. of 8, 5–10 mol % Pd(PPh$_3$)$_4$, toluene, 90–100° C., 15–40 min, 39–88%; procedure B: 2.0–2.2 equiv. of 8, 20–30 mol % Pd(MeCN)$_2$Cl$_2$, DMF, 25° C., 12–33 h, 49–94%.

The coupling partners 8b, 8d, 8h and 8j and additional stannanes 8p–r are prepared from readily accessible 2,4-dibromothiazole (20) via monobromides 21 as outlined in Schemes 4 and 5.

Preparation of A) stannanes 8b, 8d and 8p. Reagents and conditions: (b) 3.0 equiv. of NaSMe, EtOH, 25° C., 2 h, 92%; (d) 13 equiv. NaOH, EtOH, 25° C., 30 h, 91%; (e) 13 equiv. NaOH, MeOH, 25° C., 16 h, 82%; (f) 5–10 equiv. of Me$_3$SnSnMe$_3$, 5–10 mol % of Pd(PPh$_3$)$_4$, toluene, 80–100° C., 0.5–3 h, 81–100%; (g) 1.1 equiv. of n-BuLi, 1.2 equiv. of n-Bu$_3$SnCl, −78 to 25° C., 30 min, 98%;

Scheme 5

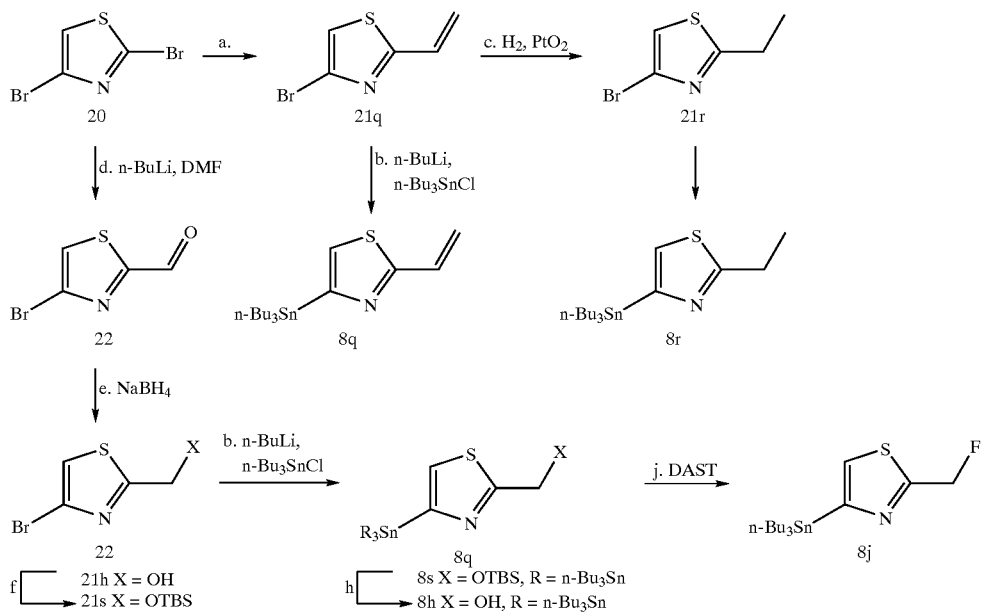

Scheme 4

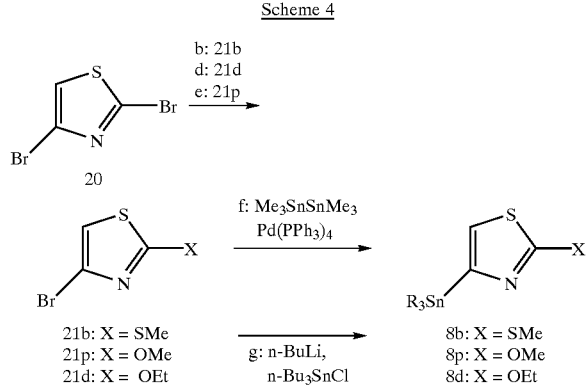

Preparation of stannanes 8h, 8j and 8q–s. Reagents and conditions: (a) 1.05 equiv. n-Bu$_3$SnCH=CH$_2$, toluene, 100° C., 21 h, 83%; (b) 1.1–1.2 equiv. of n-BuLi, 1.2–1.25 equiv. of n-Bu$_3$SnCl, −78 to 25° C., 1 h, 28–85%; (c) H$_2$, 0.15 equiv. of PtO$_2$, EtOH, 25° C., 4 h; 84%; (d) 1.2 equiv. of n-BuLi, 2.0 equiv. of DMF, −78 to 25° C., 2 h; (e) 1.9 equiv. of NaBH$_4$, MeOH, 25° C., 30 min, 63% for two steps; (f) 1.3 equiv. of TBSCI, 2.0 equiv. of imidazole, CH$_2$Cl$_2$, 25° C., 0.5 h, 96%; (h) 1.2 equiv. of TBAF, THF, 25° C., 20 min, 95%; (j) 1.1 equiv. of DAST, CH$_2$Cl$_2$, −78 to 25° C., 10 min, 57%. DAST=diethylamino sulfurtrifluoride.

Sulfide 21b is obtained in 92% yield by replacing the 2-bromo substituent of 20 with the thiomethyl moiety using sodium thiomethoxide (EtOH, 25° C.). The ethoxy and methoxy thiazoles 21d and 21p are prepared by treating dibromide 20 with NaOH in ethanol and methanol, respectively. Bromides (21b, 21d and 21p) are then transformed to the desired trimethylstannanes (8b, p) with hexamethylditin under palladium catalyzed conditions [Pd(PPh$_3$)$_4$, toluene, 80–100° C.], whereas tri-n-butylstannane 8d is obtained from ethoxy-bromide 21d by halogen-metal exchange (n-BuLi, Et$_2$O, −78° C.) and subsequent trapping with tri-n-butyltin chloride in 98% yield.

The synthesis of stannanes (8h, 8j 8q–r) is also achieved from the common precursor 20 (Scheme 5). Thus, palladium catalyzed alkenylation [n-Bu$_3$SnCH=CH$_2$, Pd(PPh$_3$)$_4$, toluene, 100° C.] of 2,4-dibromothiazole 20 affords monobromide 21q, which undergoes halogen-metal exchange (n-BuLi, Et$_2$O, −78° C.) and subsequent quenching with tri-n-butyltin chloride to furnish the desired stannane 8q. Reduction of the intermediate vinyl bromide 21q (H$_2$, PtO$_2$, EtOH, 25° C.) provides access to ethyl thiazole 21r, which is converted into stannane 8r in an identical manner to that described for 8q. The synthesis of stannanes 8h and 8j is achieved via the key hydroxymethyl thiazole 21h.

As shown in Scheme 5, this alcohol is, itself, obtained from dibromide 20 in a two-step process involving lithiation (n-BuLi, Et$_2$O, −78° C.) and subsequent quenching with DMF to give intermediate aldehyde 22, which is then reduced (NaBH$_4$, MeOH, 25° C.) to furnish the desired alcohol 21h in 63% overall yield. Conversion of 21h into stannane 8h requires a three-step sequence involving protection of the hydroxyl group (TBSCI, imidazole, CH$_2$Cl$_2$, 96%), stannylation (i. n-BuLi, Et$_2$O, −78° C.; ii. n-Bu$_3$SnCl, 85%) and subsequent deprotection (TBAF, THF, 25° C., 95%). Fluorination of the resulting stannane 8h (DAST, CH$_2$Cl$_2$, −78° C.) provides direct access to stannane 8j in 57% yield.

With the necessary components in hand, the critical Stille couplings are investigated. Two alternative sets of reaction conditions prove adequate (Scheme 3). Procedure A involves heating a toluene solution of the desired vinyl iodide (7 or 11) with the appropriate stannane 8 in the presence of catalytic amounts of Pd(PPh$_3$)$_4$ at 80–100° C. for between 15 and 40 min. This protocol is used to couple stannanes 8b and 8h. The remaining stannanes, 8d and 8j are coupled using an alternative, milder method, procedure B, in which a mixture of vinyl iodide (7 or 11) and stannane 8 in DMF is treated with PdCl$_2$(MeCN)$_2$ at 25° C.

The coupling of vinyl iodide 7 and stannane 8h provides macrolactone 18h which serves as the precursor to the natural epothilone E (3) (Scheme 6a).

Scheme 6a

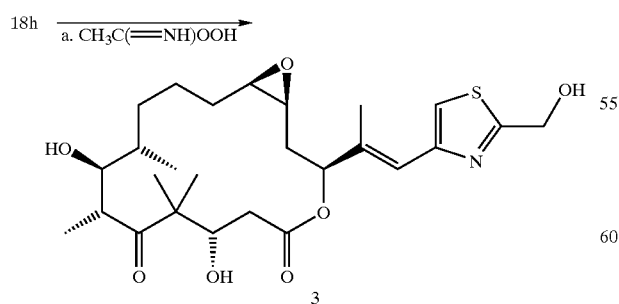

Preparation of epoxide 3. Reagents and conditions: (a) 30 equiv. of H$_2$O$_2$, 60 equiv. of CH$_3$CN, 10 equiv. of KHCO$_3$, MeOH, 25° C., 6 h, 66% (based on 50% conversion).

The total synthesis is completed by epoxidation with in situ generated methylperoxycarboximidic acid (H$_2$O$_2$, KHCO$_3$, MeCN, MeOH, 25° C.; Chaudhuri et al. J. J. Org. Chem. 1982, 47, 5196–5198) furnishing epothilone E (3) (66% based on 50% conversion), which exhibits identical physical characteristics ($^1$H NMR, [α]$_D$) to those published in the art.

The Stille coupling approach is then extended to provide easy access to a variety of side-chain modified analogs of epothilone B (2), both at C-26 and the side chain. The retrosynthetic analysis of epothilone analogs possessing these dual modifications is shown in Scheme 6b and requires the preparation of the crucial vinyl iodide core fragment 24. A macrolactonization strategy similar to that used in our synthesis of epothilone B and a variety of epothilone analogs is thought to be most suitable for this task.

Scheme 6b

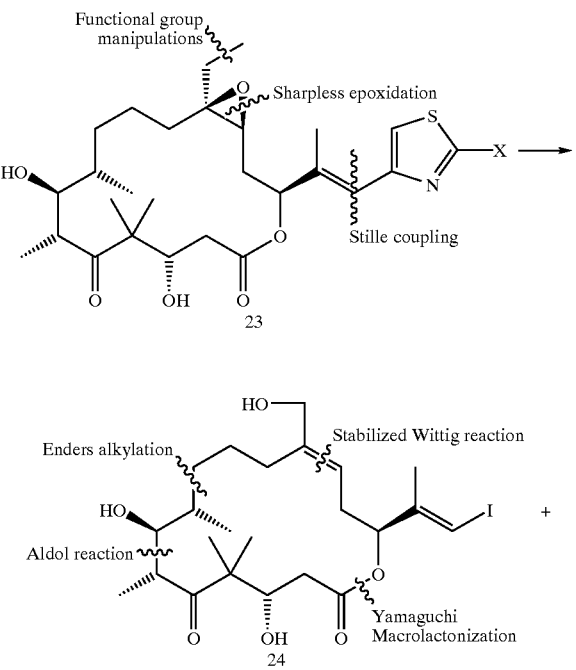

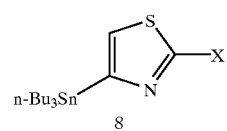

Illustration of a retrosynthetic analysis of epothilone analogs possessing modified C26 and side-chain moieties.

The synthesis begins from the vinyl iodide 13 (Scheme 7) used in the preparation of epothilone E and related analogs (Scheme 3).

Scheme 7

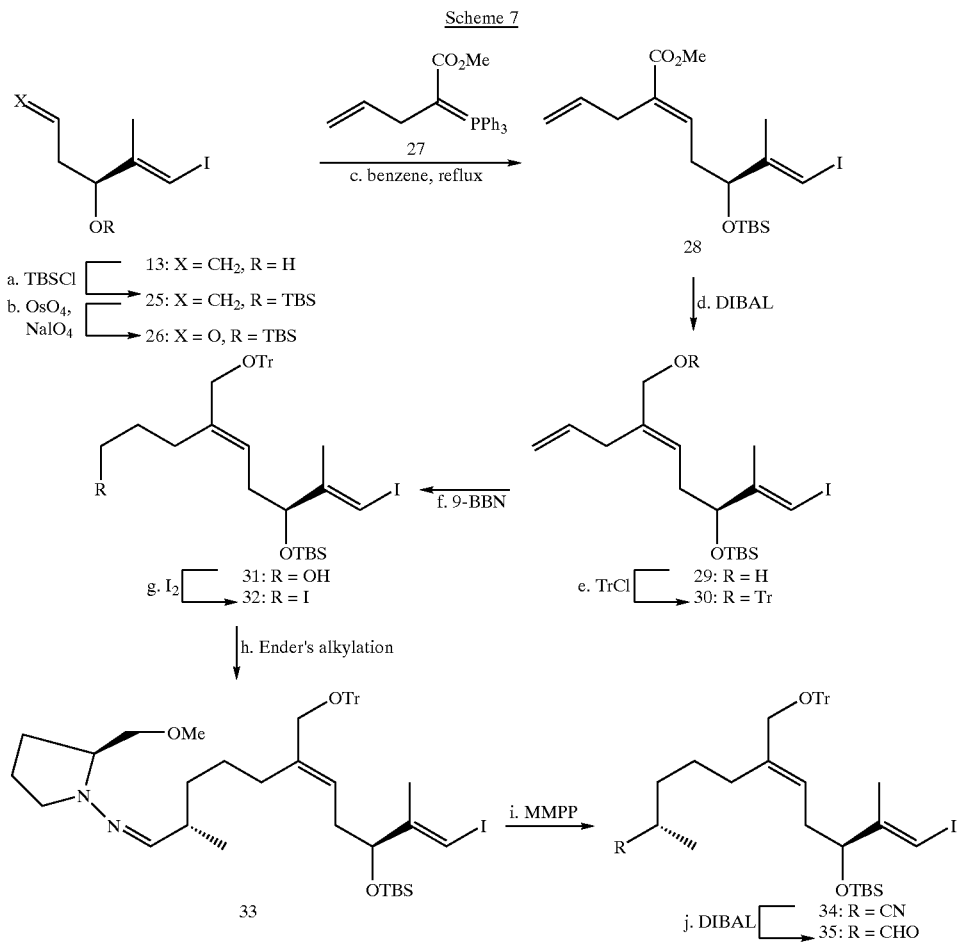

Stereoselective synthesis of aldehyde 35. Reagents and conditions: (a) 1.7 equiv. TBSCl, 2.8 equiv. imidazole, DMF, 0 to 25° C., 7 h, 84%; (b) i. 1.0 mol % OsO$_4$, 1.1 equiv. NMO, THF:t-BuOH:H$_2$O (5:5:1), 0 to 25° C., 13 h, 89%; ii. 6.0 equiv. NaIO$_4$, MeOH:H$_2$O (2:1), 0° C., 30 min, 92%; (c) 2.4 equiv. 27, benzene, reflux, 1.2 h, 98%; (d) 3.0 equiv. DIBAL, THF, −78° C., 2.5 h, 100%. (e) 1.4 equiv. of TrCl, 1.7 equiv. of 4-DMAP, DMF, 80° C., 21 h, 95%; (f) 1.4 equiv. of 9-BBN, THF, 0° C., 9 h; then 3 N aqueous NaOH and 30% H$_2$O$_2$, 0° C., 1 h, 95%; (g) 2.6 equiv. of I$_2$, 5.0 equiv. of imidazole, 2.5 equiv. of Ph$_3$P, Et$_2$O:MeCN (3:1), 0° C., 45 min, 97%; (h) 1.3 equiv. of the SAMP hydrazone of propionaldehyde, 1.4 equiv. of LDA, THF, 0° C., 16 h; then −100° C. and add 1.0 equiv. of 32 in THF, −100 to −20° C., 20 h, 71%; (i) 2.5 equiv. of MMPP, MeOH:phosphate buffer pH 7 (1:1), 0° C., 3.5 h, 89%; (j) 3.0 equiv. of DIBAL, toluene, −78° C., 1 h, 88%. 9-BBN=9-borabicyclo[3.3.1]nonane; DIBAL=diisobutylaiuminium hydride; 4-DMAP=4-dimethylaminopyridine; LDA=lithium diisopropylamide; NMO=4-methylmorpholine N-oxide; SAMP=(S)-(−)-1-amino-2-(methoxymethyl)pyrrolidine; MMPP=monoperoxyphthalic acid, magnesium salt.

Protection of the allylic hydroxyl group (TBSCI, imidazole, DMF, 0 to 25° C.) affords silyl ether 25 (84%) which is transformed into aldehyde 26 by a two-step dihydroxylation-glycol-cleavage sequence (OsO$_4$, NMO, THF/t-BuOH/H$_2$O, 0 to 25° C.; then NaIO$_4$, MeOH/H$_2$O, 0° C., 82% for two steps). A stereocontrolled Wittig reaction with the stabilized ylide 27 (benzene, reflux; Marshall et al. J. Org. Chem. 1986, 51, 1735–1741; Bestmann et al. Angew. Chem. Int. Ed. Engl. 1965, 4, 645–660.) affords ester 28 as a single geometrical isomer in 98% yield. Reduction of the latter compound (DIBAL, THF, −78° C.) affords alcohol 29, which is protected as the triphenylmethyl (trityl) derivative 30 (TrCl, 4-DMAP, DMF, 70° C., 95%).

Elaboration of the terminal olefin is then achieved by selective hydroboration-oxidation to give alcohol 31 (9-BBN, THF, 0° C.; then NaOH, H$_2$O$_2$, 0° C.) which is transformed further into diiodide 32 (I$_2$, imidazole, Ph$_3$P, 0° C.) in 92% overall yield. Introduction of the C8 stereocenter is then achieved using an Ender's alkylation protocol (SAMP hydrazone of propionaldehyde, LDA, THF, 0° C.; then −100° C. and add 32 in THF; Enders et al. Asymmetric Synthesis 1984; Morrison, J. D., Ed.; Academic Press, Orlando, Vol 3, p. 275–339; we thank Prof. Enders for a generous gift of SAMP) resulting in the formation of SAMP hydrazone 33 in 71% yield. Conversion to nitrile 34 (MMPP, MeOH/phosphate buffer pH 7, 0° C., 89%) and ensuing reduction (DIBAL, toluene, −78° C.) afford the desired aldehyde 35 in 88% yield.

The transformation of aldehyde 35 into the desired epothilone macrocyclic core 24 is summarized in Scheme 8.

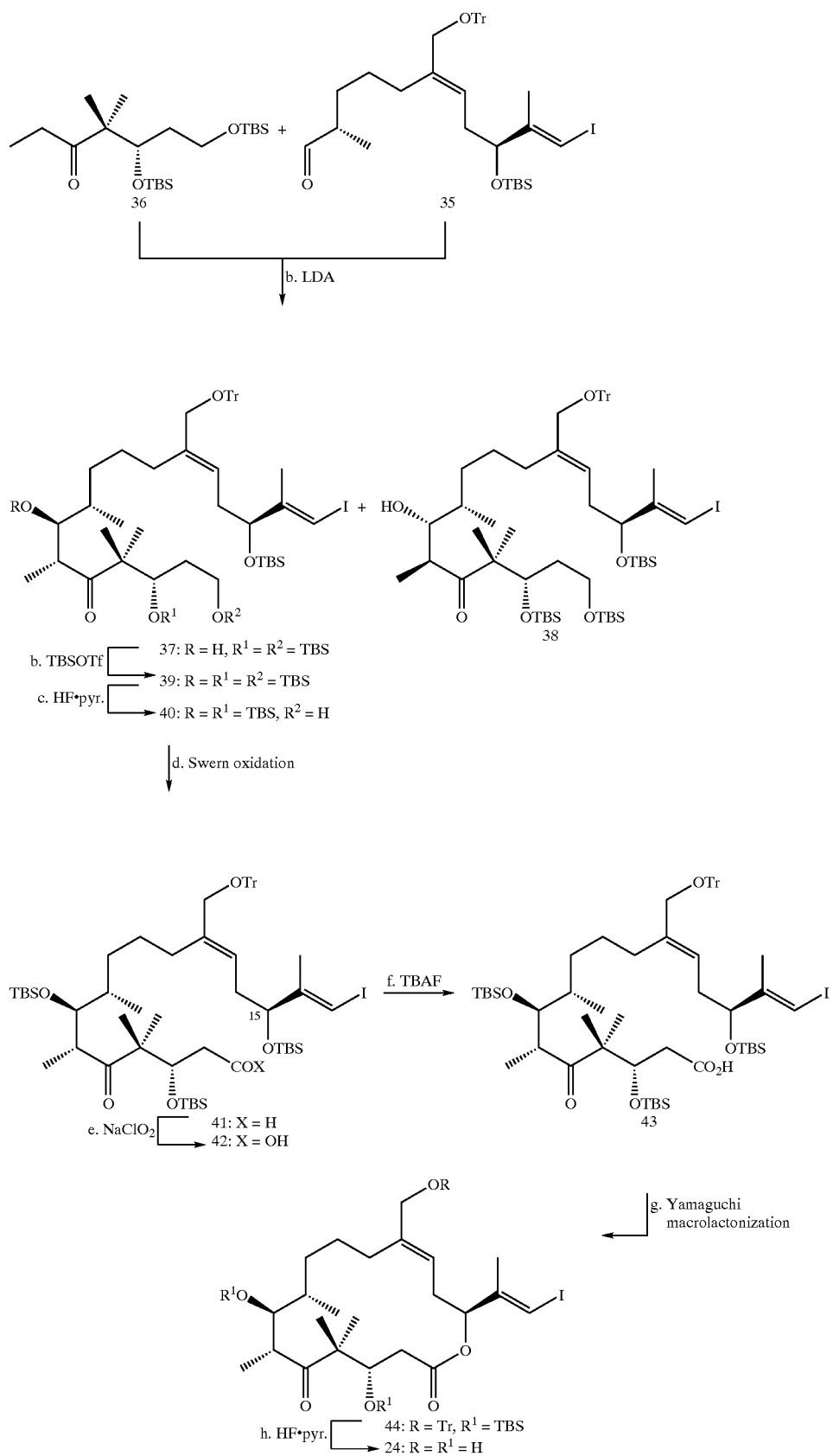

Stereoselective synthesis of vinyl iodide 24. Reagents and conditions: (a) 1.45 equiv. of LDA, THF, −78° C., then 1.4 equiv. of 36 in THF, −78° C., 1.5 h then; −40° C., 0.5 h; then 1.0 equiv. of 35 in THF at −78° C. (66% combined yield, ca. 1.5:1 ratio of 37:38); (b) 3.2 equiv. of TBSOTf, 4.3 equiv. of 2,6-lutidine, $CH_2Cl_2$, −20 to 0° C., 2.5 h, 90%; (c) HF.pyr. in pyridine, THF, 0° C., 3 h, 84%; (d) 2.0 equiv. of $(COCl)_2$, 4.0 equiv. of DMSO, 6.0 equiv. of $Et_3N$, $CH_2Cl_2$, −78 to 0° C., 1.5 h, 98%; (e) 5.0 equiv. of $NaClO_2$, 75 equiv. of 2-methyl-2-butene, 2.5 equiv. of $NaH_2PO_4$, t-BuOH:$H_2O$ (4.5:1), 25° C., 40 min, 100%; (f) 6.0 equiv. of TBAF, THF, 0 to 25° C., 19 h, 95%; (g) 6.0 equiv. of $Et_3N$, 2.4 equiv. of 2,4,6-trichlorobenzoylchloride, THF, 0° C., 1.5 h; then add to a solution of 2.2 equiv. of 4-DMAP in toluene (0.005 M based on 43), 75° C., 2.5 h, 84%; (h) 25% v/v HF.pyr. in THF 0 to 25° C., 15 h, 86%. TBAF=tetra n-butylammonium fluoride.

Aldol reaction of ketone 36, previously used in our synthesis of epothilone B and related analogs (LDA, THF, −78 to −40° C.) and aldehyde 35, affords alcohols 37 and 38 in 66% overall yield, with modest selectivity for the desired 6R,7S diastereoisomer (37). Separation and silylation (TBSOTf, 2,6-lutidine, $CH_2Cl_2$, −20 to 0° C.) of the correct aldol product 37 provides tris-silyl ether 39 in 90% yield.

Selective removal of the primary silyl ether protecting group (HF.pyr. in pyridine/THF, 0° C.) affords alcohol 40 (84%), which is oxidized to acid 42 via aldehyde 41 by a two-step procedure [Swern; then $NaClO_2$, 2-methyl-2-butene, $NaH_2PO_4$, t-BuOH/$H_2O$, 25° C., 98% for two steps). Removal of the C15 silicon protecting group (TBAF, THF, 0 to 25° C.) provides hydroxy-acid 43 (95%) and lays the foundation for the macrolactonization process. This key step is achieved under Yamaguchi conditions (2,4,6-trichlorobenzoylchloride, $Et_3N$, THF; then add to a solution of 4-DMAP in toluene, 0.005M, 75° C.; Inanaga et al. Bull. Chem. Soc. Jpn. 1979, 52, 1989; Mulzer et al. Synthesis 1992, 215–228; Nicolaou et al. Chem. Eur. J. 1996, 2, 847–868) to give the protected epothilone core 44 in 84% yield. Global deprotection (HF.pyr., THF, 0 to 25° C., 86%) completes the synthesis of the key vinyl iodide intermediate 24.

With intermediate 24 in hand, the Stille coupling protocol is then employed to attach the desired heterocyclic moiety. The mild procedure B, employing $PdCl_2(MeCN)_2$ is originally thought to be the most practical and efficient process and is utilized in the preparation of C26 hydroxy epothilones 45–48 (Scheme 9) from the vinyl iodide 24 and the appropriate stannanes 8 (see Schemes 4 and 5).

Scheme 9

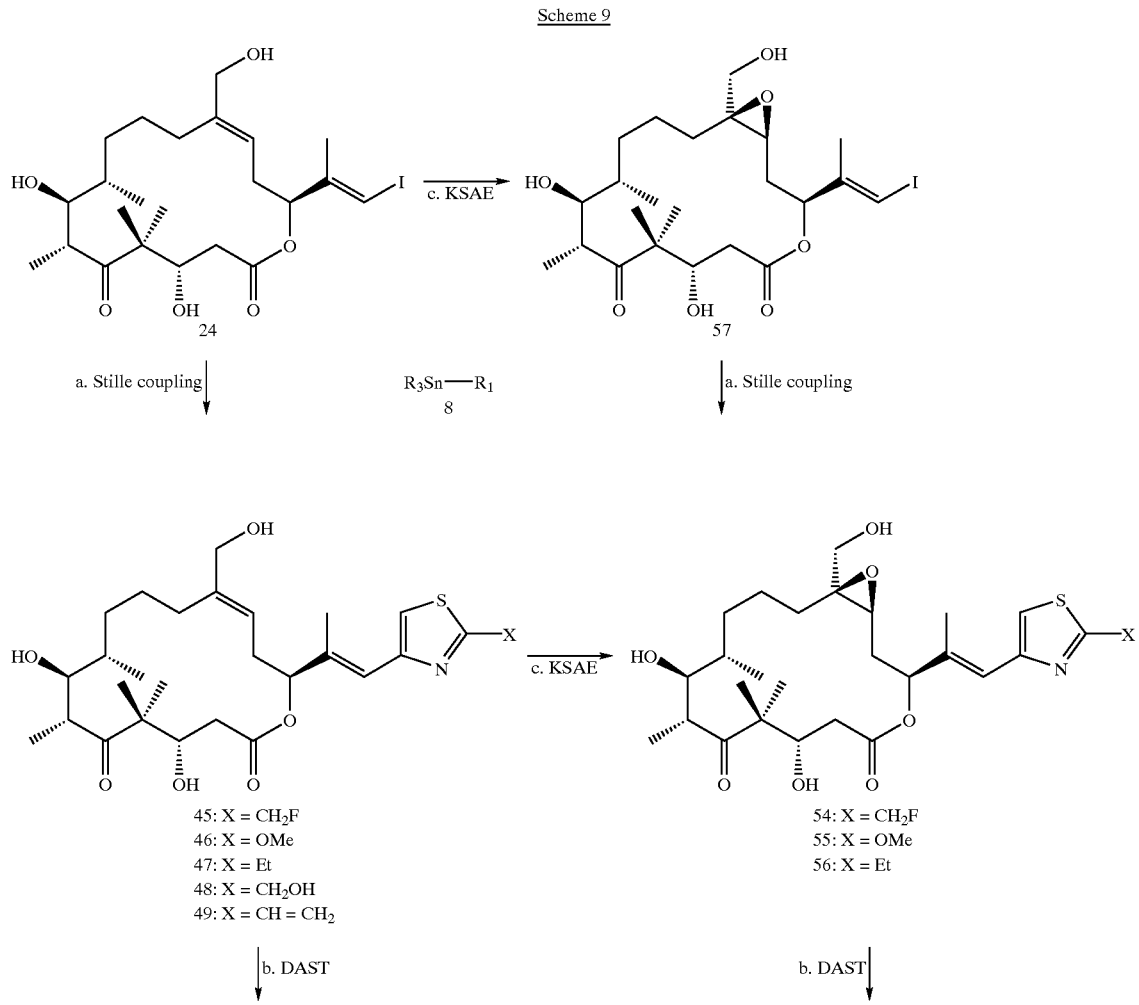

45: X = $CH_2F$
46: X = OMe
47: X = Et
48: X = $CH_2OH$
49: X = CH = $CH_2$

54: X = $CH_2F$
55: X = OMe
56: X = Et

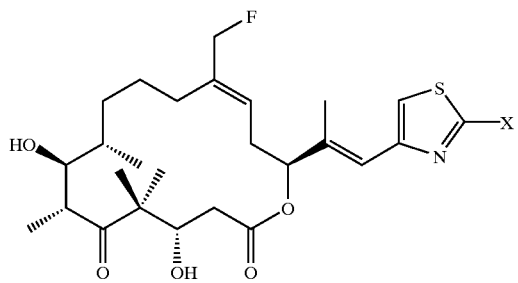

50: X = CH₂F
51: X = OMe
52: X = Et
53: X = CH = CH₂

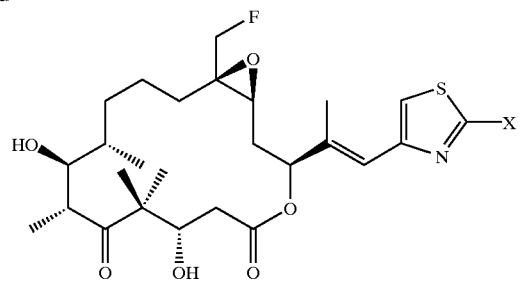

58: X = CH₂F
59: X = OMe

Synthesis of epothilone analogs 54–56 and 58, 59 and desoxyepothilones 45–49 and 50–53. Reagents and conditions: (a) procedure A: 1.7 equiv. of 8, 13 mol % Pd(PPh₃)₄, toluene, 100° C., 2 h, 15%; procedure B: 1.5–2.0 equiv. of 8, 10–20 mol % Pd(MeCN)₂Cl₂, DMF, 25° C., 15–33 h, 41–56%; (b) 1.05–1.4 equiv. of DAST, CH₂Cl₂, −78° C., 10 min, 26–58%; (c) 0.5 equiv. (+)-DET, 0.5 equiv. Ti(i-PrO)₄, 2.2 equiv. of t-BuOOH, −40° C., CH₂Cl₂, 4Å molecular sieves, 1–2 h, 52–89%. DET=diethyl tartrate.

Unfortunately, these conditions are not suitable for the coupling of 24 and vinyl stannane 8q (see Scheme 5). Recourse to the alternative procedure A provides access to the desired epothilone 49, albeit, in poor yield.

The presence of the C26 hydroxy functionality provides a convenient handle for further elaboration of the epothilone products. For example, the C26 alcohols 45–47 and 49 are treated with DAST (CH₂Cl₂, −78° C.) to furnish fluorinated epothilone analogs 50–53 in moderate yields as shown in Scheme 9. Alternatively, asymmetric epoxidation of substrates 45 and 46 under Katsuki-Sharpless conditions [(+)-DET, Ti(i-PrO)₄, t-BuOOH, 4 Å molecular sieves, CH₂Cl₂, −40° C.; Katsuki, T.; Sharpless, K. B. J. Am. Chem. Soc. 1980, 102, 5976–5978] affords epothilones 54 and 55, respectively. Subsequent treatment with DAST (CH₂Cl₂, −78° C.) provides additional analogs 58 and 59, again in moderate yield. At this juncture, a more efficient approach to epoxides such as 54 and 55 is envisaged in which asymmetric epoxidation of vinyl iodide 24 is achieved to give a common intermediate, which then serves as a substrate for the Stille coupling. Despite initial reservations concerning the compatibility of the epoxide functionality with the Stille conditions, the epoxide 57 required for this approach is prepared from olefin 24 in 81% yield as described for the synthesis of 45 and 46. To our pleasant surprise, application of the standard coupling procedure B, using stannane 8r, results in the successful preparation of epothilone analog 56 (73% yield based on 70% conversion).

The success of the Stille coupling strategy on substrates possessing an epoxide moiety indicates that epothilones 66–68 can be accessed from a common intermediate 65 as outlined in Scheme 10.

Scheme 10

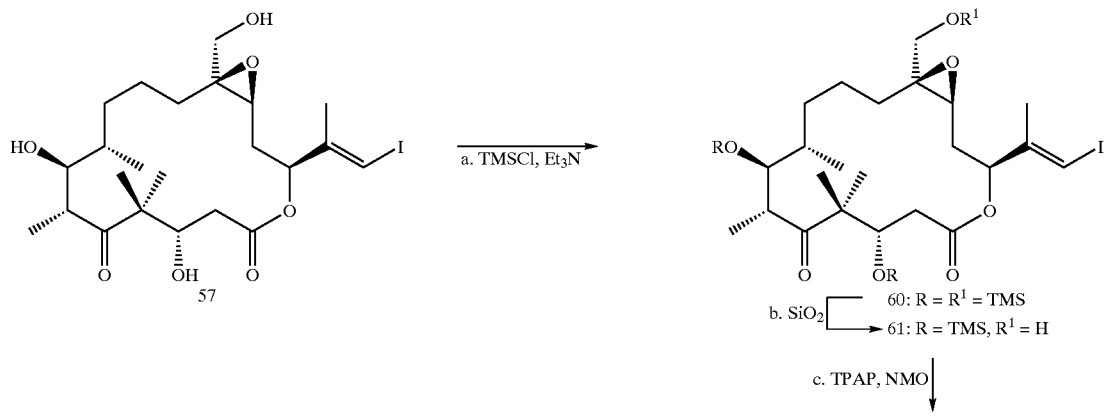

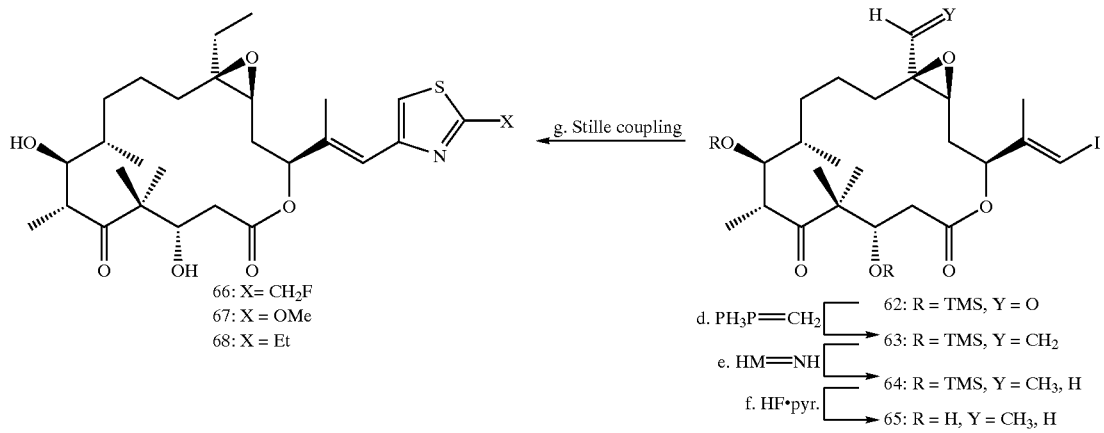

66: X= CH$_2$F
67: X = OMe
68: X = Et g. Stille coupling d. PH$_3$P=CH$_2$
  62: R = TMS, Y = O
  63: R = TMS, Y = CH$_2$
e. HM=NH
  64: R = TMS, Y = CH$_3$, H
f. HF·pyr.
  65: R = H, Y = CH$_3$, H Synthesis of C26-substituted epothilones 66–68. Reagents and conditions: (a) 15 equiv. of Et$_3$N, 8.0 equiv. TMSCl, DMF, 25° C., 12 h; (b) silica gel, CH$_2$Cl$_2$, 25° C., 12 h, 98% for two steps; (c) 3.0 equiv. of NMO, 10 mol % TPAP, CH$_2$Cl$_2$, 25° C., 40 min, 90%; (d) 9.7 equiv. of Ph$_3$P$^+$CH$_3$Br$^-$ mixture with NaNH$_2$), THF, −5° C., 65% (e) 25 equiv. of H$_2$NNH$_2$, 16 equiv. of H$_2$O$_2$, EtOH, 0°, 3 h; (f) HF.pyr. pyridine in THF, 0 to 25° C., 2 h, 75% for two step; (g) 1.7–2.3 equiv. of 8, 0.2–0.3 mol % Pd(MeCN)$_2$Cl$_2$, DMF, 25° C., 15–23 h, 52–79%. TPAP = tetrapropylammonium perruthenate.

Preparation of the desired template (65) is achieved by a five-step sequence, which starts with global protection of triol 57 (TMSCl, Et$_3$N, DMF, 25° C.). Selective deprotection, using silica gel (CH$_2$Cl$_2$, 25° C., 98% for two steps), reveals the C26 primary hydroxyl functionality which is then oxidized (TPAP, NMO, 4 Å molecular sieves, CH$_2$Cl$_2$, 25° C.) to furnish aldehyde 62 in 90% yeild. Methylenation using methyl triphenylphosphonium bromide (Schlosser's "instant ylid" mix, THF, −5° C.; Schlosser, M.; Schaub, B. Chimia 1982, 36, 3965) furnishes olefin 63 (65%) which undergoes reduction with in situ generated diimide (H$_2$NNH$_2$, H$_2$O$_2$, EtOH, 0° C.) to give intermediate 64. Deprotection of the remaining silyl ethers (HF.pyridine (=pyr.). in pyridine/THF, 0° C.) affords the desired vinyl iodide 65 in 75% yield for two steps. The Stille coupling procedure B described above is then used to access epothilones 66–68 in moderate yields (Scheme 10).

The chemistry described in this example relies on a Stille coupling approach to construct a series of epothilone analogs with diversity at the side-chain or at both the side-chain and C26 site from a common macrocyclic intermediate.

EXAMPLE 4

Formulae of Compounds According to the Invention

TABLE

Formulae of compounds according to the invention:

| Entry | Compound |
|---|---|
| 1 | 18h: X = OH |
| 2 | (Formula: see under entry 1)<br>18j: X = OH |
| 3 | 18d: X = OEt |
| 4 | (Formula: see under entry 3)<br>18b: X = SMe |

TABLE-continued

Formulae of compounds according to the invention:

| Entry | Compound |
|---|---|
| 5 | [structure] 19h: X = OH |
| 6 | (Formula: see under entry 5) 19j: X = F |
| 7 | [structure] 19d: X = OEt |
| 8 | (Formula: see under entry 7) 19b: X = SMe |
| 9 | [structure] 45: X = CH$_2$F |
| 10 | (Formula: see under entry 9) 46: X = OMe |
| 11 | (Formula: see under entry 9) 47: X = CH$_2$CH$_3$ |
| 12 | (Formula: see under entry 9) 48: X = CH$_2$OH |
| 13 | (Formula: see under entry 9) 49: X = CH=CH$_2$ |
| 14 | [structure] 50: X = CH$_2$F |
| 15 | (Formula: see under entry 14) 51: X = OMe |
| 16 | (Formula: see under entry 14) 52: X = CH=CH$_2$ |
| 17 | (Formula: see under entry 14) 53: X = CH$_2$CH$_3$ |
| 18 | [structure] 54: X = CH$_2$F |
| 19 | (Formula: see under entry 18) 55: X = OMe |
| 20 | (Formula: see under entry 18) 56: X = CH$_2$CH$_3$ |
| 21 | [structure] 58: X = CH$_2$F |
| 22 | (Formula: See under entry 21) 59: X = OMe |

TABLE-continued

Formulae of compounds according to the invention:

| Entry | Compound |
|---|---|
| 23 | [structure shown]<br>66: X = CH$_2$F |
| 24 | (Formula: see under entry 23)<br>67: X = OMe |
| 25 | (Formula: see under entry 23)<br>68: X = CH$_2$CH$_3$ |
| 26 | epothilone A |

EXAMPLE 5

Biological Results

In accordance with the methods described above (inhibition of tubulin depolymerization by a compound of the formula I is measured using pig brain microtubuli, comparison with 25 μM epothilone B; cellular assays are analogous to those described above for KB-31 cells), the results given in the following table are obtained for the mentioned compounds of formula I:

| Compound | Tubulin[a] (%) | KB-31[b] IC50 [nM] | KB-8511[c] IC50 [nM] | A549[d] IC50 [nM] | HCT-15[e] IC50 [nM] | HCT-116[e] IC50 [nM] |
|---|---|---|---|---|---|---|
| D (Example 1) | 88.9 | 0.108 | 0.105 | 0.17 | 0.247 | 0.209 |
| Example 2C | 89.9 | 0.153 | 0.163 | 0.24 | 0.298 | 0.373 |

[a]Induction of tubulin polymerisation at 5 μM concentration of test compound versus epothilone B at 25 μM (in %).
[b]epidermoid
[c]epidermoid (P-gp overexpressing)
[d]lung
[e]colon

| Compound | DU145[f] IC50 [nM] | PC-3M[f] IC50 [nM] | MCF-7[g] IC50 [nM] | MCF-7/ADR[h] IC50 [nM] |
|---|---|---|---|---|
| D (Example 1) | 0.252 | 0.361 | 0.114 | 0.853 |
| Example 2B | 0.320 | 0.498 | 0.144 | 1.31 |

[f]prostate
[g]breast
[h]breast (multidrug resistant)

EXAMPLE 6

Further Compounds of the Formula I

In analogy to the methods described above and below, the compounds falling under formula I are prepared that have the following formulae:

EXAMPLE 6 (i)

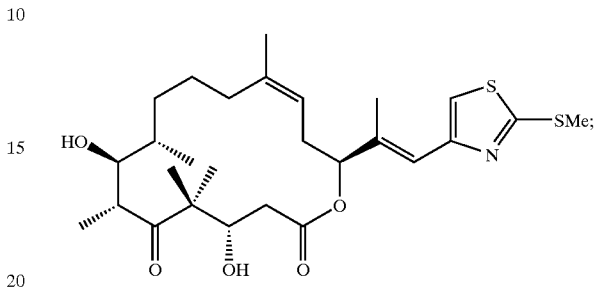

EXAMPLE 6(ii)

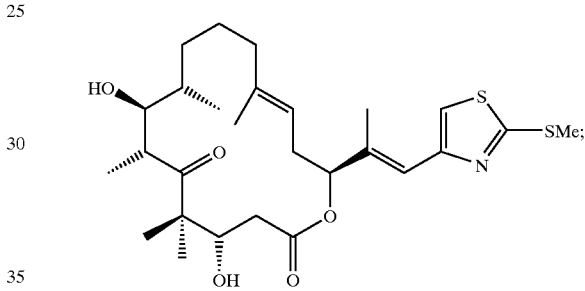

EXAMPLE 6 (iii)

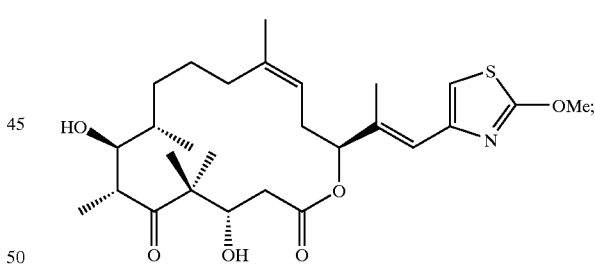

EXAMPLE 6 (iv)

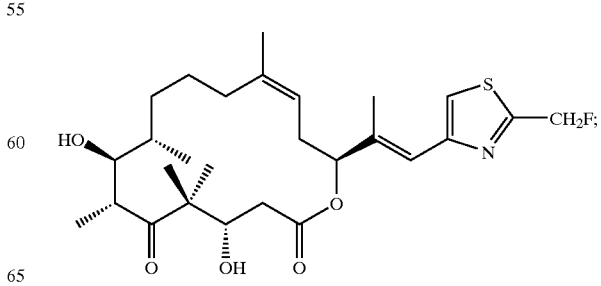

EXAMPLE 6 (v)

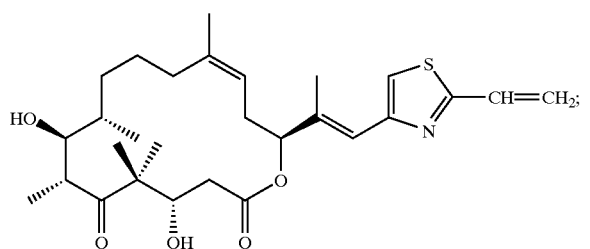

EXAMPLE 6 (vi)

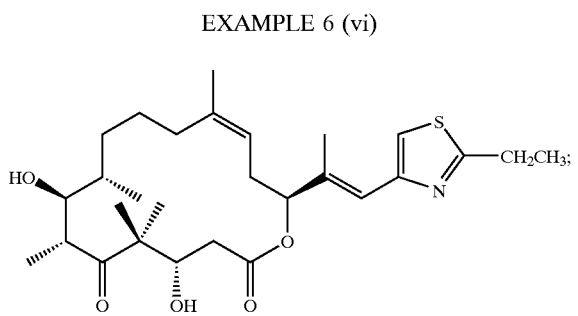

EXAMPLE 6 (vii)

EXAMPLE 6 (viii)

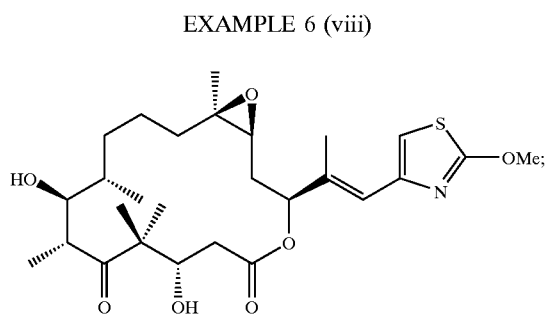

EXAMPLE 6 (ix)

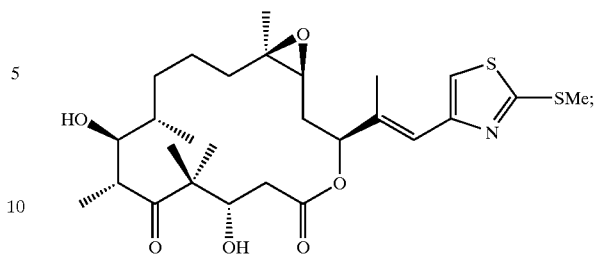

EXAMPLE 6 (x)

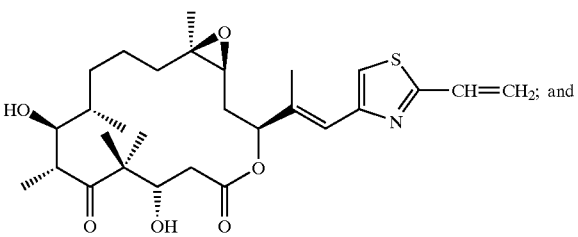

EXAMPLE 6 (xi)

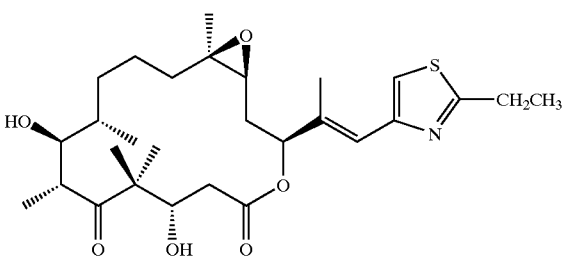

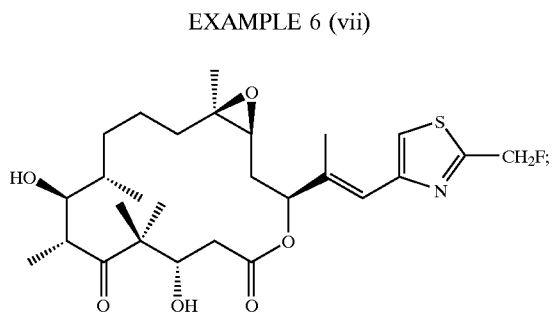

EXAMPLE 6

Pharmaceutical Formulation

Epothilone analogue D (example 1) or the epothilone analogue of Example 2 C) (15 mg) is dissolved in 98–100% propylene glycol (1.0 ml). The solution is sterile filtered through a 0.22 microns pore size filter and charged to 1 ml ampoules. The filled ampoules are used for storage and shipment. Prior to intravenous administration, the contents of an ampoule are added to 250 to 1000 ml of a 5% glucose solution in water-for-injection.

EXAMPLE 7

Use of Additional Stannanes to Synthesize Side Chain Modified Epothilone Analogs as Illustrated in Schemes 11 and 12

Scheme 11

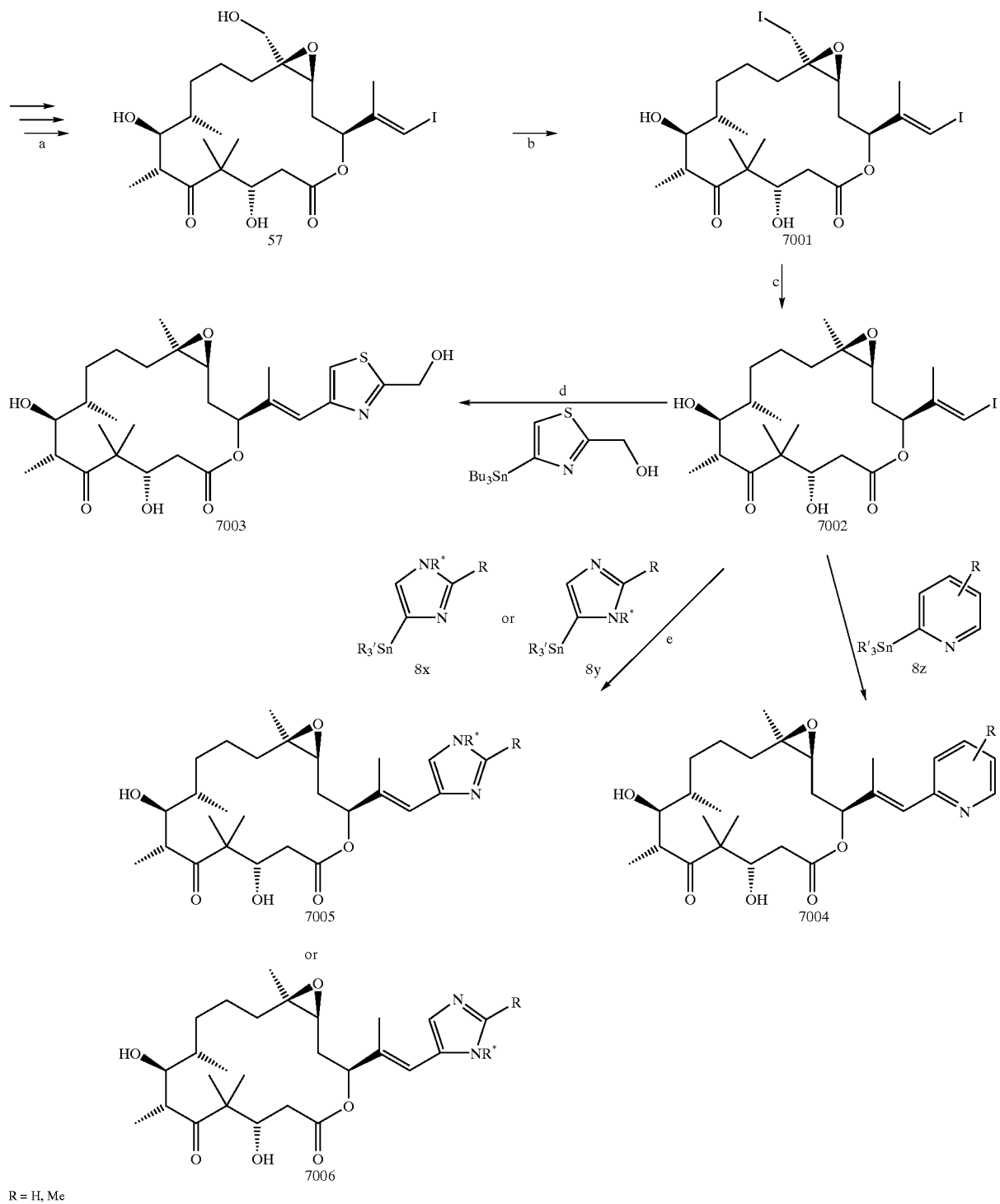

R = H, Me
R* = H, Me or a protecting group, preferably H or Me

General Route to the synthesis of various side-chain modified epothilone B analogs having pyridine and imidazole modifications.

a: as previously described (see Nicolaou et al. *Tetrahedron* 54, 7127–7166 (1998)); b, d, e: conditions as previously described (see above or Nicolaou et al. *Tetrahedron* 54, 7127–7166); c: NaBH$_3$CN, HMPA, 40–45° C.

Protecting groups are those known in the art, especially those described in the standard references mentioned hereinabove, as well as the methods of their introduction and removal mentioned in said standard references.

Preferably, in 7006 R* is H or methyl. in 7004, R is preferably methyl.

Use of the Stille coupling procedure to prepare a number of side chain modified epothilone analogs from the common precursors 57, and 8h, 8x, 8y and 8z is described in Scheme 11 and 12. Synthesis of vinyl iodide 7002 is achieved from the previously reported C26-hydroxy compound and involves conversion of 57 to diiodide 7001 and subsequent reduction using NaBH₃CN: Diiodide 7001 (1 equivalent; from 57) and sodium cyanoborohydride (10 equivalents) are dissolved in anhydrous HMPA (0.2 M) and the resulting mixture heated at 45–50° C. for 48 h. After cooling to room temperature, water is added and the aqueous phase extracted four times with ethyl acetate. The combined organic fractions are dried (Na₂SO₄) and passed through a short plug of silica gel to remove traces of HMPA (eluting with 50% ethyl acetate in hexanes). Following evaporation of solvents, the residue is purified by preparative thin layer chromatography (eluting with 50% ethyl acetate in hexanes) to provide pure vinyl iodide 7002 (84%). Coupling to the epothilone E side chain is achieved and the coupling of a number of pyridines and imidazoles is accomplished via coupling of numerous alternative side chains with the aromatic stannanes as shown in Schemes 11 and 12 using the standard methods outlined herein.

Scheme 12

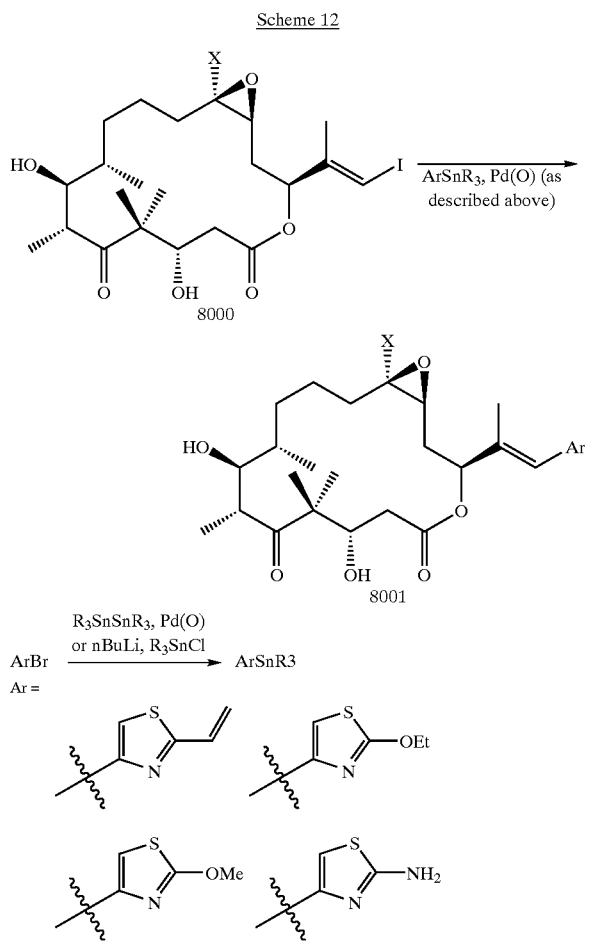

Illustration of some side chain modified epothilone analogs using indicated aryl stannanes (ArSnR₃) from either the metathesis or macrolactonization approach wherein R is n-butyl or methyl. The stannanes are synthesized using standard conditions known in the art. X is a radical selected from the group consisting of hydrogen; lower alkyl, especially methyl, ethyl, n-propyl, iso-propyl, n-butyl, iso-butyl, tert-butyl, n-pentyl, n-hexyl; —CH=CH₂; —C≡CH; —CH₂F; —CH₂Cl; —CH₂—OH; —CH₂—O—(C₁-C₆-alkyl), especially —CH₂—O—CH₃; and —CH₂—S—(C₁-C₆-alkyl), especially —CH₂—S—CH₃; and R is methyl or n-butyl.

Synthetic Protocols

General: All reactions are carried out under an argon atmosphere with dry, freshly distilled solvents under anhydrous conditions, unless otherwise noted. Tetrahydrofuran (THF) and diethyl ether (ether) are distilled from sodium-benzophenone, and dichloromethane (CH₂Cl₂), benzene (PhH), and toluene from calcium hydride. Anhydrous solvents are also obtained by passing them through commercially available activated alumina columns. Yields refer to chromatographically and spectroscopically ($^1$H NMR) homogeneous materials, unless otherwise stated. All solutions used in workup procedures are saturated unless otherwise noted. All reagents are purchased at highest commercial quality and used without further purification unless otherwise stated. All reactions are monitored by thin-layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) is used for flash column chromatography. Preparative thin-layer chromatography separations are carried out on 0.25, 0.50 or 1 mm E. Merck silica gel plates (60F-254). NMR spectra are recorded on Bruker DRX-600, AMX-500, AMX-400 or AC-250 instruments and calibrated using residual undeuterated solvent as an internal reference. The following abbreviations are used to explain the multiplicities: s, singlet; d, doublet; t, triplet; q, quartet; m, multiplet; band, several overlapping signals; b, broad. IR spectra are recorded on a Perkin-Elmer 1600 series FT-IR spectrometer. Optical rotations are recorded on a Perkin-Elmer 241 polarmeter. High resolution mass spectra (HRMS) are recorded on a VG ZAB-ZSE mass spectrometer under fast atom bombardment (FAB) conditions.

cis-Macrolactone diol 7 as illustrated in Scheme 3. To a solution of iodide 16 (305 mg, 0.491 mmol) in THF (8.2 mL, 0.06 M) at 25° C. is added HF.pyr. (2.7 mL) and the resulting solution is stirred at the same temperature for 27 h. The reaction is then quenched by careful addition to a mixture of saturated aqueous NaHCO₃ (100 mL) and EtOAc (100 mL), and the resulting two-phase mixture is stirred at 25° C. for 2 h. The extracts are then separated and the organic layer is washed with saturated aqueous NaHCO₃ (100 mL) and brine (100 mL), and then dried (MgSO₄). Purification by flash column chromatography (silica gel, 20 to 50% EtOAc in hexanes) furnishes diol 7 (208 mg, 84%). R$_f$=0.21 (silica gel, 25% EtOAc in hexanes); $[\alpha]^{22}_D$ −53.1 (c 1.37, CHCl₃); IR (thin film) $\nu_{max}$ 3499 (br), 2930, 1732, 1688, 1469, 1379, 1259, 1149, 1093, 1048, 1006, 732 cm$^{-1}$; $^1$H NMR (500 MHz, CDCl₃) δ6.43 (s, 1 H, ICH=C(CH₃)), 5.44 (ddd, J=10.5, 10.5, 4.5 Hz, 1 H, CH=CHCH₂), 5.34 (dd, J=9.5, 2.0 Hz, 1 H, CHOCO), 5.32 (ddd, J=10.5, 10.5, 5.5 Hz, 1 H, CH=CHCH₂), 4.07 (ddd, J=11.0, 6.0, 3.0 Hz, 1 H, (CH₃)₂CCH(OH)), 3.73 (ddd, J=2.5, 2.5, 2.5 Hz, 1 H, CHOH(CHCH₃)), 3.10 (qd, J=7.0, 2.5 Hz, 1 H, CH₃CH(C=O)), 2.84 (d, J=2.5 Hz, 1 H, CH(CH₃)CHOHCH(CH₃)), 2.66 (ddd, J=15.0, 9.5, 9.5 Hz, 1 H, =CHCH₂CHO), 2.51 (dd, J=15.5, 11.0 Hz, 1 H, CH₂COO), 2.42 (dd, J=15.5, 3.0 Hz, 1 H, CH₂COO), 2.35 (d, J=6.0 Hz, 1 H, (CH₃)₂CHOH), 2.21–2.12 (m, 2 H), 2.05–1.97 (m, 1 H), 1.88 (s, 3 H, ICH=CCH₃), 1.76–1.70 (m, 1 H), 1.70–1.62 (m, 1 H), 1.32 (s, 3 H, C(CH₃)₂), 1.18 (d, J=7.0 Hz, 3 H, CH₃CH(C=O)), 1.10 (s, 3 H, C(CH₃)₂), 1.35–1.05 (m, 3 H), 0.99 (d, J=7.0

Hz, 3 H, CH$_3$CHCH$_2$); HRMS (FAB), calcd. for C$_{22}$H$_{35}$IO$_5$ (M+Cs$^+$) 639.0584, found 639.0557.

trans-Macrolactone diol 11 as illustrated in Scheme 3. A solution of iodide 17 (194 mg, 0.313 mmol) in THF (5.2 mL, 0.06 M) is treated with HF.pyr. (1.7 mL) according to the procedure described for the preparation of diol 7 to afford, after flash column chromatography (silica gel, 20 to 50% EtOAc in hexanes), diol 11 (134 mg, 85%). R$_f$=0.16 (silica gel, 25% EtOAc in hexanes); [α]$^{22}_D$ −20.0 (c 1.15, CHCl$_3$); IR (film) ν$_{max}$ 3478, 2930, 1732, 1693 cm$^{-1}$; $^1$H NMR (500 MHz, CDCl$_3$) δ6.37 (d, J=1.5 Hz, 1 H, ICH═CCH$_3$), 5.35 (ddd, J=14.5, 7.0, 7.0 Hz, 1 H, CH═CHCH$_2$), 5.24 (ddd, J=14.5, 7.0, 7.0 Hz, 1 H, CH═CHCH$_2$), 5.17 (dd, J=6.5, 3.5 Hz, 1 H, CHOCO), 4.41 (dd, J=8.0, 3.5 Hz, 1 H, (CH$_3$)$_2$CCH(OTBS)), 3.85 (bs, 1 H, CHOH(CHCH$_3$)), 3.38 (bs, 1 H, CHOH(CHCH$_3$)), 3.18 (qd, J=7.0, 6.5 Hz, 1 H, CH$_3$CH(C═O)), 2.68–2.34 (m, 4 H), 2.44 (s, 3 H, CH$_3$Ar), 2.19–2.11 (m, 1 H), 1.96 (s, 3 H, CH$_3$C═CH), 1.99–1.93 (m, 1 H), 1.67–1.52 (m, 2 H), 1.48–1.42 (m, 1 H), 1.31–0.99 (m, 2 H), 1.22 (d, J=7.0 Hz, 3 H, CH$_3$CH(C═O)), 1.14 (s, 3 H, C(CH$_3$)$_2$), 1.09 (s, 3 H, C(CH$_3$)$_2$), 1.02 (d, J=7.0 Hz, 3 H, CH$_3$CHCH$_2$), 0.84 (s, 9 H, SiC(CH$_3$)$_3$(CH$_3$)$_2$), 0.08 (s, 3 H, SiC(CH$_3$)$_3$(CH$_3$)$_2$), −0.01 (s, 3 H, SiC(CH$_3$)$_3$(CH$_3$)$_2$); HRMS (FAB), calcd. for C$_{22}$H$_{35}$IO$_5$ (M+Cs$^+$) 639.0584, found 639.0606.

2-Thiomethyl-4-bromothiazole 21b as illustrated in Scheme 4. 2,4-Dibromothiazole 20 (82 mg, 0.34 mmol, 1.0 equiv.) is dissolved in ethanol (2.3 mL, 0.15 M) and treated with sodium thiomethoxide (75 mg, 1.02 mmol, 3.0 equiv.). The reaction mixture is stirred at 25° C. for 2 h, upon which time completion of the reaction is established by $^1$H NMR. The mixture is poured into water (5 mL) and extracted with ether (2×5 mL). The combined organic fractions are dried (MgSO$_4$), the solvents evaporated and the residue purified by flash column chromatography (silica gel, 5% EtOAc in hexanes) to furnish 2-thiomethyl-4-bromothiazole 21b (77 mg, 92%). R$_f$=0.58 (silica gel, 10% EtOAc in hexanes); IR (film) ν$_{max}$ 3118, 2926, 1459, 1430, 1388, 1242, 1040, 966, 876, 818 cm$^{-1}$; $^1$H NMR (500 MHz, CDCl$_3$) δ7.07 (s, 1 H, ArH), 2.69 (s, 3 H, SCH$_3$); GC/MS (EI), calcd. for C$_4$H$_4$BrNS$_2$ (M$^+$) 209/211, found 209/211.

2-Ethoxy-4-bromothiazole 21d as illustrated in Scheme 4. To a solution of 2,4-dibromothiazole 20 (58 mg, 0.239 mmol, 1.0 equiv.) in EtOH (2.4 mL, 0.1 M) is added NaOH (122 mg, 3.05 mmol, 12.8 equiv.) and the resulting solution is stirred at 25° C. until TLC indicates the disappearance of dibromide (ca. 30 h). The resulting yellow solution is then partitioned between ether (10 mL) and saturated aqueous NH$_4$Cl (10 mL) and the layers are separated. The aqueous layer is extracted with ether (10 mL) and the combined organic extracts are washed with brine (20 mL), dried (MgSO$_4$) and concentrated carefully under reduced pressure. Flash column chromatography (silica gel, 17% ether in hexanes) furnishes 2-ethoxy-4-bromothiazole 21d as a volatile oil (45 mg, 91%). R$_f$=0.58 (silica gel, 17% ether in hexanes); IR (film) ν$_{max}$ 3125, 2983, 2936, 2740, 1514, 1480, 1392, 1360, 1277, 1234, 1080, 1018, 897, 823 cm$^{-1}$; $^1$H NMR (500 MHz, CDCl$_3$) δ6.57 (s, 1 H, ArH), 4.48 (q, J=7.0 Hz, 2 H, CH$_3$CH$_2$), 1.43 (t, J=7.0 Hz, 3 H, CH$_3$CH$_2$); GC/MS (EI), calcd. for C$_4$H$_4$BrNSO (M$^+$) 193/195, found 193/195.

2-Methoxy-4-bromothiazole 21p as illustrated in Scheme 4. To a solution of 2,4-dibromothiazole 20 (253 mg, 1.04 mmol, 1.0 equiv.) in MeOH (10.5 mL, 0.1 M) is added NaOH (555 mg, 13.9 mmol, 13.3 equiv.) and the resulting solution is stirred at 25° C. until TLC indicates the disappearance of dibromide (ca. 16 h). The resulting yellow solution is then partitioned between ether (10 mL) and saturated aqueous NH$_4$Cl (10 mL) and the layers are separated. The aqueous phase is extracted with ether (10 mL) and the combined organic extracts are dried (MgSO$_4$) and concentrated carefully under reduced pressure. Flash column chromatography (silica gel, 10% ether in hexanes) furnishes 2-methoxy-4-bromothiazole 21p as a volatile oil (138 mg, 82%). R$_f$=0.56 (silica gel, 17% ether in hexanes); IR (film) ν$_{max}$ 3125, 2952, 2752, 1524, 1520, 1481, 1417, 1277, 1238, 1081, 982, 884, 819 cm$^{-1}$; $^1$H NMR (500 MHz, CDCl$_3$) δ6.58 (s, 1 H, ArH), 4.09 (q, 3 H, CH$_3$); GC/MS (EI), calcd. for C$_5$H$_6$BrNSO (M$^+$) 207/209, found 207/209.

2-Hydroxymethyl-4-bromothiazole 21h as illustrated in Scheme 4. To a solution of 2,4-dibromothiazole 20 (50 mg, 0.206 mmol, 1.0 equiv.) in anhydrous ether (2.0 mL, 0.1 M) at −78° C., is added n-BuLi (154 μL, 1.6 M in hexanes, 0.247 mmol, 1.2 equiv.), and the resulting solution is stirred at the same temperature for 30 min. DMF (32 μL, 0.412 mmol, 2.0 equiv.) is then added at −78° C. and, after being stirred at −78° C. for 30 min, the reaction mixture is slowly warmed up to 25° C. over a period of 2 h. Hexane (2.0 mL) is added and the resulting mixture is passed through a short silica gel cake eluting with 30% EtOAc in hexanes. The solvents are evaporated to give the crude aldehyde 22 (50 mg), which is used directly in the next step.

To a solution of aldehyde 22 (50 mg) in methanol (2.0 mL) at 25° C., is added sodium borohydride (15 mg, 0.397 mmol, 1.9 equiv.), and the resulting mixture is stirred at the same temperature for 30 min. EtOAc (1.0 mL) and hexane (2.0 mL) are added, and the mixture is passed through a short silica gel cake eluting with EtOAc. The solvents are then evaporated and the crude product is purified by flash column chromatography (silica gel, 20 to 50% EtOAc in hexanes) to furnish 2-hydroxymethyl-4-bromothiazole 21h (25 mg, 63% over two steps). R$_f$=0.16 (silica gel, 18% EtOAc in hexanes); IR (film) ν$_{max}$ 3288, 3122, 2922, 2855, 1486, 1447, 1345, 1250, 1183, 1085, 1059, 967, 893 cm$^{-1}$; $^1$H NMR (500 MHz, CDCl$_3$) δ7.20 (s, 1 H, ArH), 4.93 (s, 2 H, CH$_2$); HRMS (FAB), calcd. for C$_4$H$_4$BrNOS (M+H$^+$) 193.9275, found 193.9283.

2-(tert-Butyldimethylsilyloxymethyl)-4-bromothiazole 21s as illustrated in Scheme 5. To a solution of alcohol 21h (59 mg, 0.304 mmol, 1.0 equiv.) in CH$_2$Cl$_2$ (1.0 mL, 0.3 M) is added imidazole (62 mg, 0.608 mmol, 2.0 equiv.), followed by tert-butyldimethylchlorosilane (69 mg, 0.456 mmol, 1.3 equiv.) at 25° C. After 30 min at 25° C., the reaction mixture is quenched with methanol (100 mL) and then passed through silica gel eluting with CH$_2$Cl$_2$. Evaporation of solvents gives the desired silyl ether 21s (90 mg, 96%). R$_f$=60 (silica gel, 10% EtOAc in hexanes); IR (film) ν$_{max}$ 2943, 2858, 1489, 1465, 1355, 1254, 1193, 1108, 887, 841, 780 cm$^{-1}$; $^1$H NMR (500 MHz, CDCl$_3$) δ7.16 (s, 1 H, ArH), 4.93 (s, 2 H, CH$_2$), 0,94 (s, 9 H, SiC(CH$_3$)$_3$(CH$_3$)$_2$), 0.12 (s, 6 H, SiC(CH$_3$)$_3$(CH$_3$)$_2$); HRMS (FAB), calcd. for C$_{10}$H$_{18}$BrNOSSi (M+H$^+$) 308.0140, found 308.0151.

2-Vinyl-4-bromothiazole 21q as illustrated in Scheme 5. To a solution of 2,4-dibromothiazole 20 (437 mg, 1.80 mmol, 1.0 equiv.) in toluene is added tri-n-butyl(vinyl)tin (552 μL, 1.89 mmol, 1.05 equiv.) followed by Pd(PPh$_3$)$_4$ (208 mg, 0.180 mmol, 0.1 equiv.) and the resulting mixture is heated at 100° C. After 21 h, the mixture is cooled and purified directly by flash column chromatography (silica gel, 0 to 9% ether in hexanes) to afford 2-vinyl-4-bromothiazole 21q as an oil (285 mg, 83%). R$_f$=0.50 (silica gel, 17% ether in hexanes); IR (film) ν$_{max}$ 3121, 1470, 1259, 1226, 1124, 1082, 975, 926, 887, 833 cm$^{-1}$; $^1$H NMR (500 MHz, CDCl$_3$) δ7.13 (s, 1 H, ArH), 6.86 (dd, J=17.5,11.0 Hz, 1 H, CH=CH$_2$), 6.09 (d, J=17.5 Hz, 1 H, CHCH$_2$), 5.59 (d, J=10.5 Hz, 1 H, CHCH$_2$); GC/MS (EI), calcd. for C$_5$H$_4$BrNS (M$^+$) 189/191, found 189/191.

2-Ethyl-4-bromothiazole 21r as illustrated in Scheme 5. A solution of 2-vinyl-4-bromothiazole 21q (279 mg, 1.47 mmol, 1.0 equiv.) in ethanol (15 mL, 0.1 M) is added PtO$_2$ (50 mg, 0.220 mmol, 0.15 equiv.) and the resulting mixture is stirred under an atmosphere of hydrogen at 25° C. for 4 h. Subsequent filtration through a short plug of silica gel, eluting with EtOAc, and careful concentration under reduced pressure furnishes 2-ethyl-4-bromothiazole 21r (238 mg, 84%). R$_f$=0.63 (silica gel, CH$_2$Cl$_2$); IR (film) v$_{max}$ 3122, 2974, 2932, 1483, 1456, 1245, 1181, 1090, 1040, 956, 884, 831 cm$^{-1}$; $^1$H NMR (500 MHz, CDCl$_3$) δ7.08 (s, 1 H, ArH), 3.03 (q, J=7.5 Hz, 2 H, CH$_2$CH$_3$), 1.37 (t, J=7.5 Hz, 2 H, CH$_2$CH$_3$); GC/MS (EI), calcd. for C$_5$H$_6$BrNS (M$^+$) 191/193, found 191/193.

2-Thiomethyl-4-trimethylstannylthiazole 8b as illustrated in Scheme 3. To a solution of bromothiazole 21b (51 mg, 0.24 mmol, 1.0 equiv.) in degassed toluene (4.9 mL, 0.1 M) is added hexamethylditin (498 μL, 2.4 mmol, 10 equiv.) and Pd(PPh$_3$)$_4$ (14 mg, 0.012 mmol, 0.05 equiv.) and the reaction mixture is heated at 80° C. for 3 h. Then the reaction mixture is cooled to 25° C. and affords, after flash column chromatography (silica gel, 5% Et$_3$N in hexanes), stannane 8b (71 mg, 100%). R$_f$=0.67 (silica gel; pre-treated with Et$_3$N, 10% EtOAc); IR (film) v$_{max}$ 2981, 2924, 1382, 1030, 772 cm$^{-1}$; $^1$H NMR (500 MHz, CDCl$_3$) δ7.25 (s, 1 H, ArH), 2.70 (s, 3 H, SCH$_3$), 0.32 (s, 9 H, Sn(CH$_3$)$_3$); HRMS (FAB), calcd. for C$_7$H$_{13}$NS$_2$Sn (M+H$^+$) 295.9588, found 295.9576.

2-Methoxy-4-trimethylstannylthiazole 8p as illustrated in Scheme 4. To a solution of bromothiazole 21p (147 mg, 0.758 mmol, 1.0 equiv.) in degassed toluene (7.6 mL, 0.1 M) is added hexamethyiditin (785 μL, 3.79 mmol, 5.0 equiv.) and Pd(PPh$_3$)$_4$ (88 mg, 0.076 mmol, 0.1 equiv.) and the reaction mixture is heated at 100° C. for 30 min according to the procedure described for the synthesis of stannane 8b to afford, after flash column chromatography (silica gel, 5% Et$_3$N in hexanes), stannane 8p (170 mg, 81%). R$_f$=0.49 (silica gel; pretreated with Et$_3$N, 17% ether in hexanes); IR (film) v$_{max}$ 2985, 2948, 2915, 1512, 1414, 1259, 1234, 1219, 1087, 988 cm$^{-1}$; $^1$H NMR (500 MHz, CDCl$_3$) δ6.72 (s, 1 H, ArH), 4.07 (s, 3 H, OCH$_3$), 0.32 (s, 9 H, Sn(CH$_3$)$_3$); HRMS (FAB), calcd. for C$_7$H$_{13}$NOSSn (M+H$^+$) 279.9818, found 279.9810.

2-(tert-butyidimethylsilyloxymethyl)-4-tri-n-butylstannylthiazole 8s as illustrated in Scheme 5. To a solution of bromothiazole 21s (20 mg, 0.065 mmol, 1.0 equiv.) in ether (1.0 mL, 0.07M) at −78° C., is added n-BuLi (49 μL, 1.6 M in hexanes, 0.078 mmol, 1.2 equiv.) and the resulting mixture is stirred at −78° C. for 10 min. Tri-n-butyltin chloride (23 μL, 0.078 mmol, 1.2 equiv.) is then added, the solution stirred at −78° C. for 10 min, and then slowly warmed to 25° C. over a period of 1 h. The reaction mixture is diluted with hexane (2.0 mL), and passed through silica gel eluting with 20% EtOAc in hexanes. Flash column chromatography (silica gel; pre-treated with Et$_3$N, 5% ether in hexanes) furnishes the desired stannane 8s (35 mg, 85%). R$_f$=0.36 (silica gel; 5% EtOAc in hexanes); IR (film) v$_{max}$ 2955, 2928, 2856, 1464, 1353, 1255, 1185, 1103, 1081, 1006, 841 cm$^{-1}$; $^1$H NMR (500 MHz, C$_6$D$_6$) δ7.08 (s, 1 H, ArH), 4.98 (s, 2 H, CH$_2$), 1.75–1.57 (m, 6 H, CH$_3$CH$_2$), 1.44–1.31 (m, 6 H, CH$_3$CH$_2$CH$_2$), 1.26–1.09 (m, 6 H, CH$_3$CH$_2$CH$_2$CH$_2$), 0.94 (s, 9 H, SiC(CH$_3$)$_3$(CH$_3$)$_2$), 0.91 (t, J=7.0 Hz, 9 H, CH$_3$), −0.02 (s, 6 H, SiC(CH$_3$)$_3$(CH$_3$)$_2$); HRMS (FAB), calcd. for C$_{22}$H$_{45}$NOSSiSn (M+H$^+$) 520.2093, found 520.2074.

2-Hydroxymethyl-4-tri-n-butylstannylthiazole 8h as illustrated in Scheme 5. To a solution of silyl ether 8s (20 mg, 0.039 mmol, 1.0 equiv.) in THF (1.0 mL, 0.04 M) is added TBAF (46 μL, 1.0 M in THF, 0.046 mmol, 1.2 equiv.) and the reaction mixture is stirred at 25° C. for 20 min. Hexane (2.0 mL) is added, and the mixture passed through silica gel eluting with EtOAc. Evaporation of solvents gives the desired alcohol 8h (15 mg, 95%). R$_f$=0.09 (silica gel, 20% ether in hexanes); IR (film) v$_{max}$ 3209, 2956, 2923, 2855, 1461, 1342, 1253, 1174, 1064, 962 cm$^{-1}$; $^1$H NMR (500 MHz, CDCl$_3$) δ7.30 (m, 1 H, ArH), 4.99 (s, 2 H, CH$_2$), 3.64 (bs, 1 H, OH), 1.62–1.45 (m, 6 H, CH$_3$CH$_2$) 1.38–1.27 (m, 6 H, CH$_3$CH$_2$), 1.19–1.02 (m, 6 H, CH$_3$CH$_2$CH$_2$CH$_2$), 0.88 (t, J=7.0 Hz, 9 H, CH$_3$); HRMS (FAB), calcd. for C$_{16}$H$_{31}$NOSSn (M+H$^+$) 406.1228, found 406.1237.

2-Fluoromethyl-4-tri-n-butylstannylthiazole 8j as illustrated in Scheme 5. To a solution of alcohol 8h (90 mg, 0.223 mmol, 1.0 equiv.) in CH$_2$Cl$_2$ (2.2 mL, 0.1 M) at −78° C. is added DAST (32 μL, 0.242 mmol, 1.1 equiv.) and the solution is stirred at this temperature for 10 min. After quenching with saturated aqueous NaHCO$_3$ (2 mL) the mixture is allowed to warm up to 25° C., and then partitioned between CH$_2$Cl$_2$ (15 mL) and saturated aqueous NaHCO$_3$ (15 mL). The layers are separated and the aqueous phase is extracted with CH$_2$Cl$_2$ (2×15 mL). The combined organic extracts are washed with brine (40 mL), dried (MgSO$_4$) and concentrated under reduced pressure. Flash column chromatography (silica gel; pre-treated with Et$_3$N, 17% ether in hexanes) furnishes stannane 8j (52 mg, 57%). R$_f$=0.59 (silica gel, 17% ether in hexanes); IR (film) v$_{max}$ 2956, 2925, 2870, 2863, 1464, 1376, 1358, 1184, 1084, 1023, 874, 807 cm$^{-1}$; $^1$H NMR (500 MHz, CDCl$_3$) ε7.41 (s, 1 H, ArH), 5.69 (d, J=47.5 Hz, 2 H, CH$_2$F), 1.58–1.52 (m, 6 H, (CH$_3$CH$_2$(CH$_2$)$_2$)$_3$Sn), 1.36–1.29 (m, 6 H, (CH$_3$CH$_2$CH$_2$CH$_2$)$_3$Sn), 1.14–1.07 (m, 6 H, (CH$_3$CH$_2$CH$_2$CH$_2$)$_3$Sn), 0.88 (t, J=7.5 Hz, 9 H, (CH$_3$CH$_2$CH$_2$CH$_2$)$_3$Sn); HRMS (FAB), calcd. for C$_{16}$H$_{30}$FNSSn (M+H$^+$) 408.1183, found 408.1169.

2-Ethoxy-4-ti-n-butylstannylthiazole 8d as illustrated in Scheme 4. A solution of bromothiazole 21d (82 mg, 0.394 mmol, 1.0 equiv.) in ether (3.9 mL, 0.1 M) is treated with n-BuLi (289 μL, 1.5 M in hexanes, 0.433 mmol, 1.1 equiv.) and tri-n-butyltin chloride (128 μL, 0.473 mmol, 1.2 equiv.) according to the procedure described for the synthesis of stannane 8s, to yield, after column chromatography (silica gel; pre-treated with Et$_3$N, hexanes), stannane 8d (161 mg, 98%). IR (film) v$_{max}$ 2956, 2927, 2870, 2851, 1504, 1472, 1258, 1257, 1232, 1211, 1082, 1023, 960, 894, 872 cm$^{-1}$; $^1$H NMR (500 MHz, CDCl$_3$) δ6.65 (s, 1 H, ArH), 4.43 (q, J=7.0 Hz, 2 H, CH$_3$CH$_2$O), 1.61–1.53 (m, 6 H, (CH$_3$CH$_2$(CH$_2$)$_2$)$_3$Sn), 1.43 (t, J=7.0 Hz, 3 H, CH$_3$CH$_2$), 1.37–1.30 (m, 6 H, (CH$_3$CH$_2$CH$_2$CH$_2$)$_3$Sn), 1.08–1.04 (m, 6 H, (CH$_3$CH$_2$CH$_2$CH$_2$)$_3$Sn), 0.89 (t, J=7.5 Hz, 9 H, (CH$_3$CH$_2$CH$_2$CH$_2$)$_3$Sn); HRMS (FAB), calcd. for C$_{17}$H$_{33}$NOSSn (M+H$^+$) 418.1380, found 418.1396.

2-Vinyl-4-tri-n-butylstannylthiazole 8q as illustrated in Scheme 5. A solution of bromothiazole 21q (191 mg, 1.00 mmol, 1.0 equiv.) in ether (14.0 mL, 0.07 M), is treated with n-BuLi (804 μL, 1.5 M in hexanes, 1.20 mmol, 1.2 equiv.) and tri-n-butyltin chloride (341 μL, 1.26 mmol, 1.25 equiv.) according to the procedure described for the synthesis of stannane 8s to yield, after column chromatography (silica gel; pre-treated with Et$_3$N, hexanes), stannane 8q (112 mg, 28%). R$_f$=0.63 (silica gel, 17% ether in hexanes); IR (film) v$_{max}$ 2956, 2925, 2870, 2850, 1459, 1377, 1205, 1080, 981, 913, 868 cm$^{-1}$; $^1$H NMR (500 MHz, CDCl$_3$) δ7.21 (s, 1 H, ArH), 7.02 (dd, J=17.5, 11.0 Hz, 1 H, CH=CH$_2$), 6.00 (d, J=17.5 Hz, 1 H, CHCH$_2$), 5.52 (d, J=11.0 Hz, 1 H, CH=CH$_2$), 1.61–1.53 (m, 6 H, (CH$_3$CH$_2$(CH$_2$)$_2$)$_3$Sn), 1.37–1.27 (m, 6 H, (CH$_3$CH$_2$CH$_2$CH$_2$)$_3$Sn), 1.13–1.10 (m, 6 H, (CH$_3$CH$_2$CH$_2$CH$_2$)$_3$Sn), 0.88 (t, J=7.5 Hz, 9 H, (CH$_3$CH$_2$CH$_2$CH$_2$)$_3$Sn); HRMS (FAB), calcd. for C$_{17}$H$_{31}$NSSn (M+H$^+$) 402.1279, found 402.1290.

2-Ethyl-4-tri-n-butylstannylthiazole 8r as illustrated in Scheme 5. A solution of bromothiazole 21r (238 mg, 1.24 mmol, 1.0 equiv.) in ether (12.0 mL, 0.1M) at −78° C., is treated with n-BuLi (909 μL, 1.5 M in hexanes, 1.36 mmol, 1.1 equiv.) and tri-n-butyltin chloride (403 μL, 1.49 mmol, 1.2 equiv.) according to the procedure described for the synthesis of stannane 8s to yield, after column chromatography (silica gel; pre-treated with Et$_3$N, hexanes), stannane 8r (357 mg, 72%). R$_f$=0.64 (silica gel, CH$_2$Cl$_2$); IR (film) ν$_{max}$ 2956, 2925, 2870, 2852, 1464, 1376, 1292, 1174, 1072, 1033, 953, 875 cm$^{-1}$; $^1$H NMR (400 MHz, CDCl$_3$) δ7.18 (s, 1 H, ArH), 3.10 (q, J=7.6 Hz, 2 H, CH$_3$CH$_2$Ar), 1.60–1.50 (m, 6 H, (CH$_3$CH$_2$(CH$_2$)$_2$)$_3$Sn), 1.39 (t, J=7.6 Hz, 3 H, CH$_3$CH$_2$Ar), 1.36–1.30 (m, 6 H, (CH$_3$CH$_2$CH$_2$CH$_2$)$_3$Sn), 1.13–1.08 (m, 6 H, (CH$_3$CH$_2$CH$_2$CH$_2$)$_3$Sn), 0.88 (t, J=7.3 Hz, 9 H, (CH$_3$CH$_2$CH$_2$CH$_2$)$_3$Sn); HRMS (FAB), calcd. for C$_{17}$H$_{33}$NSSn (M+H$^+$) 404.1434, found 404.1416.

cis-Macrolactone 18h as illustrated in Scheme 3. A solution of vinyl iodide 7 (10.0 mg, 0.020 mmol, 1.0 equiv.), stannane 8h (16.0 mg, 0.040 mmol, 2.0 equiv.) and Pd(PPh$_3$)$_4$ (2.1 mg, 0.002 mmol, 0.1 equiv.) in degassed toluene (200 μL, 0.1 M) is heated at 100° C. for 20 min. The reaction mixture is poured into saturated aqueous NaHCO$_3$—NaCl (5 mL) and extracted with EtOAc (2×5 mL). After drying the combined organic fractions (Na$_2$SO$_4$), evaporation of the solvents and purification by preparative thin layer chromatography (500 mm silica gel plate, 50% EtOAc in hexanes), macrolactone 18h is obtained (7.5 mg, 76%). R$_f$=0.29 (silica gel, 50% EtOAc in hexanes); [α]$^{22}_D$ −44.2 (c 0.60, CHCl$_3$); IR (thin film) ν$_{max}$ 3387 (br), 2925, 2859, 1730, 1688, 1508, 1461, 1256, 1183, 1150, 1061, 980, 755 cm$^{-1}$; $^1$H NMR (500 MHz, CDCl$_3$) δ7.12 (s, 1 H, ArH), 6.61 (s, 1 H, CH=C(CH$_3$)), 5.45 (ddd, J=10.5, 10.5, 4.5 Hz, 1 H, CH=CHCH$_2$), 5.38 (ddd, J=10.5, 10.5, 5.0 Hz, 1 H, CH=CHCH$_2$), 5.31 (d, J=8.5 Hz, 1 H, CHOCO), 4.92 (d, J=4.0 Hz, 2 H, CH$_2$OH), 4.23 (ddd, J=11.5, 5.5, 2.5 Hz, 1 H, (CH$_3$)$_2$CCH(OH)), 3.75–3.71 (m, 1 H, CHOH(CHCH$_3$)), 3.32 (d, J=5.5 Hz, 1 H, C(CH$_3$)$_2$CHOHO, 3.25 (t, J=4.0 Hz, 1 H, CH$_2$OH), 3.13 (qd, J=7.0, 2.0 Hz, 1 H, CH$_3$CH(C=O)), 3.03 (d, J=2.0 Hz, 1 H, CH$_3$CHCH(OH)CHCH$_3$), 2.68 (ddd, J=15.0, 9.5, 9.5 Hz, 1 H, =CHCH$_2$CHO), 2.50 (dd, J=15.0, 11.5 Hz, 1 H, CH$_2$COO), 2.35 (dd, J=15.0, 2.5 Hz, 1 H, CH$_2$COO), 2.31–2.24 (m, 1 H, =CHCH$_2$CHO), 2.24–2.16 (m, 1 H), 2.09 (s, 3 H, CH=CCH$_3$), 2.06–1.98 (m, 1 H), 1.82–1.73 (m, 1 H), 1.72–1.62 (m, 1 H), 1.39–1.17 (m, 3 H), 1.33 (s, 3 H, C(CH$_3$)$_2$), 1.19 (d, J=7.0 Hz, 3 H, CH$_3$CH(C=O)), 1.08 (s, 3 H, C(CH$_3$)$_2$), 1.00 (d, J=7.0 Hz, 3 H, CH$_3$CHCH$_2$); HRMS (FAB), calcd. for C$_{26}$H$_{39}$NO$_6$S (M+Cs$^+$) 626.1552, found 626.1530.

Epothilone E (3) as illustrated in Schemes 2 and 3. To a solution of lactone 18h (10.0 mg, 0.020 mmol, 1.0 equiv.) in methanol (600 μL, 0.03 M) is added acetonitrile (32 μL, 0.606 mmol, 30 equiv.), KHCO$_3$ (10 mg, 0.102 mmol, 5 equiv.) and hydrogen peroxide (27 μL, 35% w/w in water, 0.303 mmol, 15 equiv.) and the reaction mixture stirred at 25° C. for 3 h. Additional acetonitrile (32 μL, 0.606 mmol, 30 equiv.), KHCO$_3$ (10 mg, 0.102 mmol, 5 equiv.) and hydrogen peroxide (27 μL, 35% w/w in water, 0.303 mmol, 15 equiv.) are then added and stirring is continued for a further 3 h. The reaction mixture is then passed directly through a short plug of silica gel, eluting with ether, and the filtrate is concentrated under reduced pressure. Preparative thin layer chromatography (250 mm silica gel plate, 50% EtOAc in hexanes) furnishes unreacted starting material 18h (5.0 mg, 50%) and epothilone E (3) (3.4 mg, 33%). R$_f$=0.56 (silica gel, 66% EtOAc in hexanes); [α]$^{22}_D$=−27.5 (c 0.20, CHCl$_3$); IR (film) ν$_{max}$ 3413, 2928, 2867, 1731, 1689, 1462, 1375, 1257, 1152, 1061, 978, 756 cm$^-$; $^1$H NMR (600 MHz, CDCl$_3$) δ7.13 (s, 1 H, ArH), 6.61 (s, 1 H, CH=CCH$_3$), 5.46 (dd, J=8.1, 2.4 Hz, 1 H, CHOCO), 4.94 (d, J=5.2 Hz, 2 H, CH$_2$OH), 4.16–4.12 (m, 1 H, (CH$_3$)$_2$CCH(OH)), 3.82–3.78 (m, 1 H, CHOH(CHCH$_3$)), 3.66 (bs, 1 H, OH), 3.23 (qd, J=6.8, 5.2 Hz, 1 H, CH$_3$CH(C=O)), 3.04 (ddd, J=8.1, 4.5, 4.5 Hz, 1 H, CH$_2$CH(O)CHCH$_2$), 2.91 (ddd, J=7.3, 4.5, 4.1 Hz, 1 H, CH$_2$CH(O)CHCH$_2$), 2.61 (t, J=5.2 Hz, 1 H, CH$_2$OH), 2.55 (dd, J=14.7, 10.4 Hz, 1 H, CH$_2$COO), 2.48 (bs, 1 H, OH), 2.45 (dd, J=14.7, 3.2 Hz, 1 H, CH$_2$COO), 2.14–2.07 (m, 1 H, CH$_2$CH(O)CHCH$_2$), 2.11 (s, 3 H, CH=CCH$_3$), 1.91 (ddd, J=15.1, 8.1, 8.1 Hz, 1 H, CH$_2$CH(O)CHCH$_2$), 1.78–1.66 (m, 2 H, CH$_2$CH(O)CHCH$_2$), 1.52–1.38 (m, 5 H), 1.36 (s, 3 H, C(CH$_3$)$_2$), 1.18 (d, 3 H, J=6.8 Hz, CH$_3$CH(C=O)), 1.10 (s, 3 H, C(CH$_3$)$_2$), 1.01 (d, J=7.0 Hz, 3 H, CH$_3$CHCH$_2$); HRMS (FAB), calcd. for C$_{26}$H$_{39}$NO$_7$S (M+H$^+$) 510.2525, found 510.2539.

cis-Macrolactone 18b as illustrated in Scheme 3. A solution of vinyl iodide 7 (9.2 mg, 0.018 mmol, 1.0 equiv.), stannane 8b (10.7 mg, 0.036 mmol, 2.0 equiv.) and Pd(PPh$_3$)$_4$ (2.1 mg, 0.0018 mmol, 0.1 equiv.) in degassed toluene (180 μL, 0.1 M) is heated at 100° C. for 40 min, according to the procedure described for the synthesis of lactone 18h, to yield, after preparative thin layer chromatography (250 mm silica gel plate, 75% ether in hexanes), macrolactone 18b (4.1 mg, 44%). R$_f$=0.50 (silica gel, 50% EtOAc in hexanes); [α]$^{22}_D$ −38.6 (c 0.21, CHCl$_3$); IR (thin film) ν$_{max}$ 3444, 2925, 1732, 1682, 1259, 1037, 756 cm$^{-1}$; $^1$H-NMR (500 MHz, CDCl$_3$) δ6.99 (s, 1 H, CH=C(CH$_3$)), 6.52 (bs, 1 H, ArH), 5.45 (ddd, J=10.5, 10.5, 4.0 Hz, 2 H, CH=CHCH$_2$), 5.39 (ddd, J=10.5, 10.5, 4.0 Hz, 1 H, CH=CHCH$_2$), 5.29 (d, J=8.0 Hz, 1 H, CHOCO), 4.20 (ddd, J=11.0, 5.5, 2.5 Hz, 1 H, (CH$_3$)$_2$CCH(OH)), 3.75–3.73 (m, 1 H, CHOH(CHCH$_3$)), 3.13 (qd, J=6.5, 2.0 Hz, 1 H, CH$_3$CH(C=O)), 2.98 (d, J=2.0 Hz, 1 H, CHOH(CHCH$_3$)), 2.93 (d, J=5.5 Hz, 1 H, (CH$_3$)$_2$CCH(OH)), 2.71 (ddd, J=15.0, 10.0, 10.0 Hz, 1 H, CH=CHCH$_2$), 2.70 (s, 3 H, SCH$_3$), 2.51 (dd, J=15.5, 11.5 Hz, 1 H, CH$_2$COO), 2.30 (dd, J=15.0, 2.5 Hz, 1 H, CH$_2$COO), 2.28–2.16 (m, 2 H), 2.13 (d, J=1.0 Hz, 3 H, CH=CCH$_3$), 2.06–1.98 (m, 1 H), 1.79–1.60 (m, 2 H), 1.40–1.06 (m, 3 H), 1.33 (s, 3 H, C(CH$_3$)$_2$), 1.19 (d, J=7.0 Hz, 3 H, CH$_3$CH(C=O)), 1.09 (s, 3 H, C(CH$_3$)$_2$), 1.00 (d, J=7.0 Hz, 3 H, CH$_3$CHCH$_2$); HRMS (FAB), calcd. for C$_{26}$H$_{39}$NO$_5$S$_2$ (M+Cs$^+$) 642.1324, found 642.1345.

trans-Macrolactone 19b as illustrated in Scheme 3. A solution of vinyl iodide 11 (6.9 mg, 0.014 mmol, 1.0 equiv.), stannane 8b (8.2 mg, 0.028 mmol, 2.0 equiv.) and Pd(PPh$_3$)$_4$ (1.6 mg, 0.0014 mmol, 0.1 equiv.) in degassed toluene (140 μL, 0.1 M) is heated at 100° C. for 40 min, according to the procedure described for the synthesis of lactone 18h, to yield, after preparative thin layer chromatography (250 mm silica gel plate, 75% ether in hexanes), macrolactone 19b (5.0 mg, 72%). R$_f$=0.47 (silica gel, 50% EtOAc in hexanes); [α]$^{22}_D$ −32.9 (c 0.35, CHCl$_3$); IR (film) ν$_{max}$ 3488, 2928, 1728, 1692, 1259, 1036, 800, 757 cm$^{-1}$; $^1$H NMR (500 MHz, CDCl$_3$) δ7.00 (s, 1 H, ArH), 6.48 (s, 1 H, CH=CCH$_3$), 5.53 (ddd, J=15.0, 7.5, 7.5 Hz, 1 H, CH=CHCH$_2$), 5.40 (d, J=8.0 Hz, 1 H, CHOCO), 5.39 (ddd, J=15.0, 7.5, 7.5 Hz, 1 H, CH=CHCH$_2$), 4.12 (ddd, J=11.0, 2.5, 2.5 Hz, 1 H, (CH$_3$)$_2$CCHOH), 3.77–3.74 (m, 1 H, CHOH(CHCH$_3$)), 3.24 (m, 1 H, CH=CHCH$_2$), 3.07 (m, 1

H, CH$_3$CH(C═O)), 2.70 (s, 3 H, SCH$_3$), 2.61 (d, J=3.5 Hz, 1 H, CHOH(CHCH$_3$)), 2.59–2.44 (m, 5 H), 2.19–2.12 (m, 1 H), 2.13 (s, 3 H, CH═CCH$_3$), 2.02–1.94 (m, 1 H), 1.70–1.55 (m, 2 H), 1.48–1.41 (m, 1 H), 1.29 (s, 3 H, C(CH$_3$)$_2$), 1.18 (d, J=7.0 Hz, 3 H, CH$_3$CH(C═O)), 1.08 (s, 3 H, C(CH$_3$)$_2$), 0.99 (d, J=7.0 Hz, 3 H, CH$_3$CHCH$_2$); HRMS (FAB), calcd. for C$_{26}$H$_{39}$NO$_5$S$_2$ (M+Cs$^+$) 642.1324, found 642.1298.

cis-Macrolactone 18d as illustrated in Scheme 3. A solution of vinyl iodide 7 (14 mg, 0.028 mmol, 1.0 equiv.), stannane 8d (14 mg, 0.055 mmol, 2.0 equiv.) and PdCl$_2$(MeCN)$_2$ (2.0 mg, 0.008 mmol, 0.3 equiv.) in degassed DMF (280 µL, 0.1 M) is stirred at 25° C. for 20 h. The resulting mixture is then concentrated under reduced pressure, filtered through silica, eluting with EtOAc, and purified by preparative thin layer chromatography (250 mm silica gel plate, 50% ether in hexanes) to furnish macrolactone 18d (12.5 mg, 89%). R$_f$=0.30 (silica gel, 66% ether in hexanes); [α]$^{22}_D$ 70.2 (c 0.63, CHCl$_3$); IR (thin film) ν$_{max}$ 3501 (br), 2934, 1732, 1688, 1526, 1472, 1386, 1232, 1150, 1091, 1007 cm$^{-1}$; $^1$H NMR (500 MHz, CDCl$_3$) δ6.47 (s, 1 H, ArH), 6.33 (s, 1 H, CH═C(CH$_3$)), 5.43 (ddd, J=10.5, 10.5, 3.5 Hz, 1 H, CH═CHCH$_2$), 5.37 (ddd, J=10.5, 10.5, 4.5 Hz, 1 H, CH═CHCH$_2$), 5.26 (dd, J=9.5, 1.5 Hz, 1 H, CHOCO), 4.44 (q, J=7.0 Hz, 2 H, CH$_3$CH$_2$O), 4.18 (ddd, J=11.0, 5.5, 2.5 Hz, 1 H, (CH$_3$)$_2$CCH(OH)), 3.73 (m, 1 H, CHOH(CHCH$_3$)), 3.12 (qd, J=7.0, 2.0 Hz, 1 H, CH$_3$CH(C═O)), 2.98 (d, J=1.5 Hz, 1 H, OH), 2.95 (d, J=5.5 Hz, 1 H, OH), 2.69 (ddd, J=15.0, 10.0, 10.0 Hz, 1 H, CH═CHCH$_2$CHO), 2.49 (dd, J=15.5, 11.5 Hz, 1 H, CH$_2$COO), 2.36 (dd, J=15.5, 2.5 Hz, 1 H, CH$_2$COO), 2.23–2.16 (m, 3 H), 2.11 (s, 3 H, CH═C(CH$_3$)), 2.04–1.98 (m, 1 H), 1.77–1.71 (m, 1 H), 1.70–1.61 (m, 1 H), 1.42 (t, J=7.0 Hz, 3 H, CH$_3$CH$_2$O), 1.38–1.16 (m, 2 H), 1.31 (s,3 H, C(CH$_3$)$_2$), 1.17 (d, J=7.0 Hz, 3 H, CH$_3$CH(C═O)), 1.08 (s, 3 H, C(CH$_3$)$_2$), 0.99 (d, J=7.0 Hz, 3 H, CH$_3$CHCH$_2$); HRMS (FAB), calcd. for C$_{27}$H$_{41}$NO$_6$S (M+Cs$^+$) 640.1709, found 640.1732.

trans-Macrolactone 19d as illustrated in Scheme 3. A solution of vinyl iodide 11 (14 mg, 0.028 mmol, 1.0 equiv.), stannane 8d (23 mg, 0.055 mmol, 2.0 equiv.) and PdCl$_2$(MeCN)$_2$ (2.0 mg, 0.008 mmol, 0.3 equiv.) in degassed DMF (280 µL, 0.1 M) is stirred at 25° C. for 20 h, according to the procedure described for the synthesis of macrolactone 18d to yield, after preparative thin layer chromatography (250 mm silica gel plate, 50% EtOAc in hexanes), macrolactone 19d (12 mg, 86%). R$_f$=0.27 (silica gel, 66% ether in hexanes); [α]$^{22}_D$ −28.0 (c 0.48, CHCl$_3$); IR (thin film) ν$_{max}$ 3495 (br), 2930, 1732, 1690, 1526, 1472, 1233, 1017, 976 cm$^{-1}$; $^1$H NMR (500 MHz, CDCl$_3$) δ6.50 (s, 1 H, ArH), 6.30 (s, 1 H, CH═C(CH$_3$)), 5.57–5.51 (m, 1 H, CH═CHCH$_2$), 5.42–5.36 (m, 1 H, CH═CHCH$_2$), 5.37 (dd, J=9.0, 2.5 Hz, 1 H, CHOCO), 4.46 (q, J=7.0 Hz, 2 H, CH$_3$CH$_2$O), 4.10 (ddd, J=10.5, 3.5, 3.0 Hz, 1 H, (CH$_3$)$_2$CCH(OH)), 3.76–3.73 (m, 1 H, CHOH(CHCH$_3$)), 3.23 (qd, J=7.0, 4.5 Hz, 1 H, CH$_3$CH(C═O)), 3.07 (d, J=3.5 Hz, 1 H, OH), 2.57–2.38 (m, 3 H), 2.56 (dd, J=15.5, 10.5 Hz, 1 H, CH$_2$COO), 2.47 (dd, J=15.5, 2.5 Hz, 1 H, CH$_2$COO), 2.18–2.16 (m, 1 H), 2.13 (s, 3 H, CH═C(CH$_3$)), 2.03–1.94 (m, 1 H), 1.70–1.55 (m, 2 H), 1.48–1.41 (m, 1 H), 1.44 (t, J=7.0 Hz, 3 H, CH$_3$CH$_2$O), 1.29 (s, 3 H, C(CH$_3$)$_2$), 1.27–1.16 (m, 1 H), 1.18 (d, J=7.0 Hz, 3 H, CH$_3$CH(C═O)), 1.08 (s, 3 H, C(CH$_3$)$_2$), 0.98 (d, J=7.0 Hz, 3 H, CH$_3$CHCH$_2$); HRMS (FAB), calcd. for C$_{27}$H$_{41}$NO$_6$S (M+Cs$^+$) 640.1709, found 640.1731.

tran-Macrolactone 19h as illustrated in Scheme 3. A solution of vinyl iodide 11 (5.1 mg, 0.010 mmol, 1.0 equiv.), stannane 8h (8.0 mg, 0.020 mmol, 2.0 equiv.) and Pd(PPh$_3$)$_4$ (1.1 mg, 0.001 mmol, 0.1 equiv.) in degassed toluene (100 µL, 0.1 M) is heated at 100° C. for 20 min according to the procedure described for the synthesis of macrolactone 18h, to yield, after preparative thin layer chromatography (250 mm silica gel plate, 50% EtOAc in hexanes), macrolactone 19h (4.3 mg, 88%). R$_f$=0.20 (silica gel, 50% EtOAc in hexanes); [α]$^{22}_D$ −31.5 (c 0.60, CHCl$_3$); IR (thin film) ν$_{max}$ 3410 (br), 2930, 1726, 1692, 1463, 1374, 1255, 1180, 1064, 973 cm$^{-1}$; $^1$H NMR (500 MHz, CDCl$_3$) δ7.13 (s, 1 H, ArH), 6.60 (s, 1 H, CH═C(CH$_3$)), 5.48 (ddd, J=15.0, 7.5, 7.5 Hz, 1 H, CH═CHCH$_2$), 5.40 (dd, J=5.5, 5.5 Hz, 1 H, CHOCO), 5.35 (ddd, J=15.0, 7.5, 7.5 Hz, 1 H, CH═CHCH$_2$), 4.91 (d, J=7.0 Hz, 2 H, CH$_2$OH), 4.23 (ddd, J=9.5, 3.5, 3.0 Hz, 1 H, (CH$_3$)$_2$CCH(OH)), 3.74 (ddd, J=7.0, 5.0, 2.5 Hz, 1 H, CHOH(CHCH$_3$)), 3.34 (t, J=7.0 Hz, 1 H, CH$_2$OH), 3.26 (qd, J=7.0, 7.0 Hz, 1 H, CH$_3$CH(C═O)), 3.05 (d, J=3.5 Hz, 1 H, C(CH$_3$)$_2$CHOH), 3.00 (d, J=5.0 Hz, 1 H, CH$_3$CHCH(OH)CHCH$_3$), 2.56 (dd, J=15.5, 9.5 Hz, 1 H, CH$_2$COO), 2.47 (dd, J=15.5, 3.0 Hz, 1 H, CH$_2$COO), 2.58–2.45 (m, 1 H, ═CHCH$_2$CH), 2.24–2.16 (m, 1 H, ═CHCH$_2$CH), 2.08 (s, 3 H, CH═CCH$_3$), 1.98–1.90 (m, 1 H), 1.63–1.56 (m, 2 H), 1.54–1.46 (m, 1 H), 1.41–1.30 (m, 1 H), 1.27 (s, 3 H, C(CH$_3$)$_2$), 1.20 (d, J=7.0 Hz, 3 H, CH$_3$CH(C═O)), 1.07 (s, 3 H), C(CH$_3$)$_2$), 0.99 (d, J=7.0 Hz, 3 H, CH$_3$CHCH$_2$); HRMS (FAB), calcd. for C$_{26}$H$_{39}$NO$_6$S (M+Cs$^+$) 626.1552, found 626.1536.

cis-Macrolactone 18j as illustrated in Scheme 3. A solution of vinyl iodide 7 (12.5 mg, 0.025 mmol, 1.0 equiv.), stannane 8j (20 mg, 0.049 mmol, 2.0 equiv.) and PdCl$_2$(MeCN)$_2$ (1.5 mg, 0.006 mmol, 0.2 equiv.) in degassed DMF (250 µL, 0.1 M) is stirred at 25° C. for 20 h, according to the procedure described for the synthesis of macrolactone 18d, to yield, after preparative thin layer chromatography (250 mm silica gel plate, 67% ether in hexanes) macrolactone 18j (9 mg, 74%). R$_f$=0.32 (silica gel, 50% EtOAc in hexanes); [α]$^{22}_D$ −65.3 (c 0.45, CHCl$_3$); IR (thin film) ν$_{max}$ 3406 (br), 2924, 2852, 1732, 1682, 1455, 1366, 1263, 1192, 1148, 1096, 1043, 983, 881 cm$^{-1}$; $^1$H NMR (500 MHz, CDCl$_3$) δ7.21 (s, 1 H, ArH), 6.62 (s, 1 H, CH═C(CH$_3$)), 5.60 (d, J=47.0 Hz, 2 H, CH$_2$F), 5.45 (ddd, J=10.5, 10.5, 4.0 Hz, 1 H, CH═CHCH$_2$), 5.38 (ddd, J=10.0, 10.0, 5.0 Hz, 1 H, CH═CHCH$_2$), 5.31 (dd, J=10.0, 1.5 Hz, 1 H, CHOCO), 4.19 (ddd, 1 H, J=11.0, 5.0, 2.5 Hz, 1 H, (CH$_3$)$_2$CCH(OH)), 3.73 (m, 1 H, CHOH(CHCH$_3$)), 3.13 (qd, J=7.0, 2.0 Hz, 1 H, CH$_3$CH(C═O)), 2.97 (d, J=2.0 Hz, 1 H, OH), 2.93 (d, J=5.5 Hz, 1 H, OH), 2.71 (ddd, J=15.0, 10.0, 10.0 Hz, 1 H, CH═CHCH$_2$CHO), 2.51 (dd, J=15.5, 11.5 Hz, 1 H, CH$_2$COO), 2.39 (dd, J=15.5, 2.0 Hz, 1 H, CH$_2$COO), 2.29–2.22 (m, 1 H), 2.22–2.16 (m, 1 H), 2.11 (d, J=1.0 Hz, 3 H, CH═C(CH$_3$)), 2.06–1.99 (m, 1 H), 1.77–1.71 (m, 1 H), 1.69–1.62 (m, 1 H), 1.38–1.16 (m, 3 H), 1.32 (s, 3 H, C(CH$_3$)$_2$), 1.18 (d, J=7.0 Hz, 3 H, CH$_3$CH(C═O)), 1.08 (s, 3 H, C(CH$_3$)$_2$), 1.00 (d, J=7.0 Hz, 3 H, CH$_3$CHCH$_2$); HRMS (FAB), calcd. for C$_{26}$H$_{38}$FNO$_5$S (M+Cs$^+$) 628.1509, found 628.1530.

trans-Macrolactone 19j as illustrated in Scheme 3. A solution of vinyl iodide 11 (15 mg, 0.030 mmol, 1.0 equiv.), stannane 8j (27 mg, 0.066 mmol, 2.2 equiv.) and PdCl$_2$(MeCN)$_2$ (1.5 mg, 0.006 mmol, 0.2 equiv.) in degassed DMF (300 µL, 0.1 M) is stirred at 25° C. for 20 h, according to the procedure described for the synthesis of macrolactone 18d, to yield, after preparative thin layer chromatography (250 mm silica gel plate, 50% EtOAc in hexanes) macrolactone 19j (11 mg, 75%). R$_f$=0.17 (silica gel, 33% ether in hexanes); [α]$^{22}_D$ −37.1 (c 0.55, CHCl$_3$); IR (thin film) ν$_{max}$ 3508 (br), 2934, 1730, 1690, 1505, 1461, 1428, 1366, 1251, 1196, 1150, 1041, 977 cm$^{-1}$; $^1$H NMR (500 MHz, CDCl$_3$)

δ 7.22 (s, 1 H, ArH), 6.58 (s, 1 H, CH=C(CH$_3$)), 5.61 (d, J=47.0 Hz, 2 H, CH$_2$F), 5.55–5.50 (m, 1 H, CH=CHCH$_2$), 5.41–5.35 (m, 2 H, CH=CHCH$_2$ and CHOCO), 4.15 (ddd, J=10.0, 3.5, 3.0 Hz, 1 H, (CH$_3$)$_2$CCH(OH)), 3.75–3.73 (m, 1 H, CHOH(CHCH$_3$)), 3.24 (qd, J=7.0, 4.5 Hz, 1 H, CH$_3$CH(C=O)), 3.05 (d, J=4.0 Hz, 1 H, OH), 2.62 (d, J=4.0 Hz, 1 H, OH), 2.56 (dd, J=15.0, 10.5 Hz, 1 H, CH$_2$COO), 2.49 (dd, J=15.5, 2.5 Hz, 1 H, CH$_2$COO), 2.49–2.44 (m, 2 H), 2.20–2.13 (m, 1 H), 2.10 (s, 3 H, CH=C(CH$_3$)), 2.01–1.93 (m, 1 H), 1.67–1.56 (m, 2 H), 1.49–1.43 (m, 1 H), 1.31–1.17 (m, 2 H), 1.28 (s, 3 H, C(CH$_3$)$_2$), 1.18 (d, J=6.5 Hz, 3 H, CH$_3$CH(C=O)), 1.07 (s, 3 H, C(CH$_3$)$_2$), 0.98 (d, J=7.0 Hz, 3 H, CH$_3$CHCH$_2$); HRMS (FAB), calcd. for C$_{26}$H$_{38}$FNO$_5$S (M+Cs$^+$) 628.1509, found 628.1487.

Silyl ether 25 as illustrated in Scheme 7. To a solution of alcohol 13 (12.96 g, 54.4 mmol, 1.0 equiv.), in DMF (180 mL, 0.3 M) at 0° C., is added imidazole (10.2 g, 150.0 mmol, 2.8 equiv.) followed by tert-butyldimethylchlorosilane (13.5 g, 89.8 mmol, 1.7 equiv.). After warming to 25° C. over 7 h, the solvent is removed under reduced pressure and the resulting oil is partitioned between ether (200 mL) and saturated aqueous NH$_4$Cl (200 mL). The aqueous layer is extracted with ether (200 mL) and the combined organic extracts are washed with brine (550 mL), dried (MgSO$_4$) and concentrated under reduced pressure. Flash column chromatography (silica gel, 0 to 5% EtOAc in hexanes) furnishes silyl ether 25 as an oil (16.03 g, 84%). R$_f$=0.48 (hexanes); [α]$^{22}_D$ −17.5 (c 1.65, CHCl$_3$); IR (thin film) ν$_{max}$ 2928, 2857, 1472, 1361, 1278, 1252, 1082, 914, 836, 776, 677 cm$^{-1}$; $^1$H NMR (500 MHz, CDCl$_3$) δ6.15 (s, 1 H, CH=CCH$_3$), 5.74–5.66 (m, 1 H, CH=CH$_2$), 5.03 (bm, 1 H, CH=CH$_2$), 5.01 (s, 1 H, CH=CH$_2$), 4.16 (dd, J=6.5, 6.5 Hz, 1 H, CHOH), 2.25 (m, 1 H, CH$_2$=CHCH$_2$), 1.77 (s, 3 H, CH=CCH$_3$), 0.88 (s, 9 H, SiC(CH$_3$)$_3$), 0.04 (s, 3 H, Si(CH$_3$)$_2$), −0.01 (s, 3 H, Si(CH$_3$)$_2$);

Aldehyde 26 as illustrated in Scheme 7. To a solution of olefin 25 (16.0 g, 45.3 mmol, 1.0 equiv.) in a mixture of THF (206 mL), t-BuOH (206 mL) and H$_2$O (41 mL) at 0° C. is added 4-methylmorpholine N-oxide (NMO) (5.84 g, 49.8 mmol, 1.1 equiv.) followed by OsO$_4$ (5.2 mL, 2.5% w/v in t-BuOH, 0.453 mmol, 0.01 equiv.). The mixture is vigorously stirred 13 h at 25° C. and then quenched with saturated aqueous Na$_2$SO$_3$ (125 mL). The resulting solution is stirred for 2 h and then partitioned between EtOAc (150 mL) and water (150 mL). The organic phase is separated and the aqueous phase is extracted with EtOAc (2×200 mL). The combined organic extracts are dried (MgSO$_4$), filtered, and the solvents are removed under reduced pressure. Flash column chromatography (silica gel, 50 to 90% ether in hexanes) provides unreacted starting material (1.0 g, 6%) and the desired diols as a ca. 1:1 mixture of diastereoisomers (15.5 g, 89%). R$_f$=0.44 (silica gel, 50% EtOAc in hexanes); IR (thin film) ν$_{max}$ 3387, 2952, 2928, 1252, 1080, 837, 777 cm$^{-1}$; $^1$H NMR (500 MHz, CDCl$_3$) δ6.28 and 6.26 (singlets, 1 H total, CH=CCH$_3$), 4.47–4.42 (m, 1 H, CHOSi), 3.86–3.76 (m, 1 H, CHOH), 3.61–3.55 and 3.49–3.39 (m, 2 H total, CH$_2$OH), 3.33 and 3.15 (2 doublets, J=2.0 and 3.5 Hz, 1 H total, CHOH), 2.46 and 2.45 (triplets, J=5.5 and 5.5 Hz, CH$_2$OH), 1.78 and 1.76 (singlets, 3 H total), 1.63–1.60 and 1.58–1.53 (m, 2 H total, CH$_2$), 0.88 and 0.87 (singlets, 9 H total, SiC(CH$_3$)$_3$), 0.08 and 0.07 (singlets, 3 H total, Si(CH$_3$)$_2$), 0.01 and 0.00 (singlets, 3 H total, Si(CH$_3$)$_2$); HRMS (FAB), calcd. for C$_{13}$H$_{27}$IO$_3$Si (M+Na$^+$) 409.0672 found 409.0662.

The diols (obtained as described above) (23.3 g, 60.2 mmol, 1.0 equiv.) are dissolved in a mixture of MeOH (400 mL) and water (200 mL) and the solution is cooled to 0° C. NaIO$_4$ (77.2 g, 361.1 mmol, 6.0 equiv.) is then added portionwise over 5 min, and the resulting slurry is stirred vigorously for 30 min at 25° C. After completion of the reaction, the mixture is partitioned between CH$_2$Cl$_2$ (500 mL) and water (500 mL) and the organic phase is separated. The aqueous layer is extracted with CH$_2$Cl$_2$ (500 mL) and the combined organic extracts are washed with brine (1 L), dried (MgSO$_4$) and concentrated under reduced pressure. Flash column chromatography (silica gel, 17 to 50% ether in hexanes) provides aldehyde 26 as an oil (19.6 g, 92%). R$_f$=0.35 (silica gel, 20% ether in hexanes); [α]$^{22}_D$ −34.1 (c 2.8, CHCl$_3$); IR (thin film) ν$_{max}$ 2954, 2928, 2885, 2856, 1728, 1471, 1279, 1254, 1091, 838, 777, 677 cm$^{-1}$; $^1$H NMR (500 MHz, CDCl$_3$) δ9.73 (dd, J=2.5, 2.5 Hz, 1 H, CHO), 6.34 (s, 1 H, CH=CCH$_3$), 4.70 (dd, J=8.0, 4.0 Hz, 1 H, CHOSi), 2.68 (ddd, J=16.0, 8.3, 2.5 Hz, 1 H, (CHO)CH$_2$), 2.44 (ddd, J=16.0, 4.0, 2.5 Hz, 1 H, (CHO)CH$_2$), 1.80 (s, 3 H, CH=CCH$_3$), 0.85 (s, 9 H, SiC(CH$_3$)$_3$), 0.05 (s, 3 H, Si(CH$_3$)$_2$), 0.01 (s, 3 H, Si(CH$_3$)$_2$); HRMS (FAB), calcd. for C$_{12}$H$_{23}$IO$_2$Si (M+Na$^+$) 377.0410 found 377.0402.

Methyl ester 28 as illustrated in Scheme 7. A mixture of aldehyde 26 (19.6 g, 55.2 mmol, 1.0 equiv.) and stabilized ylide 27 (50.2 g, 134.0 mmol, 2.4 equiv.) [prepared from 4-bromo-1-butene by: (i) phosphonium salt formation; (ii) anion formation with KHMDS; and (iii) quenching with MeOC(O)Cl)] (see Marshall, J. A., et al., J. Org. Chem. 51,1735–1741 (1986) and Bestmann, H. J., Angew. Chem. Int. Ed. Engl. 1965, 645–60) in benzene (550 mL, 0.1 M) is heated at reflux for 1.5 h. After cooling to 25° C., the mixture is filtered and the solvent is removed under reduced pressure. Flash column chromatography (silica gel, 9 to 17% ether in hexanes) furnishes methyl ester 28 (24.5 g, 98%). R$_f$=0.37 (silica gel, 20% ether in hexanes); [α]$^{22}$−7.25 (c 1.6, CHCl$_3$); IR (thin film) ν$_{max}$ 3078, 2952, 2920, 2856, 1720, 1462, 1434, 1276, 1253, 1208, 1084, 836, 776, 672 cm$^{-1}$; $^1$H NMR (600 MHz, CDCl$_3$) δ6.81 (dd, J=7.4, 7.4 Hz, 1 H, CH=CCOOCH$_3$), 6.22 (s, 1 H, CH=CCH$_3$), 5.83–5.75 (m, 1 H, CH=CH$_2$), 4.99–4.98 (m, 1 H, CH=CH$_2$), 4.96 (m, 1 H, CH=CH$_2$), 4.22 (dd, J=7.5, 5.1 Hz, 1 H, CHOSi), 3.72 (s, 3 H, COOCH$_3$), 3.05 (d, J=6.0 Hz, 2 H, CH$_2$C(CO$_2$Me)), 2.40 (ddd, J=15.0, 7.5, 7.5 Hz, 1 H, CH$_2$CHOSi), 2.33 (ddd, J=15.0, 7.5, 5.1 Hz, 1 H, CH$_2$CHOSi), 1.77 (s, 3 H, CH=CCH$_3$), 0.85 (s, 9 H, SiC(CH$_3$)$_3$), 0.02 (s, 3 H, Si(CH$_3$)$_2$), −0.02 (s, 3 H, Si(CH$_3$)$_2$); HRMS (FAB), calcd. for C$_{18}$H$_{31}$IO$_3$Si (M+Cs$^+$), 583.0142 found 583.0159.

Allylic alcohol 29 as illustrated in Scheme 7. Methyl ester 28 (24.5 g, 54.3 mmol, 1.0 equiv.) is dissolved in THF (280 mL) and the solution is cooled to −78° C. DIBAL (163.0 mL, 1 M in CH$_2$Cl$_2$, 163.0 mmol, 3.0 equiv.) is added dropwise at −78° C. over 50 min, and the reaction mixture is stirred for a further 80 min. The reaction mixture is quenched with saturated aqueous sodium-potassium tartrate (150 mL) and the resulting mixture is allowed to warm up to 25° C. over 16 h. The organic layer is separated and the aqueous phase is extracted with ether (3×250 mL). The combined organic extracts are washed with brine (650 mL), dried (MgSO$_4$) and concentrated under reduced pressure. Flash column chromatography (silica gel, 17 to 50% ether in hexanes) furnishes alcohol 29 (22.9 g, 100%). R$_f$=0.11 (silica gel, 20% ether in hexanes); [α]$^{22}_D$ −7.25 (c 1.6, CHCl$_3$); IR (thin film) ν$_{max}$ 3346, 3078, 2954, 2928, 2857, 1637, 1471, 1361, 1276, 1252, 1078, 1005, 836, 775, 674, 558 cm$^{-1}$; $^1$H NMR (500 MHz, CDCl$_3$) δ6.16 (s, 1 H, CH=CCH$_3$), 5.81–5.73 (m, 1 H, CH=CH$_2$), 5.45 (dd, J=6.5, 6.5 Hz, 1 H, CH=CCH$_2$OH), 5.03 (m, 2 H, CH=CH$_2$), 4.16 (dd, J=6.5, 6.5 Hz, 1 H, CHOSi), 4.02 (d, J=4.5 Hz, 2 H, CH$_2$OH), 2.85 (dd, J=15.0, 5.1 Hz, 1

H, $CH_2CH=CH_2$), 2.84 (dd, J=15.0, 5.0 Hz, 1 H, $CH_2CH=CH_2$), 2.27 (ddd, J=15.0, 6.5, 6.5 Hz, 1 H, $CH_2$CHOSi), 2.25 (ddd, J=15.0, 6.5, 6.5 Hz, 1 H, $CH_2$CHOSi), 1.78 (s, 3 H, CH=CCH$_3$), 0.88 (s, 9 H, SiC(CH$_3$)$_3$), 0.02 (s, 3 H, Si(CH$_3$)$_2$), −0.02 (s, 3 H, Si(CH$_3$)$_2$); HRMS (FAB), calcd. for $C_{17}H_{31}IO_2Si$ (M+Cs$^+$), 555.0192 found 555.0177.

Triphenylmethyl ether 30 as illustrated in Scheme 7. Alcohol 29 (23.5 g, 55.7 mmol, 1.0 equiv.) is dissolved in DMF (300 mL, 0.15 M) and 4-DMAP (11.3 g, 92.5 mmol, 1.7 equiv.) and trityl chloride (22.1 g, 79.3 mmol, 1.4 equiv.) are added. The reaction mixture is stirred at 80° C. for 21 h, cooled to room temperature and the solvent is removed under reduced pressure. The resulting residue is purified by flash column chromatography to afford the required ether 30 as an oil (35.3 g, 95%). R$_f$=0.88 (silica gel, 20% ether in hexanes); $[\alpha]^{22}_D$ _0.74 (c 0.3, CHCl$_3$); IR (thin film) $v_{max}$ 3058, 2927, 2854, 1488, 1470, 1448, 1250, 1082, 836, 702, 632 cm$^{-1}$; $^1$H NMR (600 MHz, CHCl$_3$) δ7.45–7.43 (m, 5 H, Ph), 7.32–7.21 (m, 10 H, Ph), 6.19 (s, 1 H, CH=CCH$_3$), 5.61 (m, 2 H, CH=CH$_2$, CH=CH$_2$), 4.87 (m, 2 H, CH=CH$_2$, CH(C)CH$_2$OTr), 4.19 (dd, J=6.8, 6.8 Hz, 1 H, CHOSi), 3.46 (s, 2 H, CH$_2$OTr), 2.78 (dd, J=15.4, 6.7 Hz, 1 H, $CH_2CH=CH_2$), 2.73 (dd, J=15.4, 6.3 Hz, 1 H, $CH_2CH=CH_2$), 2.33 (ddd, J=14.5, 6.8, 6.8 Hz, 1 H, $CH_2$CHOSi), 2.31 (ddd, J=14.5, 6.8, 6.8 Hz, 1 H, $CH_2$CHOSi), 1.80 (s, 3 H, CH=CCH$_3$), 0.87 (s, 9 H, SiC(CH$_3$)$_3$), 0.04 (s, 3 H, Si(CH$_3$)$_2$), 0.00 (s, 3 H, Si(CH$_3$)$_2$); HRMS (FAB), calcd. for $C_{36}H_{45}IO_2Si$ (M+Cs$^+$), 797.1288 found 797.1309.

Alcohol 31 as illustrated in Scheme 7. Olefin 30 (35.3 g, 53.1 mmol, 1.0 equiv.) is dissolved in THF (53 mL, 1.0 M) and the solution is cooled to 0° C. 9-BBN (149 mL, 0.5 M in THF, 74.5 mmol, 1.4 equiv.) is added dropwise over 1.5 h, and the resulting mixture is stirred for 9 h at 0° C. Aqueous NaOH (106 mL of a 3 N solution, 319.0 mmol, 6.0 equiv.) is added, followed by aqueous $H_2O_2$ (32 mL, 30% w/w in water, 319.0 mmol, 6.0 equiv.). Stirring is continued for 1 h at 0° C., after which time the reaction mixture is diluted with ether (500 mL) and water (500 mL). The organic layer is separated and the aqueous phase is extracted with ether (2×500 mL). The combined organic extracts are washed with brine (1 L), dried (MgSO$_4$) and concentrated under reduced pressure. Flash column chromatography (silica gel, 9 to 50% ether in hexanes) furnishes primary alcohol 31 (34.6 g, 95%). R$_f$=0.54 (silica gel, 60% ether in hexanes); $[\alpha]^{22}_D$ −3.5 (c 0.2, CHCl$_3$); IR (thin film) $v_{max}$ 3380, 3058, 3032, 2926, 2855, 1489, 1449, 1278, 1251, 1078, 835, 706, 632 cm$^{-1}$; $^1$H NMR (500 MHz, CDCl$_3$) δ7.47–7.45 (m, 5 H, Ph), 7.32–7.22 (m, 10 H, Ph), 6.22 (s, 1 H, CH=CCH$_3$), 5.58 (dd, J=7.1, 7.1 Hz, 1 H, C=CHCH$_2$), 4.22 (dd, J=6.8, 6.0 Hz, 1 H, CHOSi), 3.52 (bm, 2 H, CH$_2$OH), 3.50 (s, 2 H, CH$_2$OTr), 2.33 (dd, J=14.5, 6.8, 6.8 Hz, 1 H, CH$_2$CHOSi), 2.28 (ddd, J=14.5, 6.8, 6.8 Hz, 1 H, CH$_2$CHOSi), 2.14 (m, 2 H, CH$_2$CH$_2$CH$_2$OH), 1.82 (s, 3 H, CH=CCH$_3$), 1.46 (m, 2 H, CH$_2$CH$_2$OH), 0.90 (s, 9 H, SiC(CH$_3$)$_3$), 0.06 (s, 3 H, Si(CH$_3$)$_2$), 0.02 (s, 3 H, Si(CH$_3$)$_2$); HRMS (FAB), calcd. for $C_{36}H_{47}IO_3Si$ (M+Cs$^+$), 815.1394 found 815.1430.

Iodide 32 as illustrated in Scheme 7. A solution of alcohol 31 (34.6 g, 50.73 mmol, 1.0 equiv.) in a mixture of ether (380 mL) and MeCN (127 mL) is cooled to 0° C. Imidazole (17.3 g, 253.7 mmol, 5.0 equiv.) and PPh$_3$ (33.3 g, 126.8 mmol, 2.5 equiv.) are then added and the mixture is stirred until all the solids have dissolved. Iodine (33.5 g, 131.9 mmol, 2.6 equiv.) is added and the mixture is stirred for 45 min at 0° C. The reaction is quenched by the addition of saturated aqueous Na$_2$S$_2$O$_3$ (150 mL) and the layers are separated. The aqueous phase is then extracted with ether (2×250 mL) and the combined organic extracts are washed with brine (750 mL), dried (MgSO$_4$) and concentrated under reduced pressure. Flash column chromatography (silica gel, 5 to 9% ether in hexanes) furnishes iodide 32 (39.2 g, 97%). R$_f$=0.88 (silica gel, 60% ether in hexanes); $[\alpha]^{22}_D$ −2.9 (c 2.6, CHCl$_3$); IR (thin film) $v_{max}$ 3057, 2926, 2855, 1481, 1448, 1251, 1083, 939, 836, 774, 706, 632 cm$^{-1}$; $^1$H NMR (500 MHz, CHCl$_3$) δ7.49–7.45 (m, 5 H, Ph), 7.33–7.23 (m, 10 H, Ph), 6.23 (s, 1 H, CH=CCH$_3$), 5.67 (dd, J=7.2, 7.1 Hz, 1 H, CH$_2$C=CH), 4.22 (dd, J=6.8, 6.8 Hz, 1 H, CHOSi), 3.51 (s, 2 H, CH$_2$OTr), 3.07 (dd, J=7.1, 7.0 Hz, 2 H, CH$_2$I), 2.34 (ddd, J=14.5 6.8, 6.8 Hz, 1 H, CH$_2$CHOSi), 2.25 (ddd, J=14.5, 6.8, 6.8 Hz, CH$_2$CHOSi), 2.13 (m, 2 H, CH$_2$CH$_2$CH$_2$I), 1.84 (s, 3 H, CH=CCH$_3$), 1.75 (m, 2 H, CH$_2$CH$_2$CH$_2$I), 0.90 (s, 9 H, SiC(CH$_3$)$_3$), 0.07 (s, 3 H, Si(CH$_3$)$_2$), 0.02 (s, 3 H, Si(CH$_3$)$_2$); HRMS (FAB), calcd. for $C_{36}H_{46}I_2O_2Si$ (M+Cs$^+$), 925.0411 found 925.0450.

Hydrazone 33 as illustrated in Scheme 7. Diisopropylamine (5.0 mL, 35.28 mmol, 1.4 equiv.) is added to a solution of n-BuLi (22.0 mL, 1.6 M in hexanes, 35.28 mmol, 1.4 equiv.) in 32 mL of THF at 0° C. and stirred for 1 h. The SAMP hydrazone of propionaldehyde (5.6 g, 32.76 mmol, 1.3 equiv.) in THF (16 mL), is added to this freshly prepared solution of LDA at 0° C. After stirring at that temperature for 16 h, the resulting yellow solution is cooled to −100° C., and a solution of iodide 32 (20.0 g, 25.23 mmol, 1.0 equiv.) in THF (32 mL) is added dropwise over a period of 2 h. The mixture is allowed to warm to −20° C. over 20 h, and then poured into saturated aqueous NH$_4$Cl (50 mL) and extracted with ether (3×100 mL). The combined organic extract is dried (MgSO$_4$), filtered and evaporated. Purification by flash column chromatography on silica gel (5 to 50% ether in hexanes) provides hydrazone 33 (15.0 g, 71%) as a yellow oil. R$_f$=0.63 (silica gel, 40% ether in hexanes); $[\alpha]^{22}_D$ −22.7 (c 0.2, CHCl$_3$); IR (thin film) $v_{max}$ 3057, 2927, 2854, 1489, 1448, 1251, 1078, 940, 836, 775, 706, 668, 632 cm$^{-1}$; $^1$H NMR (500 MHz, CHCl$_3$) δ7.46–7.44 (m, 5 H, Ph), 7.31–7.21 (m, 10 H, Ph), 6.40 (d, J=6.5 Hz, 1 H, N=CH), 6.21 (s, 1 H, CH=CCH$_3$), 5.50 (dd, J=7.0, 7,0 Hz, 1 H, CH$_2$C=CH), 4.20 (dd, J=6.0, 6.0 Hz, 1 H, CHOSi), 3.54 (dd, J=9.2, 3.5 Hz, 1 H, CH$_2$OCH$_3$), 3.45 (s, 2 H, CH$_2$OTr), 3.41 (dd, J=9.5, 7.0 Hz, 1 H, CH$_2$OCH$_3$), 3.37 (s, 3 H, CH$_2$OCH$_3$), 3.32–3.30 (m, 2 H, CH$_2$N), 2.60–2.55 (m, 1 H), 2.34–2.20 (m, 3 H), 2.04–1.95 (m, 1 H), 1.98–1.73 (m, 5 H), 1.82 (s, 3 H, CH=CCH$_3$), 1.38–1.21 (m, 4 H), 0.96 (d, J=6.9 Hz, 3 H, CHCH$_3$), 0.89 (s, 9 H, SiC(CH$_3$)$_3$), 0.06 (S, 3 H, Si(CH$_3$)$_2$), 0.01 (s, 3 H, Si(CH$_3$)$_2$; HRMS (FAB), calcd. for $C_{45}H_{63}IN_2O_3Si$ (M+Cs$^+$), 967.2707 found 967.2740.

Nitrile 34 as illustrated in Scheme 7. Monoperoxyphthalic acid magnesium salt (MMPP.6H$_2$O, 80%, 52.4 g, 84.8 mmol, 2.5 equiv.) is added portionwise over 10 min to a rapidly stirred solution of hydrazone 33 (28.3 g, 33.9 mmol, 1.0 equiv.) in a mixture of MeOH (283 mL), THF (100 mL) and pH 7 phosphate buffer (283 mL) at 0° C. The mixture is stirred at 0° C. for 1.5 h and then more THF (120 mL) is added in two portions over 30 min to help dissolve the starting material. After stirring for a further 1.5 h the reaction mixture is poured into saturated aqueous solution of NaHCO$_3$ (750 mL) and the product is extracted with ether (750 mL) and then EtOAc (2×750 mL). The combined organic extracts are washed with brine (1 L), dried (MgSO$_4$) and concentrated under reduced pressure. Flash column chromatography (silica gel, 9 to 20% ether in hexanes) furnishes nitrile 34 as a colorless oil (21.8 g, 89%). R$_f$=0.44 (silica gel, 20% ether in hexanes); $[\alpha]^{22}_D$ +2.9 (c 1.2, CHCl$_3$); IR (thin film) v$_{max}$ 3057, 2928, 2855, 2238, 1490, 1448, 1252, 1081, 836, 775, 707, 632 cm$^{-1}$; $^1$H NMR (500 MHz, CDCl$_3$) δ7.47–7.45 (m, 5 H, Ph), 7.33–7.23 (m, 10 H, Ph), 6.22 (s, 1 H, CH=CCH$_3$), 5.56 (dd, J=6.8, 6.8 Hz, 1 H, CH$_2$C=CH), 4.21 (dd, J=6.8, 6.8 Hz, 1 H, CHOSi), 3.49 (s, 2 H, CH$_2$OTr), 2.48 (m, 1 H, CH(CH$_3$)), 2.29 (ddd, J=14.5, 6.8, 6.8 Hz, 1 H, CH$_2$CHOSi), 2.24 (ddd, J=14.5, 6.8, 6.8 Hz, 1 H, CH$_2$CHOSi), 2.07 (m, 2 H, CH$_2$(C)CH$_2$OTr)), 1.82 (s, 3 H, CH=CCH$_3$), 1.58–1.23 (m, 4 H), 1.24 (d, J=7.0 Hz, 3 H, CHCH$_3$), 0.90 (s, 9 H, SiC(CH$_3$)$_3$), 0.07 (s, 3 H, Si(CH$_3$)$_2$), 0.0 (s, 3 H, Si(CH$_3$)$_2$); HRMS (FAB), calcd. for C$_{39}$H$_{50}$INO$_2$Si (M+Cs$^+$), 852.1710 found 852.1738.

Aldehyde 35 as illustrated in Scheme 7. Nitrile 34 (7.01 g, 9.74 mmol, 1.0 equiv.) is dissolved in toluene (195 mL, 0.05 M) and cooled to −78° C. DIBAL (29.2 mL, 1.0 M in toluene, 29.2 mmol, 3.0 equiv.) is added dropwise at −78° C. over 10 min. The reaction mixture is stirred at −78° C. until completion is verified by TLC (1 h). Methanol (10 mL) and HCl (10 mL, 1.0 N in water) are sequentially added and the resulting mixture is brought up to 0° C. over 1 h. Ether (250 mL) and water (250 mL) are added and the layers are separated. The aqueous phase is extracted with ether (2×250 mL) and the combined organic extracts are washed with brine (500 mL), dried (MgSO$_4$) and concentrated under reduced pressure. Flash column chromatography (silica gel, 17 to 33% ether in hexanes) affords aldehyde 35 as an oil (6.18 g, 88%). R$_f$=0.51 (silica gel, 20% ether in hexanes); [α]$^{22}{}_D$ +2.0 (c 0.3, CHCl$_3$); IR (thin film) v$_{max}$ 3057, 2927, 2855, 1726, 1490, 1448, 1251, 1081, 836, 775, 707, 632 cm$^{-1}$; $^1$H NMR (500 MHz, CDCl$_3$) δ9.51 (d, J=1.9 Hz, 1 H, CHO), 7.46–7.45 (m, 5 H, Ph), 7.32–7.22 (m, 10 H, Ph), 6.20 (s, 1 H, CH=CCH$_3$), 5.54 (dd, J=7.0, 7.0 Hz, 1 H, CH$_2$C=CH), 4.20 (dd, J=6.5, 6.0 Hz, 1 H, CHOSi), 3.47 (s, 2 H, CH$_2$OTr), 2.34–2.20 (m, 3 H, CH$_2$CHOSi and CH(CH$_3$)), 2.04 (m, 2 H, CH$_2$(C)CH$_2$OTr), 1.82 (s, 3 H, CH=CCH$_3$), 1.66 (m, 1 H), 1.30–1.19 (m, 3 H), 1.02 (d, J=7.0 Hz, 3 H, CHCH$_3$), 0.89 (s, 9 H, SiC(CH$_3$)$_3$), 0.06 (s, 3 H, Si(CH$_3$)$_2$), 0.00 (s, 3 H, Si(CH$_3$)$_2$); HRMS (FAB), calcd. for C$_{39}$H$_{51}$IO$_3$Si (M+Cs$^+$), 855.1707 found 855.1672.

tris-(Silylethers) 37 and 38 as illustrated in Scheme 8. A solution of ketone 36 (see Nicolaou, K. C., et al., J. Am. Chem. Soc. 119, 7974–91 (1997) (1.20 g, 2.99 mmol, 1.4 equiv.) in THF (4.3 mL) is added dropwise over 5 min to a freshly prepared solution of LDA [diisopropylamine (424 μL, 3.03 mmol, 1.45 equiv.) is added to n-BuLi (2.00 mL, 1.52 M in hexanes, 3.04 mmol, 1.45 equiv.) at 0° C., and after 5 min THF (4.3 mL) is added] at −78° C. After stirring for 1.5 h at −78° C., the solution is allowed to warm up to 40° C. over a period of 30 min. The reaction mixture is then cooled to −78° C., and a solution of aldehyde 35 (1.51 g, 2.09 mmol, 1.0 equiv.) in THF (12.5 mL) is added dropwise over 15 min. The resulting mixture is stirred for 1 h at −78° C., and then quenched by dropwise addition of saturated aqueous AcOH (3.1 mL of a 1 M solution in THF, 3.10 mmol, 1.5 equiv.). The mixture is then warmed to 25° C. and partitioned between ether (25 mL) and saturated aqueous NH$_4$Cl (25 mL). The aqueous phase is extracted with ether (3×25 mL) and the combined organic extracts are dried (MgSO$_4$) and concentrated under reduced pressure. Flash column chromatography (silica gel, 4 to 20% ether in hexanes) provides unreacted ketone (502 mg, 42%), undesired aldol product 38 (705 mg, 27%) and a mixture of desired aldol product 37 and unreacted aldehyde 35 [1.136 g, (ca. 9:1 ratio of 37:35 by $^1$H NMR)] (i.e. 39% yield of 37). This mixture is used directly in the next step. 37: (major) (obtained as a colorless oil from a mixture containing 35, by flash column chromatography silica gel, (10 to 17% EtOAc in hexanes). R$_f$=0.22 (silica gel, 10% ether in hexanes); [α]$^{22}{}_D$ −20.0 (c 0.3, CHCl$_3$); IR (thin film) v$_{max}$ 3486, 2954, 2928, 2856, 1682, 1472, 1448, 1253, 1090, 994, 836, 775, 706, 668, 632 cm$^{-1}$; $^1$H NMR (600 MHz, CDCl$_3$) δ7.45–7.43 (m, 5 H, Ph), 7.30–7.19 (m, 10 H, Ph) 6.19 (sm 1 H, CH=CCH$_3$), 5.51 (dd, J=7.0, 6.9 Hz, 1 H, C=CHCH$_2$), 4.18 (dd, J=6.3, 6.2 Hz, 1 H, CHOSi), 3.88 (dd, J=7.5, 2.6 Hz, 1 H, CHOSi), 3.65 (m, 1 H, CH$_2$OSi), 3.59 (m, 1 H, CH$_2$OSi), 3.46 (d, J=11.2 Hz, 1 H, CH$_2$OTr), 3.43 (d, J=11.2 Hz, 1 H, CH$_2$OTr), 3.27 (m, 1 H, CH$_3$CH (C=O)), 3.22 (d, J=9.3 Hz, 1 H, CHOH), 2.32–2.18 (m, 2 H, C=CHCH$_2$CHOSi) 2.00 (m, 2 H, CH$_2$(C)CH$_2$OTr), 1.80 (s, 3 H, CH=C(CH$_3$)), 1.66 (m, 2 H), 1.46 (m, 2 H), 1.27 (m, 1 H, CH(CH$_3$), 1.19 (s, 3 H, C(CH$_3$)$_2$), 1.07 (s, 3 H, C(CH$_3$)$_2$), 0.99 (d, J=6.8 Hz, 3 H, CH(CH$_3$)), 0.89 (s, 9 H, SiC(CH$_3$)$_3$), 0.87 (s, 9 H, SiC(CH$_3$)$_3$), 0.86 (s, 9 H, SiC (CH$_3$)$_3$), 0.71 (d, J=6.7 Hz, 3 H, CH(CH$_3$)), 0.10 (s, 3 H, Si(CH$_3$)$_2$), 0.07 (s, 3 H, Si(CH$_3$)$_2$), 0.04 (s, 3 H, Si(CH$_3$)$_2$), 0.03 (s, 6 H, Si(CH$_3$)$_2$), −0.01 (s, 3 H, Si(CH$_3$)$_2$); HRMS (FAB), calcd. for C$_{60}$H$_{97}$IO$_6$Si$_3$ (M+Cs$^+$), 1257.4692 found 1257.4639. 38: (minor) Colorless oil; R$_f$=0.38 (silica gel, 20% ether in hexanes); [α]$^{22}{}_D$ −11.9 (c 2.9, CHCl$_3$); IR (thin film) v$_{max}$ 3501, 2954, 2930, 2856, 1682, 1469, 1254, 1088, 836, 776, 705, 670 cm$^{-1}$; $^1$H NMR (500 MHz, CHCl$_3$) δ7.46–7.44 (m, 5 H, Ph), 7.31–7.21 (m, 10 H, Ph), 6.21 (s, 1 H, CH=CCH$_3$), 5.52 (dd, J=7.0, 6.9Hz, 1 H, C=CHCH$_2$), 4.20 (dd, J=6.5, 6.5 Hz, 1 H, CHOSi), 3.88 (dd, J=7.5, 2.5 Hz, 1 H, CHOSi), 3.67 (m, 1 H, CH$_2$OSi), 3.60 (m, 1 H, CH$_2$OSi), 3.46 (s, 2 H, CH$_2$OTr), 3.30–3.21 (m, 2 H, CHOH, CH$_3$CH(C=O)), 2.30–2.25 (m, 2 H, C=CHCH$_2$CHOSi), 2.05–1.93 (m, 2 H, CH$_2$C(CH$_2$OTr)=CH), 1.81 (s, 3 H, CH=C(CH$_3$)), 1.63 (m, 1 H, CH(CH$_3$), 1.45 (m, 2 H), 1.24 (m, 2 H), (s, 3 H, C(CH$_3$)$_2$), 1.05 (s, 3 H, C(CH$_3$)$_2$), 1.01 (d, J=6.9 Hz, 3 H, CH(CH$_3$)), 0.92 (s, 18 H, SiC(CH$_3$)$_3$), 0.89 (s, 9 H, SiC(CH$_3$)$_3$), 0.88 (obscured d, 3 H, CH(CH$_3$)), 0.88 (s, 18 H, SiC(CH$_3$)$_3$), 0.11 (s, 3 H, Si(CH$_3$)$_2$), 0.07 (s, 3 H, Si(CH$_3$)$_2$), 0.06 (s, 3 H, Si(CH$_3$)$_2$), 0.04 (s, 6 H, Si(CH$_3$)$_2$), 0.01 (s, 3 H, Si(CH$_3$)$_2$); HRMS (FAB), calcd. for C$_{60}$H$_{97}$IO$_6$Si$_3$ (M+Cs$^+$), 1257.4692 found 1257.4749.

tetra-(Silylether) 39 as illustrated in Scheme 8. Alcohol 37 (1.136 g of a 9:1 mixture with aldehyde 35, 0.933 mmol, 1.0 equiv.) is dissolved in CH$_2$Cl$_2$ (5.0 mL), cooled to −20° C. and treated with 2,6-lutidine (470 μL, 4.04 mmol, 4.3 equiv.) and tert-butyldimethylsilyl trifluoromethanesulfonate (695 μL, 3.03 mmol, 3.2 equiv.). The mixture is then stirred for 2.5 h with slow warming to 0° C. The reaction is then quenched with saturated aqueous NaHCO$_3$ (25 mL) and the aqueous phase is extracted with ether (3×25 mL). The combined organic extracts are washed with brine (250 mL), dried (MgSO$_4$) and concentrated under reduced pressure. Flash column chromatography (silica gel, 4 to 9% ether in hexanes) furnishes tetra-(silylether) 39 as a colorless oil (1.04 g, 90%). R$_f$=0.91 (silica gel, 20% ether in hexanes); [α]$^{22}{}_D$ −16.8 (c 0.7, CHCl$_3$); IR (thin film) v$_{max}$ 3058, 2951, 2856, 1693, 1471, 1253, 1079, 1004, 836, 706 cm$^{-1}$; $^1$H NMR (600 MHz, CDCl$_3$) δ7.46–7.43 (m, 5 H, Ph), 7.29–7.19 (m, 10 H, Ph), 6.19 (s, 1 H, CH=CCH$_3$), 5.49 (dd, J=7.0, 7.0 Hz, 1 H, C=CHCH$_2$), 418 (dd, J=6.3, 6.1 Hz, 1 H, CHOSi), 3.85 (dd, J=7.6, 2.5 Hz, 1 H, CHOSi), 3.70 (dd, J=6.7, 2.0 Hz, 1 H, CHOSi), 3.67 (ddd, J=9.6, 4.8, 4.8 Hz, 1 H, CH$_2$OSi), 3.59 (ddd, J=9.7, 7.9. 7.9 Hz, 1 H, CH$_2$OSi), 3.45 (d, J=11.2 Hz, 1 H, CH$_2$OTr), 3.42 (d, J=11.2 Hz, 1 H, CH$_2$OTr), 3.08 (qd, J=6.8, 6.8 Hz, 1 H, CH$_3$CH (C=O)), 2.27 (ddd, J=14.4, 7.2, 7.2 Hz, 1 H, C=CHCH$_2$CHOSi), 2.23 (ddd, J=14.5, 6.2, 6.2 Hz, 1 H, C=CHCH$_2$CHOSi), 1.97 (m, 2 H, CH$_2$C(CH$_2$OTr)=CH), 1.79 (s, 3 H, CH=C(CH$_3$)), 1.57 (m, 1 H), 1.46 (m, 1 H), 1.25 (m, 3 H), 1.17 (s, 3 H, C(CH$_3$)$_2$), 1.01 (d, J=6.8 Hz, 3 H, CH(CH$_3$)), 0.95 (s, 3 H, C(CH$_3$)$_2$), 0.87 (s, 18 H, SiC(CH$_3$)$_3$), 0.86 (s, 18 H, SiC(CH$_3$)$_3$), 0.09–-0.03 (m, 24 H, Si(CH$_3$)$_2$); HRMS (FAB), calcd. for C$_{66}$H$_{111}$IO$_6$Si$_4$ (M+Cs$^+$), 1371.5557 found 1371.5523.

Alcohol 40 as illustrated in Scheme 8. To a solution of tetra-silyl ether 39 (180 mg, 0.145 mmol) in THF (1.5 mL) at 0° C. is added HF·pyr. in pyridine/THF mixture (prepared from a stock solution containing 420 μL HF.pyridine, 1.14 mL pyridine and 2.00 mL THF) (1.5 mL) and the resulting solution is stirred for 2 h at 0° C. More HF.pyr. in pyridine/THF mixture (0.5 mL) is then added and stirring is continued for additional 1 h at 0° C. The reaction is quenched by careful addition of saturated aqueous NaHCO$_3$ and the product is extracted with EtOAc (3×25 mL). The combined organic extracts are then dried (MgSO$_4$) and concentrated under reduced pressure. Flash chromatography (silica gel 30% ether in hexanes) furnishes alcohol 40 as a pale yellow oil (137 mg, 84%). R$_f$=0.36 (silica gel, 40% ether in hexanes); [α]$^{22}_D$ –26.0 (c 0.3, CHCl$_3$); IR (thin film) ν$_{max}$ 3422, 2928, 2855, 1690, 1490. 1471, 1448, 1360, 1252, 1086, 1004, 986, 836, 774, 706 cm$^{-1}$; $^1$H NMR (600 MHz, CDCl$_3$) δ7.44–7.42 (m, 5 H, Ph), 7.29–7.20 (m, 10 H, Ph), 6.19 (s, 1 H, CH=CCH$_3$), 5.49 (dd, J=7.1, 7.1 Hz, 1 H, C=CHCH$_2$), 4.17 (dd, J=6.2, 6.0 Hz, 1 H, CHOSi), 4.03 (dd, J=6.6, 3.7 Hz, 1 H, CHOSi), 3.73 (dd, J=7.2, 1.7 Hz, 1 H, CHOSi), 3.65 m, 2 H, CH$_2$OH), 3.45 (d, J=11.7 Hz, 1 H, CH$_2$OTr), 3.42 (d, J=11.7 Hz, 1 H, CH$_2$OTr), 3.06 (qd, J=6.9, 6.9 Hz, 1 H, CH$_3$CH(C=O)), 2.28 (ddd, J=14.7, 7.3, 7.3 Hz, 1 H, C=CHCH$_2$CHOSi), 2.22 (ddd, J=14.7, 6.3, 6.3 Hz, 1 H, C=CHCH$_2$CHOSi), 1.98 (m, 2 H, CH$_2$C(CH$_2$OTr)=CH), 1.79 (s, 3 H, CH=C(CH$_3$)), 1.56 (m, 2 H), 1.24 (m, 3 H), 1.18 (s, 3 H, C(CH$_3$)$_2$), 1.03 (d, J=6.9 Hz, 3 H, CH(CH$_3$)), 0.97 (s, 3 H, C(CH$_3$)$_2$), 0.87 (3 singlets, 27 H, SiC(CH$_3$)$_3$), 0.81 (d, J=6.7 Hz, 3 H, CH(CH$_3$)), 0.10 (s, 3 H, Si(CH$_3$)$_2$), 0.04 (s, 9 H, Si(CH$_3$)$_2$), 0.03 (s, 3 H, Si(CH$_3$)$_2$), 0.00 (s, 3 H, Si(CH$_3$)$_2$); HRMS (FAB), calcd. for C$_{60}$H$_{97}$IO$_6$Si$_3$ (M+Cs$^+$), 1257.4692 found 1257.4780.

Aldehyde 41 as illustrated in Scheme 8. To a solution of oxalyl chloride (150 μL, 1.72 mmol, 2.0 equiv.) in CH$_2$Cl$_2$ (10 mL) at –78° C. is added dropwise DMSO (247 μL, 3.48 mmol, 4.0 equiv.). After stirring for 10 min at –78° C., a solution of alcohol 40 (960 mg, 0.853 mmol, 1.0 equiv.) in CH$_2$Cl$_2$ (10 mL) is added dropwise. The resulting solution is stirred at –78° C. for 1 h, and then Et$_3$N (714 μL, 5.12 mmol, 6.0 equiv.) is added and the reaction mixture is allowed to warm up to 25° C. over 30 min. Water (30 mL) is added, and the product is extracted with ether (3×40 mL). The combined organic extracts are dried (MgSO$_4$) and then concentrated under reduced pressure. Flash column chromatography (silica gel, 17 to 50% ether in hexanes) furnishes aldehyde 41 as a colorless oil (943 mg, 98%). R$_f$=0.74 (silica gel, 40% ether in hexanes); [α]$^{22}_D$ –10.8 (c 0.1, CHCl$_3$); IR (thin film) ν$_{max}$ 2928, 2855, 1728, 1690, 1471, 1448, 1260, 1252, 1085, 987, 836, 774, 706 cm$^{-1}$; $^1$H NMR (600 MHz, CDCl$_3$) δ9.74 (dd, J=2.4, 1.5 Hz, 1 H, CHO), 7.44–7.42 (m, 5 H, Ph), 7.29–7.20 (m, 10 H, Ph), 6.19 (s, 1 H, CH=CCH$_3$), 5.49 (dd, J=7.0, 6.8 Hz, 1 H, C=CHCH$_2$), 4.44 (dd, J=6.3, 5.0 Hz, 1 H, CHOSi), 4.18 (dd, J=6.9, 6.4 Hz, 1 H, CHOSi), 3.70 (dd, J=7.2, 1.8 Hz, 1 H, CHOSi), 3.45 (d, J=11.4 Hz, 1 H, CH$_2$OTr), 3.42 (d, J=11.4 Hz, 1 H, CH$_2$OTr), 3.05 (qd, J=7.0, 7.0 Hz, 1 H, CH$_3$CH(C=O)), 2.49 (ddd, J=17.0, 4.5, 1.4 Hz, CH$_2$CHO), 2.38 (ddd, J=17.0, 5.4, 2.8 Hz, 1 H, CH$_2$CHO), 2.27 (ddd, J=14.0, 7.1, 7.1 Hz, 1 H, C=CHCH$_2$CHOSi), 2.23 (ddd, J=14.5, 6.5, 6.5 Hz, 1 H, C=CHCH$_2$CHOSi), 1.98 (m, 2 H, CH$_2$C(CH$_2$OTr)=CH), 1.79 (s, 3 H, CH=C(CH$_3$)), 1.27 (m, 4 H), 1.19 (s, 3 H, C(CH$_3$)$_2$), 1.12 (m, 1 H), 1.00 (d, J=6.8 Hz, 3 H, CH(CH$_3$)), 0.98 (s, 3 H, C(CH$_3$)$_2$), 0.87 (s, 27 H, Si(CH$_3$)$_3$), 0.80 (d, J=6.7 Hz, 3 H, CH(CH$_3$)), 0.07 (s, 3 H, Si(CH$_3$)$_2$), 0.04 (s, 3 H, Si(CH$_3$)$_2$), 0.03 (s, 3 H, Si(CH$_3$)$_2$), 0.03 (s, 3 H, Si(CH$_3$)$_2$), 0.02 (s, 3 H, Si(CH$_3$)$_2$), 0.00 (s, 3 H, Si(CH$_3$)$_2$); HRMS (FAB), calcd. for C$_{60}$H$_{95}$IO$_6$Si$_3$ (M+Cs$^+$), 1255.4536 found 1255.4561.

Carboxylic acid 42 as illustrated in Scheme 8. To a solution of aldehyde 41 (943 mg, 0.839 mmol, 1.0 equiv.) in t-BuOH (38.5 mL) and H$_2$O (8.4 mL) is added 2-methyl-2-butene (31.5 mL, 2 M in THF, 63.0 mmol, 75 equiv.) and NaH$_2$PO$_4$ (250 mg, 2.08 mmol, 2.5 equiv.) followed by NaClO$_2$ (380 mg, 4.20 mmol, 5.0 equiv.) and the resulting mixture is stirred at 25° C. for 40 min. The volatiles are then removed under reduced pressure and the residue is partitioned between EtOAc (40 mL) and brine (40 mL) and the layers are separated. The aqueous phase is then extracted with EtOAc (3×40 mL), and the combined organic extracts are dried (MgSO$_4$) and then concentrated under reduced pressure. Flash column chromatography (silica gel, 60% ether in hexanes) furnishes carboxylic acid 42 as an oil (956 mg, 100%). R$_f$=0.47 (silica gel, 40% ether in hexanes); [α]$^{22}_D$ –19.6 (c 0.2, CHCl$_3$); IR (thin film) ν$_{max}$ 3389, 2930, 2856, 1711, 1469, 1254, 1085, 988, 835, 775, 705 cm$^{-1}$; $^1$H NMR (600 MHz, CDCl$_3$) δ7.44–7.43 (m, 5 H, Ph), 7.29–7.20 (m, 10 H, Ph), 6.19 (s, 1 H, CH=CCH$_3$), 5.49 (dd, J=7.3, 7.1 Hz, 1 H, C=CHCH$_2$), 4.34 (dd, J=6.4, 3.3 Hz, 1 H, CHOSi), 4.18 (dd, J=6.2, 6.2 Hz, 1 H, CHOSi), 3.72 (dd, J=7.2, 1.7 Hz, 1 H, CHOSi), 3.45 (d, J=11.4 Hz, 1 H, CH$_2$OTr), 3.41 (d, J=11.4 Hz, 1 H, CH$_2$OTr), 3.07 (qd, J=7.0, 7.0 Hz, 1 H, CH$_3$CH(C=O)), 2.46 (dd, J=16.3, 3.1 Hz, 1 H, CH$_2$CO$_2$H), 2.32–2.18 (m, 3 H, CH$_2$CO$_2$H and C=CHCH$_2$CHOSi), 1.97 (m, 2 H, CH$_2$C(CH$_2$OTr)=CH), 1.80 (s, 3 H, CH=C(CH$_3$)), 1.31–1.19 (m, 5 H), 1.19 (s, 3 H, C(CH$_3$)$_2$), 1.02 (d, J=6.9 Hz, 3 H, CH(CH$_3$)), 0.99 (s, 3 H, C(CH$_3$)$_2$), 0.87 (s, 27 H, Si(CH$_3$)$_3$), 0.80 (d, J=6.8 Hz, 3 H, CH(CH$_3$)), 0.07, (s, 3 H, Si(CH$_3$)$_2$), 0.04 (s, 3 H, Si(CH$_3$)$_2$), 0.04 (s, 3 H, Si(CH$_3$)$_2$), 0.03 (s, 3 H, Si(CH$_3$)$_2$), 0.03 (s, 3 H, Si(CH$_3$)$_2$), 0.02 (s, 3 H, Si(CH$_3$)$_2$), 0.00 (s, 3 H, Si(CH$_3$)$_2$); HRMS (FAB), calcd. for C$_{60}$H$_{95}$IO$_7$Si$_3$ (M+Cs$^+$), 1271.4485 found 1271.4550.

Hydroxy acid 43 as illustrated in Scheme 8. A solution of carboxylic acid 42 (956 mg, 0.839 mmol, 1.0 equiv.) in THF (17 mL) at 0° C. is treated with TBAF (5.0 mL, 1.0 M in THF, 5.00 mmol, 6.0 equiv.) and the mixture is allowed to warm to 25° C. over 19 h. The reaction is then quenched by the addition of saturated aqueous NH$_4$Cl (40 mL) and the product is extracted with EtOAc (3×40 mL). The combined organic extracts are dried (MgSO$_4$) and concentrated under reduced pressure. Flash column chromatography (silica gel, 5% MeOH in CH$_2$Cl$_2$) furnishes hydroxy acid 43 as a yellow oil (817 mg, 95%). R$_f$=0.27 (silica gel, 5% MeOH in CH$_2$Cl$_2$); [α]$^{22}_D$ –1.4 (c 0.2, CHCl$_3$); IR (thin film) ν$_{max}$ 3364, 3057, 2938, 2856, 1712, 1694, 1469, 1254, 1086, 1053, 988, 836, 776, 734, 705 cm$^{-1}$; $^1$H NMR (600 MHz, CDCl$_3$) δ7.43–7.42 (m, 5 H, Ph), 7.30–7.21 (m, 10 H, Ph), 6.32 (s, 1 H, CH=CCH$_3$), 5.46 (dd, J=7.2, 7.2 Hz, 1 H, C=CHCH$_2$), 4.35 (dd, J=6.3, 3.2 Hz, 1 H, CHOH), 4.21 (dd, J=6.4, 6.3 Hz, 1 H, CHOSi), 3.73 (dd, J=7.3, 1.2 Hz, 1 H, CHOSi), 3.52 (d, J=12.1 Hz, 1 H, CH$_2$OTr), 3.48 (d, J=12.1 Hz, 1 H, CH$_2$OTr), 3.06 (m, 2 H, CH$_3$CH(C=O) and OH), 2.45 (dd, J=16.4, 3.0 Hz, 1 H, CH$_2$CO$_2$H), 2.35 (m, 2 H, C=CHCH$_2$CHOH), 2.29 (dd, J=16.4, 6.5 Hz, 1 H, CH$_2$CO$_2$H), 2.07–1.94 (m, 2 H, CH$_2$C(CH$_2$OTr)=CH), 1.85 (s, 3 H, CH=C(CH$_3$)), 1.71 (m, 1 H), 1.39 (m, 1 H), CH(CH$_3$)), 1.27 (m, 3 H), 1.18 (s, 3 H, C(CH$_3$)$_2$), 1.02

(obscured d, 3 H, CH(CH$_3$)), 1.02 (s, 3 H, C(CH$_3$)$_2$), 0.87 (s, 18 H, Si(CH$_3$)$_3$), 0.81 (d, J=6.8 Hz, 3 H, CH(CH$_3$)), 0.09 (s, 3 H, Si(CH$_3$)$_2$), 0.07 (s, 3 H, Si(CH$_3$)$_2$), 0.04 (s, 3 H, Si(CH$_3$)$_2$), 0.02 (s, 3 H, Si(CH$_3$)$_2$); HRMS (FAB), calcd. for C$_{54}$H$_{81}$IO$_7$Si$_2$ (M+Cs$^+$), 1157.3620 found 1157.3669.

Macrolactone 44 as illustrated in Scheme 8: To a solution of hydroxy acid 43 (1.06 g, 1.04 mmol, 1.0 equiv.) in THF (15 mL, 0.07 M) is added Et$_3$N (870 μL 0.24 mmol, 6.0 equiv.) and 2,4,6-trichlorobenzoyl chloride (390 μL, 2.50 mmol, 2.4 equiv.). The reaction mixture is stirred at 0° C. for 1.5 h, and then added slowly over a period of 2 h via syringe pump to a solution of 4-DMAP (280 mg, 2.29 mmol, 2.2 equiv.) in toluene (208 mL, 0.005 M based on 43) at 75° C. The mixture is stirred at that temperature for an additional 0.5 h and is then concentrated under reduced pressure. The resulting residue is filtered through a plug of silica gel eluting with 50% ether in hexanes. Flash column chromatography (silica gel, 17% ether in hexanes) furnishes macrolactone 44 as a colorless foam (877 mg, 84%). R$_f$=0.19 (10% ether in hexanes); [α]$^{22}{}_D$ −7.4 (c 0.2, CHCl$_3$); IR (thin film) ν$_{max}$ 2929, 2855, 1742, 1695, 1468, 1381, 1253, 1156, 1065, 985, 834, 774, 733, 706 cm$^{-1}$; $^1$H NMR (600 MHz, CDCl$_3$) δ7.44–7.42 (m, 5 H, Ph), 7.29–7.20 (m, 10 H, Ph), 6.39 (s, 1 H, CH=CCH$_3$), 5.51 (dd, J=9.5, 6.8 Hz, 1 H, C=CHCH$_2$), 5.07 (d, J=9.3 Hz, 1 H, CHOCO), 4.02 (d, J=9.2 Hz, 1 H, CHOSi), 3.82 (d, J=8.9 Hz, 1 H, CHOSi), 3.46 (d, J=11.5 Hz, 1 H, CH$_2$OTr), 3.42 (d, J=11.5 Hz, 1 H, CH$_2$OTr), 2.95 (dq, J=8.7, 7.0 Hz, 1 H, CH$_3$CH(C=O)), 2.72 (m, 2 H, C=CHCH$_2$CHO and CH$_2$COO), 2.54 (dd, J=16.2, 9.7 Hz, 1 H, CH$_2$COO), 2.29 (m, 1 H, C=CHCH$_2$CHO), 2.12 (dd, J=14.3, 5.1 Hz, 1 H, CH$_2$C(CH$_2$OTr)=CH), 1.98 (m, CH$_2$C(CH$_2$OTr)=CH), 1.88 (s, 3 H, CH=C(CH$_3$)), 1.44–1.23 (m, 5 H), 1.18 (s, 3 H, C(CH$_3$)$_2$), 1.10 (s, 3 H, C(CH$_3$)$_2$), 1.07 (d, J=6.8 Hz, 3 H, CH(CH$_3$)), 0.92 ((s, 9 H, Si(CH$_3$)$_3$), 0.82 (d, J=6.9 Hz, 3 H, CH(CH$_3$)), 0.72 (s, 9 H, Si(CH$_3$)$_3$), 0.08 (s, 3 H, Si(CH$_3$)$_2$), 0.05 (s, 3 H, Si(CH$_3$)$_2$), 0.05 (s, 3 H, Si(CH$_3$)$_2$), −0.32 (s, 3 H, Si(CH$_3$)$_2$); HRMS (FAB), cald. for C$_{54}$H$_{79}$IO$_6$Si$_2$ (M+Cs$^+$), 1139.3514 found 1139.3459.

Triol 24 as illustrated in Scheme 8. To a solution of macrolactone 44 (608 mg, 0.604 mmol, 1.0 equiv.) in THF (45 mL) at 0° C. is added HF.pyr. (15 mL). The resulting mixture is allowed to warm up to 25° C. over 15 h and is then cooled to 0° C. and quenched by careful addition of saturated aqueous NaHCO$_3$ (50 mL). The product is then extracted with EtOAc (3×50 mL), and the combined organic extracts are dried (MgSO$_4$) and then concentrated under reduced pressure. Flash column chromatography (silica gel, 60% EtOAc in hexanes) furnishes triol 24 as a colorless foam (280 mg, 86%). R$_f$=0.32 (silica gel, 60% EtOAc in hexanes); [α]$^{22}{}_D$ −32.1 (c 0.2, CHCl$_3$); IR (thin film) ν$_{max}$ 3413, 2923, 2857, 1731, 1686, 1461, 1379, 1259, 1148, 1046, 737 cm$^{-1}$; $^1$H NMR (600 MHz, CDCl$_3$) δ6.43 (s, 1 H, CH=CCH$_3$), 5.38 (dd, J=9.7, 5.4 Hz, 1 H, C=CHCH$_2$), 5.29 (dd, J=8.8, 1.9 Hz, 1 H, CHOCO), 4.08 (m, 1 H, CHOH), 4.06 (d, J=13.0 Hz, 1 H, CH$_2$OH), 4.00 (d, J=13.0 Hz, 1 H, CH$_2$OH), 3.69 (dd, J=3.5. 3.4Hz, 1 H, CHOH), 3.12 (qd, J=6.9, 3.1 Hz, 1 H, CH$_3$CH(C=O)), 2.76 (bs, 1 H, OH), 2.67 (ddd, J=15.0, 9.7, 9.7 Hz, 1 H, C=CHCH$_2$CHO), 2.45 (dd, J=15.4, 10.6 Hz, 1 H, CH$_2$COO), 2.38 (bs, 1 H, OH), 2.33 (dd, J=15.4, 3.0 Hz, 1 H, CH$_2$COO), 2.21 (m, 2 H, CH$_2$C(CH$_2$OH)=CH), 2.06 (m, 1 H, C=CHCH$_2$CHO), 1.87 (s, 3 H, CH=C(CH$_3$)), 1.71 (m, 1 H), 1.66 (m, 1 H), 1.32 (s, 3 H, C(CH$_3$)$_2$), 1.29–1.24 (m, 3 H), 1.17 (d, J=6.9 Hz, 3 H, CH(CH$_3$)), 1.08 (s, 3 H, C(CH$_3$)$_2$), 0.99 (d, J=7.0 Hz, 3 H, CH(CH$_3$)); HRMS (FAB), calcd. for C$_{23}$H$_{37}$IO$_6$ (M+Cs$^+$), 669.0689 found 669.0711.

Macrolactone 45 as illustrated in Scheme 9. A solution of vinyl iodide 24 (55 mg, 0.103 mmol, 1.0 equiv.), stannane 8j (84 mg, 0.207 mmol, 2.0 equiv.) and PdCl$_2$(MeCN)$_2$ (4 mg, 0.015 mmol, 0.15 equiv.) in degassed DMF (1 mL, 0.1 M) is stirred at 25° C. for 33 h, according to the procedure described for the synthesis of macrolactone 18d, to yield, after preparative thin layer chromatography (250 mm silica gel plates, 80% EtOAc in hexanes), starting vinyl iodide 24 (21 mg, 39%) and macrolactone 45 (30 mg, 56%). R$_f$=0.48 (silica gel, 80% EtOAc in hexanes); [α]$^{22}{}_D$ −48.3 (c 0.2, CHCl$_3$); IR (thin fiim) ν$_{max}$ 3372, 2924, 2860, 1731, 1682, 1454, 1384, 1252, 1148, 1040, 979, 735 cm$^{-1}$; $^1$H NMR (600 MHz, CHCl$_3$) δ7.21 (s, 1 H, ArH), 6.61 (s, 1 H, C=CCH$_3$), 5.58 (d, J=47.0 Hz, 2 H, CH$_2$F), 5.45 (dd, J=9.8, 5.3 Hz, 1 H, C=CHCH$_2$), 5.26 (dd, J=9.4, 2.0 Hz, 1 H, CHOCO), 4.23 (dd, J=10.9, 2.4 Hz, 1 H, CHOH), 4.08 (d, J=13.1 Hz, 1 H, CH$_2$OH), 4.01 (d, J=13.1 Hz, 1 H, CH$_2$OH), 3.70 (dd, J=4.2, 2.7 Hz, 1 H, CHOH), 3.16 (qd, J=6.8, 2.6 Hz, 1 H, CH$_3$CH(C=O)), 2.94 (bs, 1 H, OH), 2.69 (ddd, J=15.2, 9.6, 9.6 Hz, 1 H, C=CHCH$_2$CHO), 2.46 (dd, J=14.8, 10.9 Hz, 1 H, CH$_2$COO), 2.36–2.24 (m, 2 H, CH$_2$C(CH$_2$OH)=CH), 2.30 (dd, J=14.8, 2.6 Hz, 1 H, CH$_2$COO), 2.09 (s, 3 H, CH=C(CH$_3$)), 2.07 (m, 1 H, C=CHCH$_2$CHO), 1.77–1.58 (m, 5 H), 1.33 (s, 3 H, C(CH$_3$)$_2$), 1.17 (d, J=6.9 Hz, 3 H, CH(CH$_3$)), 1.06 (s, 3 H, C(CH$_3$)$_2$), 1.00 (d, J=7.0 Hz, 3 H, CH(CH$_3$)); HRMS (FAB), calcd. for C$_{22}$H$_{40}$FNO$_6$S (M+Cs$^+$), 658.1615 found 658.1644.

Macrolactone 46 as illustrated in Scheme 9. A solution of vinyl iodide 24 (32 mg, 0.060 mmol, 1.0 equiv.), stannane 8p (28 mg, 0.101 mmol, 1.7 equiv.) and PdCl$_2$(MeCN)$_2$ (1.7 mg, 0.07 mmol, 0.1 equiv.) in degassed DMF (650 μL, 0.1 M) is stirred at 25° C. for 20 h, according to the procedure described for the synthesis of macrolactone 18d, to yield, after preparative thin layer chromatography (250 mm silica gel plates, 80% EtOAc in hexanes), starting vinyl iodide 24 (6 mg, 19%) and macrolactone 46 (17 mg, 54%). R$_f$=0.37 (silica gel, 80% EtOAc in hexanes); [α]$^{22}{}_D$ −48.7 (c 0.15, CHCl$_3$); IR (thin film) ν$_{max}$ 3402, 2931, 2874, 1731, 1686, 1533, 1458, 1420, 1383, 1242, 1150, 1048, 1007, 979 cm$^{-1}$; $^1$H NMR (500 MHz, CDCl$_3$) δ6.50 (s, 1 H, ArH), 6.36 (s, 1 H, CH+CCH$_3$), 5.45 (dd, J=10.0, 5.0 Hz, 1 H, C=CHCH$_2$), 5.23 (dd, J=9.5, 1.5 Hz, 1 H, CHOCO), 4.24 (bd, J=11.0 Hz, 1 H, CHOH), 4.11–3.68 (m, 1 H, CH$_2$OH), 4.07 (s, 3 H, OCH$_3$), 4.01 (d, J=13.0 Hz, 1 H, CH$_2$OH), 3.71 (dd, J=4.0, 2.5 Hz, 1 H, CHOH), 3.30 (bs, 1 H, OH), 3.16 (qd, J=7.0, 2.5 Hz, 1 H, CH$_3$CH(C=O)), 3.00 (bs, 1 H, OH), 2.68 (ddd, J=15.0, 10.0, 9.5 Hz, 1 H, C=CHCH$_2$CHO), 2.46 (dd, J=15.0, 11.0 Hz, 1 H, CH$_2$COO), 2.30–2.20 (m, 2 H, CH$_2$C(CH$_2$OH)=CH), 2.29 (dd, J=15.0, 3.0 Hz, 1 H, CH$_2$COO), 2.11–2.04 (m, 1 H, C=CHCH$_2$CHO), 2.11 (s, 3 H, CH=C(CH$_3$)), 1.83–1.61 (m, 4 H), 1.41–1.25 (m, 1 H), 1.33 (s, 3 H, C(CH$_3$)$_2$), 1.18 (d, J=7.0 Hz, 3 H, CH(CH$_3$)), 1.07 (s, 3 H, C(CH$_3$)$_2$), 1.01 (d, J=7.0 Hz, 3 H, CH(CH$_3$)); HRMS (FAB), calcd. for C$_{27}$H$_{41}$NO$_7$S (M+Cs$^+$), 656.1658 found 656.1675.

Macrolactone 47 as illustrated in Scheme 9. A solution of vinyl iodide 24 (41 mg, 0.076 mmol, 1.0 equiv.), stannane 8r (61 mg, 0.151 mmol, 2.0 equiv.) and PdCl$_2$(MeCN)$_2$ (4 mg, 0.015 mmol, 0.2 equiv.) in degassed DMF (760 μL, 0.1 M) is stirred at 25° C. for 21 h, according to the procedure described for the synthesis of macrolactone 18d, to yield, after preparative thin layer chromatography (250 mm silica gel plates, 80% EtOAc in hexanes), starting vinyl iodide 24 (6 mg, 15%) and macrolactone 47 (20.5 mg, 51%). R$_f$=0.41 (silica gel, 80% hEtOAc in hexanes); [α]$^{22}{}_D$ −86.0 (c 0.25, CHCl$_3$); IR (thin film) ν$_{max}$ 3387, 2968, 2936, 2874, 1733, 1685, 1458, 1381, 1253, 1149, 1050, 1003, 912 cm$^{-1}$; $^1$H NMR (500 MHz, CDCl$_3$) δ6.97 (s, 1 H, ArH), 6.63 (s, 1 H, CHCCH$_3$), 5.43 (dd, J=9.0, 5.5 Hz, 1 H, C=CHCH$_2$), 5.25 (dd, J=8.5, 2.0 Hz, 1 H, CHOCO), 4.32 (ddd, J 11.0, 5.5, 2.5 Hz, 1 H, CHOH), 4.12–4.07 (m, 2 H, CH$_2$OH and OH), 4.02 (d, J=11.0 Hz, 1 H, CH$_2$OH), 3.69 (dd, J=2.0, 2.0 Hz, 1 H, CHOH), 3.16 (qd, J=7.0, 2.5 Hz, 1 H, CH$_3$CH(C=O)), 3.08 (bs, 1 H, OH), 2.98 (q, J=7.0 Hz, 2 H, CH$_2$CH$_3$), 2.61 (ddd, J=15.0, 9.0, 9.0 Hz, 1 H, C=CHCH$_2$CHO), 2.46 (dd, J=14.5, 11.0 Hz, 1 H, CH$_2$COO), 2.38 (dd, J=15.0, 4.0 Hz, 1 H, CH$_2$C(CH$_2$OH)=CH), 2.31–2.25 (m, 1 H, CH$_2$C(CH$_2$OH)=CH), 2.23 (dd, J=14.5, 2.5 Hz, 1 H, CH$_2$COO), 2.17–2.07 (m, 1 H, C=CHCH$_2$CHO), 2.04 (s, 3 H, CH=C(CH$_3$)), 1.97 (bs, 1 H, OH), 1.78–1.61 (m, 3 H), 1.38–1.23 (m, 2 H), 1.37 (q, J=7.0 Hz, 3 H, CH$_2$CH$_3$), 1.35 (s, 3 H, C(CH$_3$)$_2$), 1.18 (d, J=7.0 Hz 3 H, CH(CH$_3$)), 1.05 (s, 3 H, C(CH$_3$)$_2$), 1.01 (d, J=7.0 Hz, 3 H, CH(CH$_3$)); HRMS (FAB), calcd. for C$_{28}$H$_{43}$NO$_6$S (M+Na$^+$), 544.2709 found 544.2724.

Macrolactone 48 as illustrated in Scheme 9. A solution of vinyl iodide 24 (26 mg, 0.048 mmol, 1.0 equiv.), stannane 8h (29 mg, 0.072 mmol, 1.5 equiv.) and PdCl$_2$(MeCN)$_2$ (1.5 mg, 0.006 mmol, 0.1 equiv.) in degassed DMF (480 μL, 0.1 M) is stirred at 25° C. for 15 h, according to the procedure described for the synthesis of macrolactone 18d, to yield, after preparative thin layer chromatography (250 mm silica gel plates, EtOAc), starting vinyl iodide 24 (10.5 mg, 40%) and macrolactone 48 (10.5 mg, 41%). R$_f$=0.27 (silica gel, EtOAc); [α]$^{22}$$_D$ 31 43.0 (c 0.14, CHCl$_3$); IR (thin film) ν$_{max}$ 3388, 2924, 2851, 1732, 1682, 1462, 1384, 1251, 1185, 1150, 1067 cm$^{-1}$; $^1$H NMR (500 MHz, CDCl$_3$) δ7.13 (s, 1 H, ArH), 6.63 (s, 1 H, CH=CCH$_3$), 5.45 (dd, J=9.0, 6.0 Hz, 1 H, C=CHCH$_2$), 5.27 (bd, J=7.0 Hz, 1 H, CHOCO), 4.29 (dd, J=11.0, 2.5 Hz, 1 H, CHOH), 4.09 (d, J=13.0 Hz, 1 H, CH$_2$OH), 4.00 (d, J=13.0 Hz, 1 H, CH$_2$OH), 3.68 (dd, J=4.0, 2.5 Hz, 1 H, CHOH), 3.15 (qd, J=6.5, 2.5 Hz, 1 H, CH$_3$CH(C=O)), 2.99 (bs, 1 H, OH), 2.65 (ddd, J=15.0, 9.0, 9.0 Hz, 1 H, C=CHCH$_2$CHO), 2.46 (dd, J=14.5, 11.0 Hz, 1 H, CH$_2$COO), 2.39–2.33 (m, 1 H, CH$_2$C(CH$_2$OH)=CH), 2.26 (dd, J=14.5, 2.5 Hz, 1 H, CH$_2$COO), 2.26–2.20 (m, 1 H, CH$_2$C(CH$_2$OH)=CH), 2.14–2.10 (m, 1 H, C=CHCH$_2$CHO), 2.07 (s, 3 H, CH=C(CH$_3$)), 1.99–1.61 (m, 4 H), 1.42–1.24 (m, 2 H), 1.33 (s, 3 H, C(CH$_3$)$_2$), 1.16 (d, J=7.0 Hz, 3 H, CH(CH$_3$)), 1.04 (s, 3 H, C(CH$_3$)$_2$), 1.00 (d, J=7.0 Hz, 3 H, CH(CH$_3$)); HRMS (FAB), calcd. for C$_{27}$H$_{41}$NO$_7$S (M+Cs$^+$), 656.1658 found 656.1677.

Macrolactone 49 as illustrated in Scheme 9. A solution of vinyl iodide 24 (37 mg, 0.069 mmol, 1.0 equiv.), stannane 8q (47 mg, 0.117 mmol, 1.7 equiv.) and Pd(PPh$_3$)$_4$ (10 mg, 0.009 mmol, 0.13 equiv.) in degassed toluene (780 μL, 0.1 M) is heated at 100° C. for 2 h according to the procedure described for the synthesis of macrolactone 18h, to yield, after preparative thin layer chromatography (250 mm silica gel plates, 80% EtOAc in hexanes), macrolactone 49 (5.5 mg, 15%). R$_f$=0.35 (silica gel, 80% EtOAc in hexanes); [α]$^{22}$$_D$ –48.1 (c 0.27, CHCl$_3$); IR (thin film) ν$_{max}$ 3403, 2930, 2873, 1732, 1686, 1462, 1381, 1291, 1266, 1250, 1149, 1004, 980, 937 cm$^{-1}$; $^1$H NMR (500 MHz, CDCl$_3$) δ7.04 (s, 1 H, ArH), 6.85 (dd, J=17.5, 11.0 Hz, 1 H, CH=CH$_2$), 6.61 (s, 1 H, CH=CCH$_3$), 6.05 (d, J=17.5 Hz, 1 H, CH=CH$_2$), 5.56 (d, J=11.0 Hz, 1 H, CH=CH$_2$), 5.45 (dd, J=10.0, 5.5 Hz, 1 H, C=CHCH$_2$), 5.26 (dd, J=9.5, 2.0 Hz, 1 H, CHOCO), 4.29 (ddd, J=11.0, 6.0, 2.5 Hz, 1 H, CHOH), 4.09 (dd, J=13.0, 6.5 Hz, 1 H, CH$_2$OH), 4.02 (dd, J=13.0, 6.0 Hz, 1 H, CH$_2$OH), 3.71 (ddd, J=4.5, 2.5, 2.5 Hz, 1 H, CHOH), 3.54 (d, J=6.0 Hz, 1 H, OH), 3.17 (qd, J=7.5, 2.0 Hz, 1 H, CH$_3$CH(C=O)), 3.02 (d, J=2.0 Hz, 1 H, OH), 2.68 (ddd, J=15.0, 10.0, 9.0 Hz, 1 H, C=CHCH$_2$CHO), 2.45 (dd, J=14.5, 11.0 Hz, 1 H, 3 H, CH$_2$COO), 2.37–2.31 (m, 1 H, CH$_2$C(CH$_2$OH)=CH), 2.30–2.24 (m, 1 H, CH$_2$C(CH$_2$OH)=CH), 2.28 (dd, J=15.0, 3.5 Hz, 1 H, CH$_2$COO), 2.14–2.07 (m, 1 H, C=CHCH$_2$CHO), 2.09 (d, J=1.0 Hz, 1 H, CH=C(CH$_3$)), 1.79–1.60 (m, 4 H), 1.39–1.25 (m, 2 H), 1.35 (s, 3 H, C(CH$_3$)$_2$), 1.18 (d, J=7.0 Hz, 3 H, CH(CH$_3$)), 1.07 (s, 3 H, C(CH$_3$)$_2$), 1.02 (d, J=7.0 Hz, 3 H, CH(CH$_3$)); HRMS (FAB), calcd. for C$_{28}$H$_{41}$NO$_6$S (M+Cs$^+$), 652.1709 found 652.1693.

Fluoride 50 as illustrated in Scheme 9: A solution of triol 45 (3.6 mg, 0.007 mmol, 1.0 equiv.) in CH$_2$Cl$_2$ (0.1 mL, 0.07 M) at –78° C. is treated with DAST (11 μL of a 0.7 M solution in CH$_2$Cl$_2$, 0.008 mmol, 1.1 equiv.) and the mixture is stirred at –78° C. for 10 min. The reaction is then quenched by the addition of saturated aqueous NaHCO$_3$ (500 μL) and the mixture is allowed to warm to 25° C. The product is then partitioned between saturated aqueous NaHCO$_3$ (5 mL) and CH$_2$Cl$_2$ (5 mL) and the layers are separated. The aqueous phase is extracted with CH$_2$Cl$_2$ (2×5 mL) and the combined organic extracts are dried (MgSO$_4$) and then concentrated under reduced pressure. Preparative thin layer chromatography (250 mm silica gel plate, 40% EtOAc in hexanes) furnishes fluoride 50 (2.1 mg, 58%). R$_f$=0.39 (silica gel, 50% EtOAc in hexanes); [α]$^{22}$$_D$ –34.4 (c 0.09, CHCl$_3$); IR (thin film) ν$_{max}$ 3413, 2919, 2849, 1725, 1684, 1465, 1381, 1290, 1250, 1150, 1041, 979, 872 cm$^{-1}$; $^1$H NMR (600 MHz, CDCl$_3$) δ7.22 (s, 1 H, ArH), 6.62 (s, 1 H, CH=CCH$_3$), 5.60 (d, J=47.0 Hz, 2 H, ArCH$_2$F), 5.56–5.52 (m, 1 H, C=CHCH$_2$), 5.27 (dd, J=9.5, 2.0 Hz, 1 H, CHOCO), 4.79 (dd, J=82.2, 10.8 Hz, 1 H, CH=CCH$_2$F), 4.71 (dd, J=81.8, 10.8 Hz, 1 H, CH=CCH$_2$F), 4.24 (dd, J=10.9, 2.6 Hz, 1 H, CHOH), 3.70 (dd, J=4.3, 2.5 Hz, 1 H, CHOH), 3.15 (qd, J=6.8, 2.5 Hz, 1 H, CH$_3$CH(C=O)), 3.00–2.85 (m, 1 H, OH), 2.71 (m, 1 H, C=CHCH$_2$CHO), 2.46 (dd, J=14.9, 11.0 Hz, 1 H, CH$_2$COO), 2.38–2.29 (m, 2 H, CH$_2$C(CH$_2$OH)=CH), 2.30 (dd, J=14.9, 2.8 Hz, 1 H, CH$_2$COO), 2.15–2.09 (m, 1 H, C=CHCH$_2$CHO), 2.11 (d, J=1.0 Hz, CH=C(CH$_3$)), 1.80–1.50 (m, 4 H), 1.37–1.29 (m, 2 H), 1.33 (s, 3 H, C(CH$_3$)$_2$), 1.18 d, J=6.8 Hz, 3 H CH(CH$_3$)), 1.06 (s, 3 H, C(CH$_3$)$_2$), 1.01 (d, J=7.1 Hz, 3 H, CH(CH$_3$)); HRMS (FAB calcd. for C$_{27}$H$_{39}$F$_2$NO$_5$S (M+H$^+$), 528.2595 found 528.2610.

Fluoride 51 as illustrated in Scheme 9. A solution of triol 46 (8.2 mg, 0.016 mmol, 1.0 equiv.) in CH$_2$Cl$_2$ (200 μL, 0.08 M) at –78° C. is treated with DAST (0.025 mL, 0.019 mmol, 1.2 equiv.) and the resulting mixture is stirred at –78° C. for 10 min according to the procedure described for the synthesis of fluoride 50, to yield, after preparative thin layer chromatography (250 mm silica gel plates, 30% EtOAc in hexanes), fluoride 51 (3.5 mg, 43%). R$_f$=0.57 (silica gel, 60% EtOAc in hexanes); [α]$^{22}$$_D$ –4.7 (c 0.11, CHCl$_3$); IR (thin film) ν$_{max}$ 3418, 2925, 2852, 1734, 1686, 1535, 1461, 1415, 1383, 1334, 1241, 1150, 1045, 976 cm$^{-1}$; $^1$H NMR (400 MHz, CHCl$_3$) δ6.51 (s, 1 H, ArH), 6.37 (s, 1 H, CH=CCH$_3$), 5.55–5.51 (m, 1 H, C=CHCH$_2$), 5.22 (dd, J=10.0, 2.0 Hz, 1 H, CHOCO), 4.81 (dd, J=74.0, 11.0 Hz, 1 H, CH=CCH$_2$F), 4.71 (dd, J=73.0, 11.0 Hz, 1 H, CH=CCH$_2$F), 4.26 (dd, J=11.0, 2.5 Hz, 1 H, CHOH), 4.09 (s, 3 H, CH$_3$O), 3.71 (dd, J=4.5, 2.0 Hz, 1 H, CHOH), 3.17 (qd, J=7.0, 2.5 Hz, 1 H, CH$_3$CH(C=O)), 3.01–2.95 (m, 1 H, OH), 2.76–2.68 (m, 1 H, C=CHCH$_2$CHO), 2.47 (dd, J=14.5, 11.0 Hz, 1 H, CH$_2$COO), 2.37–2.27 (m, 2 H, CH$_2$C(CH$_2$OH)=CH), 2.29 (dd, J=14.5, 2.5 Hz, 1 H, CH$_2$COO), 2.17–2.11 (m, 1 H, C=CHCH$_2$CHO), 2.14 (s, 3 H, CH=C(CH$_3$)), 1.80–1.50 (m, 4 H), 1.40–1.22 (m, 2 H), 1.34 (s, 3 H, C(CH$_3$)$_2$), 1.19 (d, J=7.0 Hz, 3 H, CH(CH$_3$)), 1.08 (s, 3 H, C(CH$_3$)$_2$), 1.03 (d, J=7.0 Hz, 3 H, CH(CH$_3$));

HRMS (FAB), calcd. for $C_{27}H_{40}FNO_6S$ (M+H⁺), 526.2639 found 526.2625.

Fluoride 52 as illustrated in Scheme 9. A solution of triol 47 (12.5 mg, 0.024 mmol, 1.0 equiv.) in $CH_2Cl_2$ (500 µL, 0.05 M) at −78° C. is treated with DAST (250 RL, 0.1 M in $CH_2Cl_2$, 0.025 mmol, 1.05 equiv.) and the resulting mixture is stirred at −78° C. for 10 min according to the procedure described for the synthesis of fluoride 50, to yield, after preparative thin layer chromatography (250 mm silica gel plates, 60% EtOAc in hexanes), fluoride 52 (5.1 mg, 41%). $R_f$=0.19 (silica gel, 50% EtOAc in hexanes); $[\alpha]^{22}_D$ −68.6 (c 0.22, $CHCl_3$); IR (thin film) $\nu_{max}$ 3504, 2969, 2935, 2877, 1736, 1687, 1461, 1369, 1290, 1250, 1148, 1068, 1044, 1008, 976 cm⁻¹; ¹H NMR (500 MHz, $CDCl_3$) δ6.98 (s, 1 H, ArH), 6.60 (s, 1 H, CH=$CCH_3$), 5.56–5.52 (m, 1 H, C=$CHCH_2$), 5.23 (dd, J=10.0, 2.0 Hz, 1 H, CHOCO), 4.80 (dd, J=73.0, 10.5 Hz, 1 H, CH=$CCH_2F$), 4.71 (dd, J=72.5, 10.5 Hz, 1 H, CH=$CCH_2F$), 4.33 (ddd, J=11.0, 5.5, 2.5 Hz, 1 H, CHOH), 3.71 (ddd, J=5.0, 2.5, 2.0 Hz, 1 H, CHOH), 3.71 (d, J=6.0 Hz, 1 H, CHOH), 3.17 (qd, J=7.0, 2.0 Hz, 1 H, $CH_3CH$(C=O)), 3.07 (m, 1 H, OH), 4.51 (q, J=7.5 Hz, 2 H, $CH_2CH_3$), 2.70 (ddd, J=15.0, 10.0, 2.0 Hz, 1 H, C=$CHCH_2CHO$), 2.45 (dd, J=14.5, 11.0 Hz, 1 H, $CH_2COO$), 2.39–2.28 (m, 2 H, $CH_2C(CH_2OH)$=CH), 2.26 (dd, J=14.5, 2.5 Hz, 1 H, $CH_2COO$), 2.17–2.10 (m, 1 H, C=$CHCH_2CHO$), 2.08 (d, J=1.5 Hz, 3 H, CH=$C(CH_3)$), 1.80–1.67 (m, 3 H), 1.39 (t, J=7.5 Hz, 3 H, $CH_2CH_3$), 1.39–1.24 (m, 2 H), 1.35 (s, 3 H, $C(CH_3)_2$), 1.19 (d, J=7.0 Hz, 3 H, $CH(CH_3)$), 1.07 (s, 3 H, $C(CH_3)_2$), 1.03 (d, J=7.0 Hz, 3 H, $CH(CH_3)$); HRMS (FAB), calcd. for $C_{28}H_{42}FNO_5S$ (M+Cs⁺), 656.1822 found 656.1843.

Fluoride 53 as illustrated in Scheme 9. A solution of triol 49 (6.0 mg, 0.0151 mmol, 1.0 equiv.) in $CH_2Cl_2$ (1.5 mL, 0.01 M) at −78° C. is treated with DAST (0.20 mL, 0.08 M in $CH_2Cl_2$, 0.016 mmol, 1.1 equiv.) and the resulting mixture is stirred at −78° C. for 10 min according to the procedure described for the synthesis of fluoride 50, to yield, after preparative thin layer chromatography (250 mm silica gel plates, 50% EtOAc in hexanes), fluoride 53 (3.0 mg, 50%). $R_f$=0.50 (silica gel, 50% EtOAc in hexanes); $[\alpha]^{22}_D$ −12.4 (c 0.2, $CHCl_3$); IR (thin film) $\nu_{max}$ 3408, 2926, 2851, 1732, 1682, 1462, 1384, 1292, 1250, 1150, 1068, 974 cm⁻; ¹H NMR (600 MHz, $CDCl_3$) δ7.04 (s, 1 H, ArH), 6.86 (dd, J=17.4, 10.8 Hz, 1 H, CH=$CH_2$), 6.59 (s, 1 H, CH=$CCH_3$), 6.05 (d, J=17.5 Hz, 1 H, CH=$CH_2$), 5.55 (d, J=11.0 Hz, 1 H, CH=$CH_2$) 5.57–5.51 (m, 1 H, C=$CHCH_2$), 5.25 (d, J=10.0 Hz, 1 H, CHOCO), 4.79 (dd, J 83.8, 10.7 Hz, 1 H, CH=$CCH_2F$), 4.71 (dd, J=83.6, 10.7 Hz, 1 H, CH=$CCH_2F$), 4.28 (dd, J=10.6, 1.6 Hz, 1 H, CHOH), 3.70 (m, 1 H, CHOH), 3.33–3.25 (m, 1 H, CHOH), 3.16 (qd, J=7.0, 2.1 Hz, 1 H, $CH_3CH$(C=O)), 2.98 (m, 1 H, OH), 2.75–2.66 (m, 1 H, C=$CHCH_2CHO$), 2.46 (dd, J=14.6, 11.0 Hz, 1 H, $CH_2COO$), 2.37–2.27 (m, 2 H, $CH_2C(CH_2OH)$=CH), 2.28 (dd, J=14.6, 2.6 Hz, 1 H, $CH_2COO$), 2.15–2.08 (m, 1 H, C=$CHCH_2CHO$), 2.11 (s, 3 H, CH=$C(CH_3)$), 1.80–1.64 (m, 3 H), 1.43–1.27 (m, 2 H), 1.34 (s, 3 H, $C(CH_3)_2$), 1.18 (d, J=6.8 Hz, 3 H, $CH(CH_3)$), 1.07 (s, 3 H, $C(CH_3)_2$), 1.03 (d, J=7.0 Hz, 3 H, $CH(CH_3)$); HRMS (FAB), calcd. for $C_{28}H_{40}FNO_5S$ (M+H⁺), 522.2689 found 522.2704.

Epoxide 54 as illustrated in Scheme 9. To a solution of allylic alcohol 45 (25.4 mg, 0.049 mmol, 1.0 equiv.) and 4 Å molecular sieves in $CH_2Cl_2$ (0.50 mL) at −40° C. is added dropwise (+)-diethyl-D-tartrate (41 µL, 0.59 M in $CH_2Cl_2$, 0.024 mmol, 0.5 equiv.) followed by titanium isopropoxide (55 µL, 0.35 M in $CH_2Cl_2$, 0.019 mmol, 0.4 equiv.). After 1 h at that temperature, t-butyl hydroperoxide (22 gL of a 5 M solution in decane, 0.110 mmol, 2.2 equiv.) is added and the reaction mixture is stirred at −30° C. for 2 h. The reaction mixture is then filtered through celite into saturated aqueous $Na_2SO_4$ (10 mL), eluting with EtOAc (10 mL). The resulting biphasic mixture is then stirred for 1 h and the layers are separated. The aqueous phase is extracted with EtOAc (3×10 mL) and the combined organic extracts are dried ($MgSO_4$) and concentrated under reduced pressure. Preparative thin layer chromatography (250 mm silica gel plates, 80% EtOAc in hexanes) furnishes epoxide 54 (13.5 mg, 52%). $R_f$=0.23 (silica gel, 80% EtOAc in hexanes); $[\alpha]^{22}_D$ −55.4 (c 0.06, $CHCl_3$); IR (thin film) $\nu_{max}$ 3425, 2929, 2862, 1732, 1688, 1456, 1367, 1292, 1258, 1195, 1149, 1040, 980 cm⁻¹; ¹H NMR (600 MHz, $CHCl_3$) δ7.22 (s, 1 H, ArH), 6.62 (s, 1 H, CH=$CCH_3$), 5.59 (d, J=47.0 Hz, 2 H, $ArCH_2F$), 5.46 (dd, J=6.7, 3.4 Hz, 1 H, CHOCO), 4.14–4.09 (m, 1 H, CHOH), 3.89 (d, J=6.4 Hz, 1 H, OH), 3.76 (bs, 1 H, CHOH), 3.72 (d, J=12.1 Hz, 1 H, $CH_2OH$), 3.56 (dd, J=12.1, 7.5 Hz, 1 H, $CH_2OH$), 3.33 (qd, J=6.8, 5.3 Hz, 1 H, $CH_3CH$(C=O)), 3.16 (dd, J=6.3, 6.1 Hz, 1 H, C(O)$CHCH_2CHO$), 2.55 (dd, J=14.1, 10.2 Hz, 1 H, $CH_2COO$), 2.50 (bs, 1 H, OH), 2.41 (dd, J=14.1, 3.1 Hz, 1 H, $CH_2COO$), 2.11 (s, 3 H, CH=C($CH_3$)), 2.10–1.97 (m, 2 H, C(O)$CHCH_2CHO$), 1.91–1.81 (m, 2 H, $CH_2C(CH_2OH)$), 1.74–1.60 (m, 3 H), 1.50–1.30 (m, 2 H), 1.34 (s, 3 H, $C(CH_3)_2$), 1.18 (d, J=6.8 Hz, 3 H, $CH(CH_3)$), 1.06 (s, 3 H, $C(CH_3)_2$), 0.99 (d, J=7.0 Hz, 3 H, $C(CH_3)_2$); HRMS (FAB), calcd. for $C_{27}H_{40}FNO_7S$ (M+H⁺), 542.2588 found 542.2575.

Epoxide 55 as illustrated in Scheme 9. To a solution of allylic alcohol 46 (22 mg, 0.042 mmol, 1.0 equiv.) and 4 Å molecular sieves in $CH_2Cl_2$ (420 µL) at −40° C. is added dropwise (+)-diethyl-D-tartrate (4 µL, 0.021 mmol, 0.5 equiv.), followed by titanium isopropoxide (5 µL, 0.016 mmol, 0.4 equiv.) and after 1 h at this temperature, t-butyl hydroperoxide (18 µL of a 5 M solution in decane, 0.092 mmol, 2.2 equiv.) according to the procedure described for the synthesis of epoxide 54 to yield, after preparative thin layer chromatography (250 mm silica gel plates, 80% EtOAc in hexanes), epoxide 55 (16 mg, 70%). $R_f$=0.25 (silica gel, 80% EtOAc in hexanes); $[\alpha]^{22}_D$ −44.8 (c 1.4, $CHCl_3$); IR (thin film) $\nu_{max}$ 3435, 2959, 2935, 2877, 1732, 1689, 1534, 1459, 1421, 1371, 1338, 1241, 1174, 1039, 980 cm⁻; ¹H NMR (500 MHz, $CDCl_3$) δ6.51 (s, 1 H, ArH), 6.35 (s, 1 H, CH=$CCH_3$), 5.40 (dd, J=7.0, 3.0 Hz, 1 H, CHOCO), 4.11 (ddd, J=10.0, 6.5, 3.0 Hz, 1 H, CHOH), 4.07 (s, 3 H, $CH_3O$), 3.88 (d, J=6.0 Hz, 1 H, OH), 3.77–3.74 (m, 1 H, CHOH), 3.73 (dd, J=12.5, 4.0 Hz, 1 H, $CH_2OH$), 3.57 (dd, J=12.5, 8.0 Hz, 1 H, $CH_2OH$), 3.32 (qd, J=7.0, 5.0 Hz, 1 H, $CH_3CH$(C=O)), 3.16 (dd, J=7.0, 5.5 Hz, 1 H, C(O)$CHCH_2CHO$), 2.54 (dd, J=14.5, 10.0 Hz, 1 H, $CH_2COO$), 2.50 (bs, 1 H, OH), 2.40 (dd, J=14.5, 3.5 Hz, 1 H, $CH_2COO$), 2.13 (s, 3 H, CH=$C(CH_3)$), 2.12–2.05 (m, 1 H, C(O)$CHCH_2CHO$), 2.03–1.95 (m, 2 H), 1.90–1.82 (m, 1 H, $CH_2C(CH_2OH)$), 1.75–1.60 (m, 2 H), 1.50–1.20 (m, 3 H), 1.35 (s, 3 H, $C(CH_3)_2$), 1.16 (d, J=7.0 Hz, 3 H, $CH(CH_3)$), 1.07 (s, 3 H, $C(CH_3)_2$), 0.99 (d, J=7.0 Hz, 3 H); HRMS (FAB), calcd. for $C_{27}H_{41}NO_8S$ (M+Cs⁺), 672.1607 found 672.1584.

Fluoride 58 as illustrated in Scheme 9. A solution of triol 54 (5.0 mg, 0.009 mmol, 1.0 equiv.) in $CH_2Cl_2$ (1 mL, 0.01 M) at −78° C. is treated with DAST (0.25 mL of a 0.1 M solution in $CH_2Cl_2$, 0.025 mmol, 1.05 equiv.) according to the procedure described for the synthesis of fluoride 50, to yield, after preparative thin layer chromatography (250 mm silica gel plates, 60% EtOAc in hexanes), fluoride 58 (2.0 mg, 41%). $R_f$=0.22 (silica gel, 50% EtOAc in hexanes); IR (thin film) $\nu_{max}$ 3402, 2954, 2923, 2853, 1732, 1688, 1462, 1378, 1262, 1185, 1149, 1082, 1031, 980 cm$^{-1}$; $^1$H NMR (500 MHz, CHCl$_3$) δ7.23 (s, 1 H, ArH), 6.63 (s, 1 H, CH=CCH$_3$), 5.60 (d, J=47 Hz, 2 H, ArCH$_2$F), 5.47 (dd, J=7.0, 3.0 Hz, 1 H, CHOCO), 4.39 (dd, J=97.0, 10.5 Hz, 1 H, C(O)CH$_2$F), 4.30 (dd, J=97.0, 10.5 Hz, 1 H, C(O)CH$_2$F), 4.13 (ddd, J=9.5, 6.5, 3.0 Hz, 1 H, CHOH), 3.75 (dd, J=5.0, 5.0 Hz, 1 H, CHOH), 3.74 (d, J=7.0 Hz, 1 H, OH), 3.31 (qd, J=7.0, 6.0 Hz, 1 H, CH$_3$CH(C=O)), 3.02 (dd, J=6.0, 6.0 Hz, 1 H, CH(O)CH$_2$CHO), 2.56 (dd, J=14.0, 10.0 Hz, 1 H, CH$_2$COO), 2.46 (brs, 1 H, OH), 2.42 (dd, J=14.0, 4.0 Hz, 1 H, CH$_2$COO), 2.13 (s, 3 H, CH=C(CH$_3$)), 2.10–1.97 (m, 3 H), 1.95–1.87 (m, 1 H), 1.90–1.82 (m, 1 H), 1.75–1.63 (m, 2 H), 1.50–1.20 (m, 2 H), 1.36 (s, 3 H, C(CH$_3$)$_2$), 1.16 (d, J=7.0 Hz, 3 H, CH(CH$_3$)), 1.08 (s, 3 H, C(CH$_3$)$_2$), 1.01 (d, J=7.0 Hz, 3 H, C(CH$_3$)$_2$); MS (electrospray), calcd. for C$_{27}$H$_{39}$F$_2$NO$_6$S (M+H$^+$) 544, found 544.

Fluoride 59 as illustrated in Scheme 9. A solution of triol 55 (15 mg, 0.028 mmol, 1.0 equiv.) in CH$_2$Cl$_2$ (280 μL, 0.1 M) at −78° C. is treated with DAST (5 μL, 0.038 mmol, 1.4 equiv.) according to the procedure described for the synthesis of fluoride 50, to yield, after preparative thin layer chromatography (250 mm silica gel plates, 50% EtOAc in hexanes), fluoride 59 (4.0 mg, 26%). R$_f$=0.42 (silica gel, 80% EtOAc in hexanes); [α]$^{22}_D$ −29.4 (c 0.33, CHCl$_3$); IR (thin film) ν$_{max}$ 3492, 2960, 2928, 2874, 2865, 1738, 1732, 1693, 1682, 1537, 1462, 1455, 1422, 1384, 1241, 1144, 980 cm$^{-1}$; $^1$H NMR (500 MHz, CHCl$_3$) δ6.52 (s, 1 H, ArH), 6.35 (s, 1 H, CH=CCH$_3$), 5.41 (dd, J=7.0, 3.5 Hz, 1 H, CHOCO), 4.40 (dd, J=111.5, 10.5 Hz, 1 H, CH$_2$F), 4.30 (dd, J=111.5, 10.5 Hz, 1 H, CH$_2$F), 4.14 (ddd, J=10.0, 7.0, 3.5 Hz, 1 H, CHOH), 4.08 (s, 3 H, CH$_3$O), 3.80 (d, J=7.0 Hz, 1 H, OH), 3.78 (dd, J=3.5, 3.5 Hz, 1 H, CHOH), 3.31 (qd, J=7.0, 5.0 Hz, 1 H, CH$_3$CH(C=O)), 3.01 (dd, J=7.0, 5.5 Hz, 1 H, C(O)CHCH$_2$CHO), 2.55 (dd, J=14.5, 10.0 Hz, 1 H, CH$_2$COO), 2.53 (bs, 1 H, OH), 2.40 (dd, J=14.5, 3.5 Hz, 1 H, CH$_2$COO), 2.14 (s, 3 H, CH=C(CH$_3$)), 2.12–2.15–1.90 (m, 3 H), 1.73–1.70 (m, 1 H), 1.55–1.24 (m, 5 H), 1.36 (s, 3 H, C(CH$_3$)$_2$), 1.17 (d, J=6.5 Hz, 3 H, CH(CH$_3$)), 1.09 (s, 3 H, C(CH$_3$)$_2$), 1.00 (d, J=7.0 Hz, 3 H, C(CH$_3$)$_2$); HRMS (FAB), calcd. for C$_{27}$H$_{40}$FNO$_7$S (M+Cs$^+$), 674.1564 found 674.1594.

Epoxide 57 as shown in Scheme 10. To a solution of allylic alcohol 24 (81 mg, 0.151 mmol, 1.0 equiv.) and 4 Å molecular sieves in CH$_2$Cl$_2$ (1.25 mL) at −40° C. is added dropwise (+)-diethyl-D-tartrate (13 μL, 0.076 mmol, 0.5 equiv.), followed by titanium isopropoxide (18 μL, 0.060 mmol, 0.4 equiv.) and after 1 h at this temperature, t-butyl hydroperoxide (66 μL of a 5 M solution in decane, 0.330 mmol, 2.2 equiv.) and the reaction conducted according to the procedure described for the synthesis of epoxide 54 to yield, after flash column chromatography (silica gel, 80% EtOAc in hexanes), epoxide 57 (74 mg, 89%). R$_f$=0.34 (silica gel, 80% EtOAc in hexanes); [α]$^{22}_D$ −32.5 (c 0.3, CHCl$_3$); IR (thin film) ν$_{max}$ 3455, 2959, 2931, 2877, 1733, 1689, 1465, 1377, 1289, 1257, 1147, 1040, 979, 912 cm$^{-1}$; $^1$H NMR (600 MHz, CHCl$_3$) δ6.46 (s, 1 H, CH=CCH$_3$), 5.48 (dd, J=4.9, 4.7 Hz, 1 H, CHOCO), 4.00 (bm, 1 H, CHOH), 3.75 (dd, J=5.6, 3.4 Hz, 1 H, CHOH), 3.71 (d, J=12.5 Hz, 1 H, CH$_2$OH), 3.64 (bs, 1 H, OH), 3.56 (d, J=12.5 Hz, 1 H, CH$_2$OH), 3.32 (qd, J=6.7, 6.7 Hz, 1 H, CH$_3$CH(C=O)), 3.09 (dd, J=6.3, 6.2 Hz, 1 H, C(O)CHCH$_2$CHO), 2.52 (dd, J=14.3, 9.8 Hz, 1 H, CH$_2$COO), 2.43 (dd, J=14.3, 3.4 Hz, 1 H, CH$_2$COO), 2.28 (bs, 1 H, OH), 1.95 (m, 2 H, C(O)CHCH$_2$CHO), 1.86 (s, 3 H, CH=C(CH$_3$)), 1.79 (m, 1 H, CH$_2$C(CH$_2$OH)), 1.67 (m, 1 H), 1.61 (m, 1 H), 1.46 (m, 2 H), 1.33 (s, 3 H, C(CH$_3$)$_2$), 1.24 (m, 2 H), 1.15 (d, J=6.8 Hz, 3 H, CH(CH$_3$)), 1.06 (s, 3 H, C(CH$_3$)$_2$), 0.98 (d, J=7.0 Hz, 3 H, C(CH$_3$)$_2$); HRMS (FAB), calcd for C$_{23}$H$_{37}$IO$_7$ (M+Na$^+$), 575.1483 found 575.1462.

Epoxide 56 as illustrated in Scheme 9. A solution of vinyl iodide 57 (20 mg, 0.036 mmol, 1.0 equiv.), stannane 8r (29 mg, 0.072 mmol, 1.5 equiv.) and PdCl$_2$(MeCN)$_2$ (2.0 mg, 0.004 mmol, 0.1 equiv.) in degassed DMF (360 μL, 0.1 M) is stirred at 25° C. for 20 h, according to the procedure described for the synthesis of lactone 18d, to yield, after preparative thin layer chromatography (250 mm silica gel plates, EtOAc), starting vinyl iodide 57 (6 mg, 30%) and macrolactone 56 (10 mg, 51%). R$_f$=0.23 (silica gel, 80% EtOAc in hexanes); [α]$^{22}_D$ −60.0 (c 0.14, CHCl$_3$); IR (thin film) ν$_{max}$ 3414, 2969, 2933, 2872, 1736, 1687, 1458, 1373, 1293, 1258, 1150, 980, 914 cm$^{-1}$; $^1$H NMR (500 MHz, CHCl$_3$) δ6.99 (s, 1 H, ArH), 6.61 (s, 1 H, CH=CCH$_3$), 5.43 (dd, J=8.0, 3.0 Hz, 1 H, CHOCO), 4.20 (ddd, J=9.5, 6.5, 3.0 Hz, 1 H, CHOH), 4.04 (d, J=6.5 Hz, 1 H, OH), 3.77 (dd, J=4.0, 4.0 Hz, 1 H, CHOH), 3.74 (dd, J=12.5, 4.0 Hz, 1 H, CH$_2$OH), 3.57 (dd, J=12.5, 8.0 Hz, 1 H, CH$_2$OH), 3.32 (qd, J=7.0, 4.5 Hz, 1 H, CH$_3$CH(C=O)), 3.16 (dd, J=7.5, 5.0 Hz, 1 H, C(O)CHH$_2$CHO), 3.01 (q, J=7.5 Hz, 2 H, CH$_2$CH$_3$), 2.56 (brs, 1 H, OH), 2.54 (dd, J=14.0, 10.0 Hz, 1 H CH$_2$COO), 2.38 (dd, J=14.0, 3.0 Hz, 1 H, CH$_2$COO), 2.14 (ddd, J=15.0, 4.5, 3.0 Hz, 1 H, C(O)CHCH$_2$CHO) 2.11 (s, 3 H, CH=C(CH$_3$)), 2.02–1.96 (m, 1 H, C(O)CHCH$_2$CHO), 1.93–1.84 (m, 1 H), 1.74–1.71 (m, 1 H), 1.55–1.25 (m, 5 H), 1.40 (t, J=8.0 Hz, 3 H, CH$_3$CH$_2$), 1.37 (s, 3 H, C(CH$_3$)$_2$), 1.17 (d, J=7.0 Hz, 3 H, CH(CH$_3$)), 1.08 (s, 3 H, C(CH$_3$)$_2$), 1.01 (d, J=7.0 Hz, 3 H C(CH$_3$)$_2$); HRMS (FAB), calcd. for C28$_6$H$_{43}$NO$_7$S (M+Na$^+$), 560.2658 found 560.2640 bis-Silylether 61 as illustrated in Scheme 10. To a solution of triol 57 (83 mg, 0.150 mmol, 1.0 equiv.) in DMF (1.5 mL, 0.1 M) is added Et$_3$N (315 μL, 2.26 mmol, 15 equiv.) followed by TMSCl (152 μL, 1.20 mmol, 8 equiv.) and the mixture is stirred at 25° C. for 12 h. The mixture is then concentrated under reduced pressure and the resulting oil is partitioned between ether (10 mL) and water (10 mL) and the layers are separated. The aqueous layer is extracted with ether (3×10 mL) and the combined extracts are dried (MgSO$_4$), concentrated under reduced pressure and then filtered through a short plug of silica gel. The resulting filtrate is concentrated, dissolved in CH$_2$Cl$_2$ (5 ml), and silica gel (1 g) is added. The resulting slurry is stirred at 25° C. for 12 h, filtered, concentrated and finally passed through a short plug of silica gel to afford the bis-silylether 61 as a foam (103 mg, 98%). R$_f$=0.48 (silica gel, 60% Et$_2$O in hexanes); [α]$^{22}_D$ −19.1 (c 0.23, CHCl$_3$); IR (thin film) ν$_{max}$ 3408, 2956, 1746, 1698, 1454, 1383, 1250, 1156, 1113, 1060, 1021, 985, 898, 841, 752 cm$^{-1}$; $^1$H NMR (500 MHz, CHCl$_3$) δ6.44 (s, 1 H, ArH), 5.37 (dd, J=9.0 Hz, 1 H, CHOCO), 4.01 (dd, J=10.5, 2.5 Hz, 1 H, CHOH), 3.86 (d, J=10.0 Hz, 1 H, CHOSi), 3.79 (dd, J=12.5, 4.5 Hz, 1 H, CH$_2$OH), 3.49 (ddd, J=12.5, 10.5, 8.5 Hz, 1 H, CH$_2$OH), 3.39 (m, 1 H, OH), 3.09 (dd, J=10.5, 3.5 Hz, 1 H, CH(O)CH$_2$CO), 2.97 (qd, J=6.5, 4.0 Hz, 1 H, CH$_3$CH(C=O)), 2.74 (dd, J=16.5, 10.5 Hz, 1 H, CH$_2$COO), 2.67 (dd, J=16.0, 2.5 Hz, 1 H, CH$_2$COO), 2.18–2.15 (m, 1 H, CH(O) CH$_2$CHO), 1.95–1.82 (m, 2 H), 1.82 (s, 3 H, CH$_3$C=C), 1.68–1.40 (m, 4 H), 1.24 (m, 2 H), 1.18 (s, 3 H, C(CH$_3$)$_2$), 1.11 (s, 3 H, C(CH$_3$)$_2$), 1.06 (d, J=6.5 Hz, 3 H, CH(CH$_3$)), 0.95 (d, J=7.0 Hz, 3 H, CH(CH$_3$)), 0.14 (s, 9 H, (CH$_3$)$_3$Si), 0.06 (s, 9 H, (CH$_3$)$_3$Si); HRMS (FAB), calcd. for C$_{29}$H$_{53}$IO$_7$Si$_2$ (M+Cs$^+$), 829.1429 found 829.1459.

Aldehyde 62 as illustrated in Scheme 10. To a suspension of alcohol 61 (20 mg, 0.029 mmol, 1.0 equiv.) and 4 Å molecular sieves in CH$_2$Cl$_2$ (0.25 mL) is added NMO (10 mg, 0.085 mmol, 3.0 equiv.) followed by TPAP (1 mg, 0.003 mmol, 0.1 equiv.). The resulting slurry is stirred at 25° C. for 40 min and then filtered through a short plug of silica to afford aldehyde 62 (18 mg, 90%). $R_f$=0.66 (silica gel, 60% Et$_2$O in hexanes); IR (thin film) $v_{max}$ 2956, 2913, 2851, 1732, 1698, 1454, 1383, 1250, 1156, 1113, 1021, 987, 895, 841, 750 cm$^{-1}$; $^{-1}$H NMR (600 MHz, CDCl$_3$) δ8.84 (s, 1 H, CH=O), 6.51 (s, 1 H, ArH), 5.46 (dd, J=7.9, 3.4 Hz, 1 H, CHOCO), 3.81 (d, J=8.3 Hz, 1 H, CHOSi), 3.32 (dd, J=8.5, 4.2 Hz, 1 H, CHOSi), 3.04 (qd, J=7.1, 7.1 Hz, 1 H CH$_3$CH (C=O)), 2.65 (dd, J=15.6, 8.3 Hz, 1 H, CH$_2$COO), 2.59 (dd, J=15.6, 4.1 Hz, 1 H, CH$_2$COO), 2.21 (ddd, J=15.2, 3.8, 3.8 Hz, 1 H, CH(O)CH$_2$CHO), 2.06–1.97 (m, 2 H), 1.87 (s, 3 H, CH$_3$C=CH), 1.87–1.80 (m, 1 H), 1.62–1.56 (m, 1 H), 1.51–1.41 (m, 2 H), 1.27–1.21 (obscured m, 2 H), 1.15 (s, 3H, C(CH$_3$)$_2$), 1.08 (s, 3H, C(CH$_3$)$_2$), 1.08 (d, J=6.2 Hz, 3 H, CH(CH$_3$)), 0.96 (d, J=6.9 Hz, 3 H, CH(CH$_3$)), 0.2 (s, 9 H, (CH$_3$)$_3$Si), 0.05 (s, 9 H, (CH$_3$)$_3$Si); HRMS (FAB), calcd. for C$_{29}$H$_{51}$IO$_7$Si$_2$ (M+Cs$^+$), 827.1272 found 827.1304.

Olefin 63 as illustrated in Scheme 10. Methyltriphenylphosphonium bromide (104 mg of a mixture with sodium amide (Aldrich), 0.250 mmol, 9.7 equiv.) in THF (2.0 mL) is added portionwise to a solution of aldehyde 62 (18.0 mg, 0.026 mmol, 1.0 equiv.) in THF (0.5 mL) at −5° C. until the completion of the reaction is established by TLC. Saturated aqueous NH$_4$Cl (1 mL) is added and the product is extracted with ether (3×2 mL) dried (MgSO$_4$) and then concentrated under reduced pressure. Flash column chromatography (silica gel, 15% ether in hexanes) furnishes olefin 63 (11.7 mg, 65%). $R_f$=0.50 (silica gel, 20% Et$_2$O in hexanes); [α]$^{22}_D$ −17.9 (c 0.2, CHCl$_3$); IR (thin film) $v_{max}$ 2954, 2923, 1747, 1698, 1456, 1382, 1250, 1156, 1113, 1021, 986, 889, 841, 750 cm$^{-1}$; $^1$H NMR (500 MHz, CHCl$_3$) δ6.44 (s, 1 H, ArH), 6.00 (dd, J=17.0, 10.0 Hz, 1 H, CH=CH$_2$), 5.36 (dd, J=9.0, 2.0 Hz, 1 H, CHOCO), 5.29 (dd, J=17.5, 1.5 Hz, 1 H, CH$_2$=CH), 5.14 (dd, J=10.5, 1.5 Hz, 1 H, CH$_2$=CH), 4.12 J=9.0, 5.0 Hz, 1 H, CHOSi), 3.85 (d, J=9.5 Hz, 1 H, CHOSi), 3.04 (qd, J=9.0, 7.0 Hz, 1 H, CH$_3$CH(C=O)), 2.85 (dd, J=9.5, 4.0 Hz, 1 H, CH(O) CCH=CH$_2$), 2.73 (dd, J=16.0, 10.0 Hz, 1 H, CH$_2$COO), 2.65 (dd, J=16.0, 2.5 Hz, 1 H, CH$_2$COO), 2.12 (ddd, J=15.0, 4.0, 2.0 Hz, 1 H, CH$_2$CH(O), 1.93–1.78 (3 H, m), 1.84 (s, 3 H, CH=CCH$_3$), 1.65–1.20 (m, 5 H), 1.19 (s, 3 H, C(CH$_3$)$_2$), 1.11 (s, 3 H, C(CH$_3$)$_2$), 1.08 (d, J=6.5 Hz, 3 H, CH(CH$_3$)), 0.95 (d, J=7.0 Hz, 3 H, CH(CH$_3$)), 0.14 (s, 9 H, (CH$_3$)$_3$Si), 0.07 (9 H, s, (CH$_3$)$_3$Si), HRMS (FAB), calcd. for C$_{30}$H$_{53}$IO$_6$Si$_2$ (M+Cs$^+$), 825.1480 found 825.1450.

Macrolactone 65 as illustrated in Scheme 10. A solution of olefin 63 (15 mg, 0.022 mmol, 1.0 equiv.) in EtOH (1.0 mL) is treated with hydrazine (17 μL, 0.500 mmol, 25.0 equiv.) and H$_2$O$_2$ (25 μL, 30% w/w in water, 0.370 mmol, 16.0 equiv.) and the resulting mixture stirred at 0° C. for 3 h. The mixture is then partitioned between ether (4 mL) and water (2 mL) and the layers are separated. The aqueous layer is extracted with ether (3×4 mL) and the combined organic extracts are dried (MgSO$_4$) and concentrated under reduced pressure to give a foam (15.0 mg) which is dissolved in THF (1.5 mL) and treated with HF.pyr. in pyridine/THF (600 mL) and the mixture is stirred at 0° C. for 2 h. The reaction mixture is then quenched with saturated aqueous NaHCO$_3$ (5 mL) and is extracted with EtOAc (3×3 mL). The combined organic extracts are dried (MgSO$_4$) and concentrated under reduced pressure. Flash column chromatography (silica gel, 80% ether in hexanes) furnishes macrolactone 65 (9.4 mg, 75%). $R_f$=0.06 (silica gel, 60% Et$_2$O in hexanes); [α]$^{22}_D$ −19.3 (c 0.33, CHCl$_3$); IR (thin film) $v_{max}$ 3416, 2954, 2926, 2872, 1734, 1689, 1456, 1384, 1287, 1256, 1149, 1084, 978, 892 cm$^{-1}$; $^1$H NMR (500 MHz, CHCl$_3$) δ6.46 (s, 1 H, CH=CCH$_3$), 5.48 (dd, J=5.0, 5.0 Hz, 1 H, CHOCO), 4.03 (brm, 1 H, CHOH), 3.76 (brm, 2 H, CHOH and OH), 3.34 (qd, J=6.5, 6.5 Hz, 1 H, CH$_3$CH(C=O)), 2.73 (dd, J=6.5, 6.5 Hz, 1 H, CH(O)CCH$_2$CH$_3$), 2.54 (dd, J=14.5, 10.0 Hz, 1 H, CH$_2$COO), 2.44 (dd, J=14.5, 8.5 Hz, 1 H, CH$_2$COO), 2.29 (brs, 1 H, OH), 1.96–1.85 (m, 2H), 1.89 (s, 3 H, CH$_3$C=CH), 1.70–1.40 (m, 5 H), 1.31–1.24 (m, 4 H), 1.35 (s, 3 H, C(CH$_3$)$_2$), 1.19 (d, J=6.5 Hz, 3 H, CH(CH$_3$)), 1.07 (s, 3 H, C(CH$_3$)$_2$), 0.99 (d, J=7.0 Hz, 3 H, CH(CH$_3$)), 0.91 (t, J=7.5 Hz, 3 H, CH$_3$CH$_2$); HRMS (FAB), calcd. for C$_{24}$H$_{39}$IO$_6$ (M+Cs$^+$), 683.0846 found 683.0870.

Macrolactone 66 as illustrated in Scheme 10. A solution of vinyl iodide 65 (9.4 mg, 0.017 mmol, 1.0 equiv.), stannane 8j (10 mg, 0.036 mmol, 2.1 equiv.) and PdCl$_2$(MeCN)$_2$ (1.0 mg, 0.004 mmol, 0.2 equiv.) in degassed DMF (250 μL, 0.07 M) is stirred at 25° C. for 15 h, according to the procedure described for the synthesis of macrolactone 18d, to yield, after preparative thin layer chromatography (250 mm silica gel plates, EtOAc) macrolactone 66 (4.6 mg, 52%). $R_f$=0.40 (silica gel, 80% EtOAc in hexanes); [α]$^{22}_D$ −30.0 (c 0.17, CHCl$_3$); IR (thin film) $v_{max}$ 3432, 2967, 2933, 2872, 1736, 1689, 1458, 1384, 1256, 1151, 1067, 1038, 979, 905, 733 cm$^{-1}$; $^1$H NMR (500 MHz, CDCl$_3$) δ7.23 (s, 1 H, ArH), 6.62 (s, 1 H, CH=CCH$_3$), 5.59 (d, J=47.1 Hz, 2 H, CH$_2$F), 5.46 (dd, J=6.3, 3.7 Hz, 1 H, CHOCO), 4.15 (d, J=8.8 Hz, 1 H, CHOH), 3.98 (brs, 1 H, OH), 3.77 (brs, 1 H, CHOH), 3.35 (qd, J=6.6, 4.8 Hz, 1 H, CH$_3$CH(C=O)), 2.82 (dd, J=6.1, 6.1 Hz, 1 H, CH(O)CCH$_2$CH$_3$), 2.56 (dd, J=14.0, 9.9 Hz, 1 H, CH$_2$COO), 2.48 (brs, 1 H, OH), 2.41 (dd, J=14.0, 3.0 Hz, 1 H, CH$_2$COO), 2.13 (s, 3 H, CH=C(CH$_3$)), 2.04 (ddd, J=15.1, 5.9,4.0 Hz, 1 H, CH$_2$CH(O)CHCH$_2$), 2.00–1.94 (m, 1 H, CH$_2$CH(O)CHCH$_2$), 1.78–1.24 (m, 7 H), 1.36 (s, 3 H, C(CH$_3$)$_2$), 1.17 (d, J=7.0 Hz, 3 H, CH(CH$_3$)), 1.07 (s, 3 H, C(CH$_3$)$_2$), 1.00 (d, J=7.0 Hz, 3 H, CH(CH$_3$)); HRMS )FAB calcd. for C$_{28}$H$_{42}$FNO$_6$S (M+Cs$^+$), 672.1771 found 672.1793.

Macrolactone 67 as illustrated in Scheme 10. A solution of vinyl iodide 65 (11 mg, 0.020 mmol, 1.0 equiv.), stannane 8p (14 mg, 0.034 mmol, 1.7 equiv.) and PdCl$_2$(MeCN)$_2$ (1.0 mg, 0.004 mmol, 0.2 equiv.) in degassed DMF (250 μL, 0.08 M) is stirred at 25° C. for 20 h, according to the procedure described for the synthesis of macrolactone 18d, to yield, after preparative thin layer chromatography (250 mm silica gel plates, EtOAc) macrolactone 67 (8.5 mg, 79%). $R_f$=0.68 (silica gel, Et$_2$O); [α]$^{22}_D$ −44.7 (c 0.08 CHCl$_3$); IR (thin film) $v_{max}$ 3442, 2964, 2934, 1732, 1683, 1536, 1461, 1422, 1384, 1241, 1150, 1070, 979, 906, 732 cm$^{-}$; $^1$H NMR (500 MHz, CDCl$_3$) δ6.52 (s, 1 H, ArH), 6.36 (s, 1 H, CH=CCH$_3$), 5.41 (dd, J=7.0, 3.3 Hz, 1 H, CHOCO), 4.15 (ddd, J=10.3, 7.0, 3.7 Hz, 1 H, CHOH), 4.08 (s, 3 H, OCH$_3$), 3.99 (brd, J=6.3 Hz, 1 H, OH), 3.77 (brm, 1 H, CHOH), 3.34 (qd, J=6.6, 4.8 Hz, 1 H, CH$_3$CH(C=O)), 2.81 (dd, J=6.6, 5.9 Hz, 1 H, CH(O)CCH$_2$CH$_3$), 2.55 (dd, J=14.2, 10.1 Hz, 1 H, CH$_2$COO), 2.52 (brs, 1 H, OH), 2.39 (dd, J=14.0, 2.9 Hz, 1 H, CH$_2$COO), 2.14 (s, 3 H, CH=C(CH$_3$)), 2.05 (ddd, J=15.1, 5.5, 4.0 Hz, 1 H, CH$_2$CH(O)CHCH$_2$), 1.98–1.92 (m, 1 H, CH$_2$CH(O)CHCH$_2$), 1.80–1.70 (m, 2 H), 1.58–1.39 (m, 5 H), 1.30–1.24 (m, 2 H), 1.17 (d, J=7.0 Hz, 3 H, CH(CH$_3$)), 1.08 (s, 3 H, C(CH$_3$)$_2$), 1.00 (d, J=7.0 Hz, 3 H, CH(CH$_3$)), 0.91 (t, J=7.4 Hz, 3 H, CH$_3$CH$_2$); HRMS (FAB), calcd. for C$_{28}$H$_{43}$NO$_7$S (M+Cs$^+$), 670.1815 found 670.1837.

Macrolactone 68 as illustrated in Scheme 10. A solution of vinyl iodide 65 (5.8 mg, 0.011 mmol, 1.0 equiv.), stannane 8r (10 mg, 0.025 mmol, 2.3 equiv.) and PdCl$_2$(MeCN)$_2$ (1.0 mg, 0.004 mmol, 0.3 equiv.) in degassed DMF (100 μL, 0.1 M) is stirred at 25° C. for 23 h, according to the procedure described for the synthesis of macrolactone 18d, to yield, after preparative thin layer chromatography (250 mm silica gel plates, EtOAc) macrolactone 68 (3.7 mg, 65%). $R_f$=0.45 (silica gel, $Et_2O$); $[\alpha]^{22}_D$ −33.3 (c 0.09, $CHCl_3$); IR (thin film) $v_{max}$ 3406, 2954, 2924, 2872, 1736, 1692, 1454, 1384, 1254, 1150, 1071, 979 $cm^{-1}$; $^1H$ NMR (500 MHz, $CDCl_3$) δ6.99 (s, 1 H, ArH), 6.60 (s, 1 H, CH=$CCH_3$), 5.42 (dd, J=7.9, 3.1 Hz, 1 H, CHOCO), 4.33 (brs, 1 H, CHOH), 4.24 (brd, J=9.6 Hz, 1 H, OH), 3.76 (brm, 1 H, CHOH), 3.32 (qd, J=6.8, 4.3 Hz, 1 H, $CH_3CH(C=O)$), 3.01 (q, J=7.6 Hz, 2 H, $ArCH_2CH_3$), 2.82 (dd, J=7.4, 4.8 Hz, 1 H, $CH(O)CH_2$), 2.60 (brs, 1 H, OH), 2.54 (dd, J=13.6, 10.3 Hz, 1 H, $CH_2COO$), 2.35 (dd, J=14.0, 2.9 Hz, 1 H, $CH_2COO$), 2.10–2.05 (obscured m, 1 H, $CH_2CH(O)$), 2.09 (s, 3 H, CH=$C(CH_3)$), 1.96–1.90 (m, 1 H, $CH_2CH(O)$ $CHCH_2$), 1.80–1.67 (m, 2 H), 1.66–1.25 (m, 7 H), 1.38 (s, 3 H, $C(CH_3)_2$), 1.16 (d, J=7.0 Hz, 3 H $CH(CH_3)$), 1.07 (s, 3 H, $C(CH_3)_2$), 1.00 (d, J=7.0 Hz, 3 H $CH(CH_3)$), 0.92 (t, J=7.4 Hz, 3 H, $CH_3CH_2$), 0.91 (t, J=7.5 Hz, 3 H, $CH_3CH_2$); HRMS (FAB), calcd. for $C_{29}H_{45}NO_6S$ ($M+Cs^+$), 668.2022 found 668.2042.

Tubulin Polymerization and Cytotoxicity Assays

Tubulin polymerization is determined by the filtration-colorimetric method, developed by Bollag et Cancer Res. 1995, 55, 2325–2333. Purified tubulin (1 mg1mL) is incubated at 37° C. for 30 minutes in the presence of each compound (20 mM) in MEM buffer [(100 mM 2-(N-morpholino)ethanesulfonic acid, pH 6.75, 1 mM ethylene glycol bis(β-aminoethyl ether), N,N,N'N'-tetraacetic acid, and 1 mM $MgCl_2$]; the mixture is then filtered to remove unpolymerized tubulin by using a 96-well Millipore Multiscreen Durapore hydrophilic 0.22 μm pore size filtration plate; the collected polymerized tubulin is stained with amido black solution and quantified by measuring absorbance of the dyed solution on a Molecular Devices Microplate Reader. The growth of all cell lines is evaluated by quantitation of the protein in 96-well plates as described previously. Briefly, 500 cells are seeded in each well of the plates and incubated with the various concentrations of the epothilones at 37° C. in a humidified 5% $CO_2$ atmosphere for four days. After cell fixation with 50% trichloroacetic acid, the optical density corresponding to the quantity of proteins is measured in 25 mM NaOH solution (50% methanol:50% water) at a wavelength of 564 nm. The IC50 is defined as the dose of drug required to inhibit cell growth by 50%.

Scheme 11 is shown using conditions described in Nicolaou et al. J. Am. Chem. Soc., 1997, 119, 7974–7991 and those as indicated in the description of Scheme 11 above.

Vinyl iodide 7002 as illustrated in Scheme 11. Diiodide 7001 (1 equiv.; from 57) and sodium cyanoborohydride (10 equiv.) are dissolved in anhydrous HMPA (0.2 M) and the resulting mixture heated at 45–50° C. for 48 h. After cooling to room temperature, water is added and the aqueous phase extracted four times with ethyl acetate. The combined organic fractions are dried ($Na_2SO_4$) and passed through a short plug of silica gel to remove traces of HMPA (eluting with 50% ethyl acetate in hexanes). Following evaporation of solvents, the residue is purified by preparative thin layer chromatography (eluting with 50% ethyl acetate in hexanes) to provide pure vinyl iodide 7002 (84%).

What is claimed is:

1. A compound represented by the following structure:

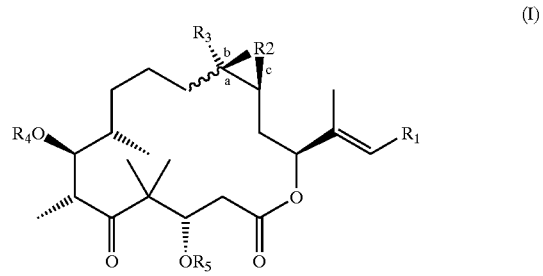

(I)

wherein the waved bond indicates that bond "a" is present either in the cis or in the trans form;

(i) $R_3$ is a radical selected from the group consisting of hydrogen; lower alkyl ($C_1$–$C_6$); —CH=$CH_2$; —C≡CH; —$CH_2F$; —$CH_2Cl$; —$CH_2$—OH; —$CH_2$—O—($C_1$–$C_6$ alkyl); and —$CH_2$—S—($C_1$–$C_6$ alkyl);

$R_4$ and $R_5$ are independently selected from the group consisting of hydrogen, methyl, and a protecting group; and $R_1$ is a radical selected from the following structures:

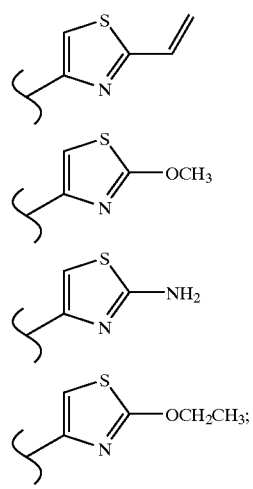

(ii) and, if $R_3$ is lower alkyl ($C_1$–$C_6$); —CH=$CH_2$; —C≡CH; —$CH_2F$; —$CH_2Cl$; —$CH_2$—OH; —$CH_2$—O—($C_1$–$C_6$ alkyl); and —$CH_2$—S—($C_1$–$C_6$ alkyl); and the other symbols except $R_1$ have the same meanings given above, $R_1$ can also be a radical selected from the following structures:

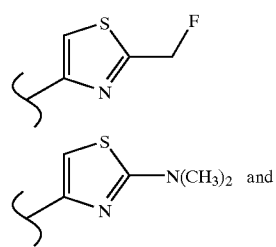

-continued

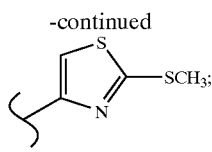

(iii) and, if $R_3$ is lower alkyl ($C_2$-$C_6$); —CH=$CH_2$; —C≡CH; —$CH_2$F; —$CH_2$Cl; —$CH_2$—OH; —$CH_2$—O—($C_1$-$C_6$ alkyl); and —$CH_2$—S—($C_1$-$C_6$ alkyl); and the other symbols except $R_1$ have the same meanings given above under (i), $R_1$ can also be a moiety of the formula

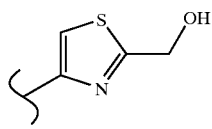

or a salt thereof where one or more salt-forming groups are present.

2. A compound of the formula I according to claim 1 wherein:
   (i) $R_3$ is a radical selected from the group consisting of hydrogen; lower alkyl ($C_1$-$C_6$); —CH=$CH_2$; —C≡CH; —$CH_2$F; —$CH_2$Cl; —$CH_2$—OH; —$CH_2$—O—($C_1$-$C_6$ alkyl); and —$CH_2$—S—($C_1$-$C_6$ alkyl);
   $R_4$ and $R_5$ are independently selected from the group consisting of hydrogen, methyl, and a protecting group; and
   $R_1$ is a radical selected from the following structures:

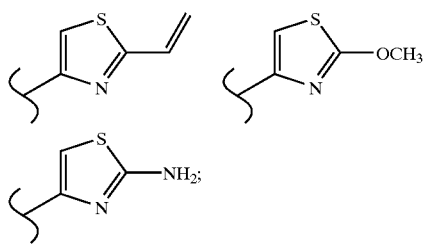

or a salt thereof where one or more salt-forming groups are present.

3. A compound of the formula I according to claim 1 wherein:
   (i) $R_3$ is a radical selected from the group consisting of hydrogen; lower alkyl ($C_1$-$C_6$); —CH=$CH_2$; —C≡CH; —$CH_2$F; —$CH_2$Cl; —$CH_2$—OH; —$CH_2$—O—($C_1$-$C_6$ alkyl); and —$CH_2$—S—($C_1$-$C_6$ alkyl);
   $R_4$ and $R_5$ are independently selected from the group consisting of hydrogen, methyl, and a protecting group; and
   $R_1$ is a radical selected from the following structure:

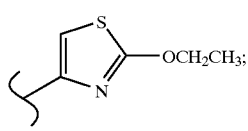

or a salt thereof where one or more salt-forming groups are present.

4. A compound of the formula I according to claim 1 wherein:
   (i) $R_3$ is a lower alkyl ($C_1$-$C_6$); —CH=$CH_2$; —C≡CH; —$CH_2$F; —$CH_2$Cl; —$CH_2$—OH; —$CH_2$—O—($C_1$-$C_6$ alkyl); and —$CH_2$—S—($C_1$-$C_6$ alkyl);
   $R_4$ and $R_5$ are independently selected from the group consisting of hydrogen, methyl, and a protecting group; and
   $R_1$ is a radical selected from the following structure:

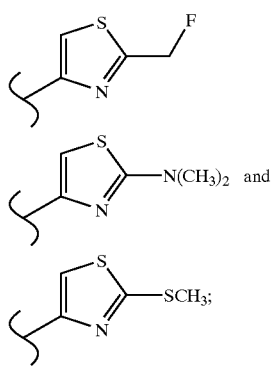

or a salt thereof where one or more salt-forming groups are present.

5. A compound of the formula I according to claim 1 wherein:
   (i) $R_3$ is a lower alkyl ($C_2$-$C_6$); —CH=$CH_2$; —C≡CH; —$CH_2$F; —$CH_2$Cl; —$CH_2$—OH; —$CH_2$—O—($C_1$-$C_6$ alkyl); and —$CH_2$—S—($C_1$-$C_6$ alkyl);
   $R_4$ and $R_5$ are independently selected from the group consisting of hydrogen, methyl, and a protecting group; and
   $R_1$ is a radical of the formula

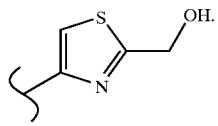

6. A compound of the formula Id

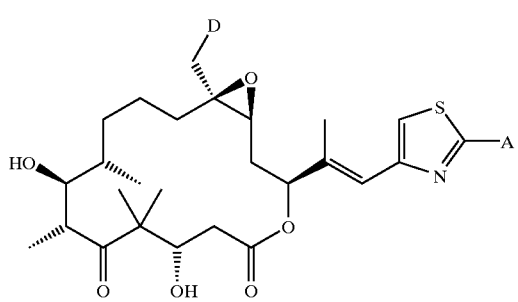

(Id)

wherein A is fluoromethyl, methoxy, methylthio or ethenyl (—CH=$CH_2$) and D is hydrogen, fluoro, hydroxy or methyl.

7. A compound according to claim 1, selected from the group consisting of a compound of the following formulae:

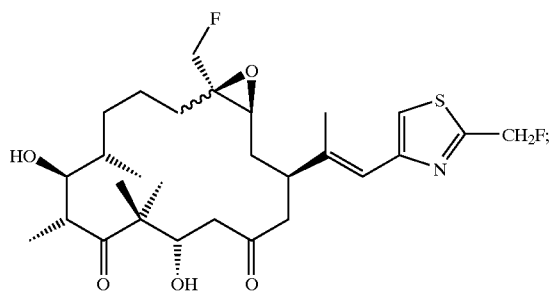
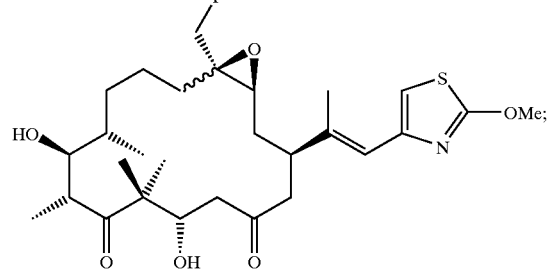
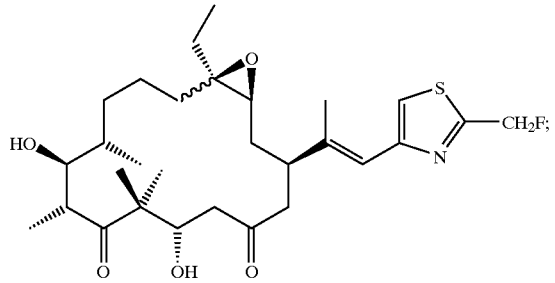
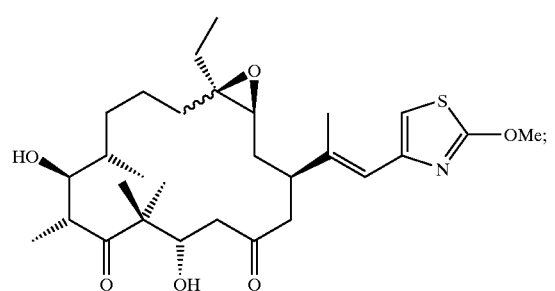
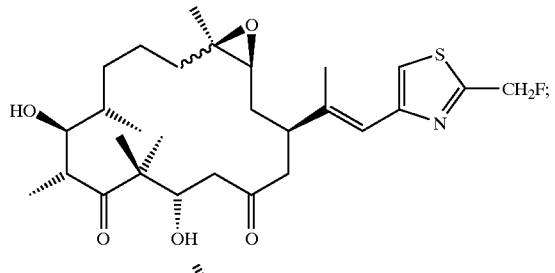
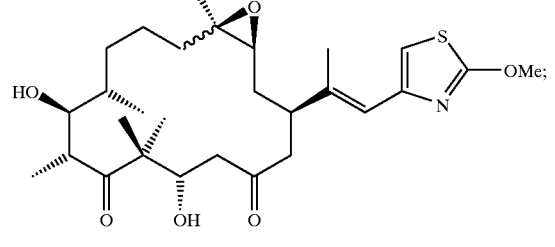
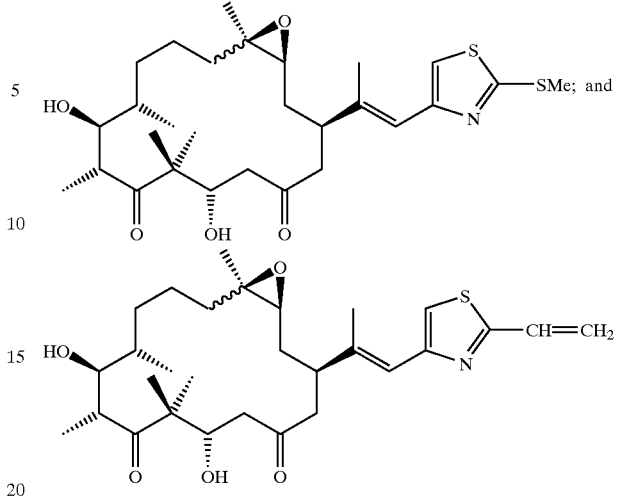

or a salt thereof where one or more salt-forming groups are present.

8. A pharmaceutical composition comprising a compound according to any one of claims 1–4, 5, and 6 and a pharmaceutically acceptable carrier.

9. A method of treatment of a warm-blooded animal suffering a proliferative disease and that is in need of such treatment, comprising administering a compound of the formula I, or a pharmaceutically acceptable salt thereof, according to claim 1 to said warm-blooded animal in an amount that is sufficient for said treatment, said proliferative disease being selected from the group consisting of lung cancer, prostate cancer, cancer of the intestine, epidermoid tumor, breast cancer, bladder cancer, pancreas cancer, brain cancer, and melanoma.

10. A method for the synthesis of a compound of the formula I, in claim 1, comprising a) coupling a iodide of the formula II,

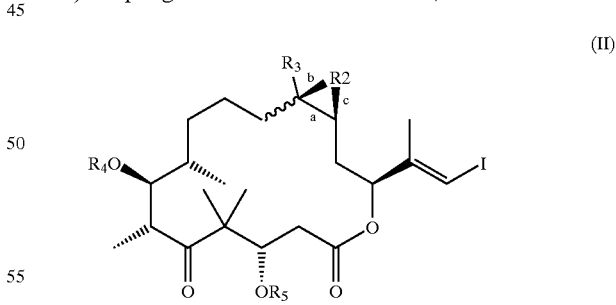

wherein $R_2$, $R_3$, $R_4$, $R_5$, a, b and c and the waved bond have the meanings given under formula I in claim 1, with a tin compound of the formula III,

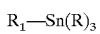

wherein $R_1$ has the meanings given under formula I and R is lower alkyl, especially methyl or n-butyl, or b) coupling a tin compound of the formula IV,

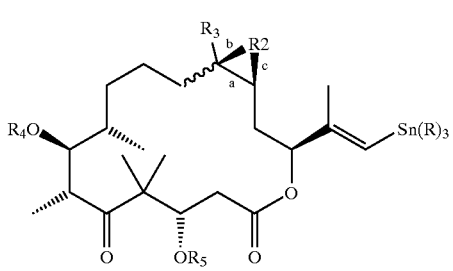

(IV)

wherein $R_2$, $R_3$, $R_4$, $R_5$, a, b and c and the waved bond have the meanings given under formula I, with a iodide of the formula V,

(V)

wherein $R_1$ has the meanings given under formula I in claim 1;

and, if desired, a resulting compound of the formula I is converted into a different compound of the formula I, a resulting free compound of the formula I is converted into a salt of a compound of the formula I, and/or a resulting salt of a compound of the formula I is converted into a free compound of the formula I or into a different salt of a compound of the formula I, and/or a stereoisomeric mixture of compounds of formula I is separated into the corresponding isomers.

11. A method for synthesizing an epothilone E or F of the formula IX,

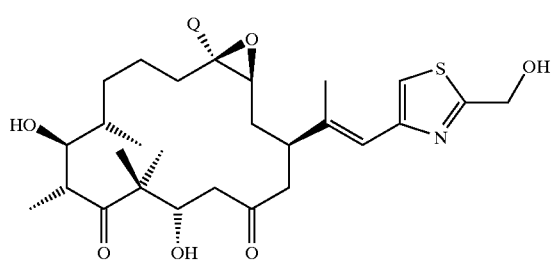

(IX)

wherein Q is Hydrogen or methyl, the method comprising the following step:

epoxidizing a compound of the formula X to the compound of the formula IX in the presence of an epoxide, the compound of the formula X being represented as follows,

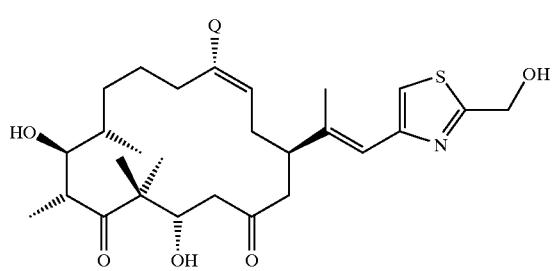

(X)

wherein Q is hydrogen or methyl.

12. A compound represented by the following structure:

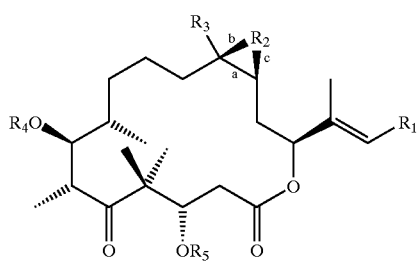

wherein the waved bond indicates that bond "a" is present either in the cis or in the trans form; and $R_2$ is absent or oxygen; "a" can be either a single or double bond; "b" can be either absent or a single bond; and "c" can be either absent or a single bond, with the proviso that if $R_2$ is oxygen then "b" and "c" are both a single bond and "a" is a single bond; if $R_2$ is absent then "b" and "c" are absent and "a" is a double bond; and if "a" is a double bond, then $R_2$, "b" and "c" are absent;

$R_3$ is a radical selected from the group consisting of lower alkyl $(C_1-C_6)$; —CH=$CH_2$; —C≡CH; —$CH_2$F; —$CH_2$Cl; —$CH_2$—OH; —$CH_2$—O—$(C_1-C_6$ alkyl); and —$CH_2$—S—$(C_1-C_6$ alkyl);

$R_4$ and $R_5$ are independently selected from the group consisting of hydrogen, methyl, and a protecting group; and $R_1$ is a radical selected from the following structures:

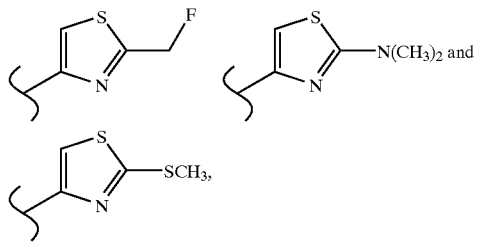

or a salt thereof where one or more salt-forming groups are present.

13. A compound according to claim 12 represented by the following structure:

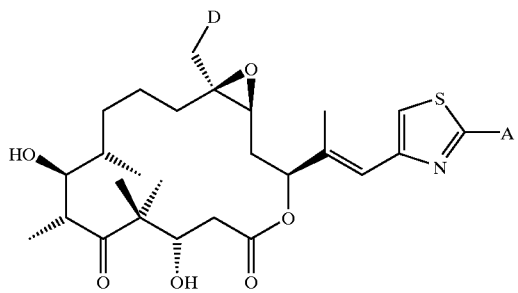

wherein

A is a radical selected from the group consisting of fluoromethyl, and methylthio; and D is a radical selected from the group consisting of hydrogen, fluoro, hydroxy, and methyl.

14. A compound according to claim 13 represented by the following structure:

15. A compound represented by the following structure:

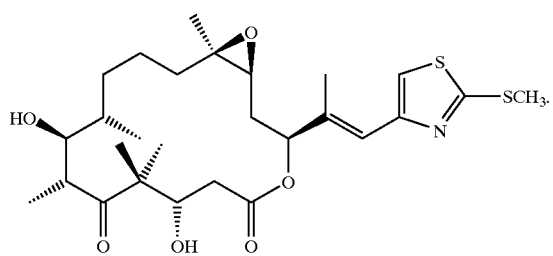

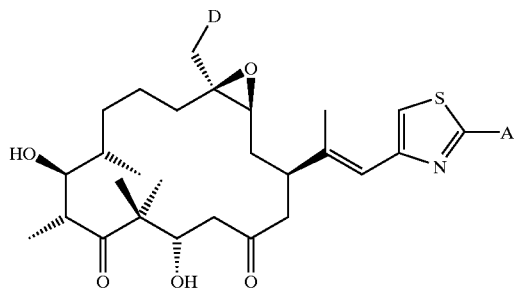

wherein

A is radical selected from the group consisting of fluoromethyl, methoxy, methylthio, and ethenyl (—CH=CH$_2$); and D is a radical selected from the group consisting of hydrogen, fluoro, hydroxy, and methyl; or a salt thereof where one or more salt-forming groups are present.

16. A compound according to claim 15 represented by the following structure:

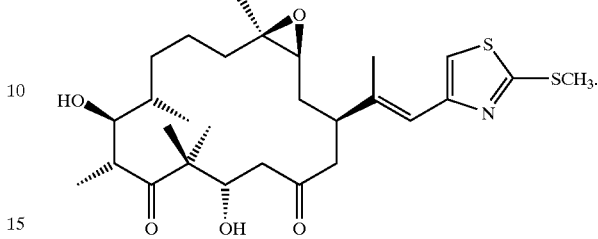

17. A compound represented by the following structure:

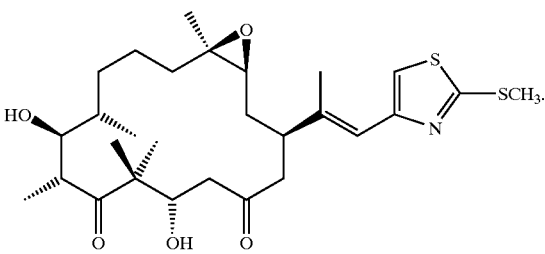

* * * * *

UNITED STATES PATENT AND TRADEMARK OFFICE
CERTIFICATE OF CORRECTION

PATENT NO. : 6,531,497 B1
APPLICATION NO. : 09/720070
DATED : March 11, 2003
INVENTOR(S) : Kyriacos Costa Nicolaou et al.

It is certified that error appears in the above-identified patent and that said Letters Patent is hereby corrected as shown below:

In column 85 Line 1-65 of the patent, formula of Claim 7 should read as follows:

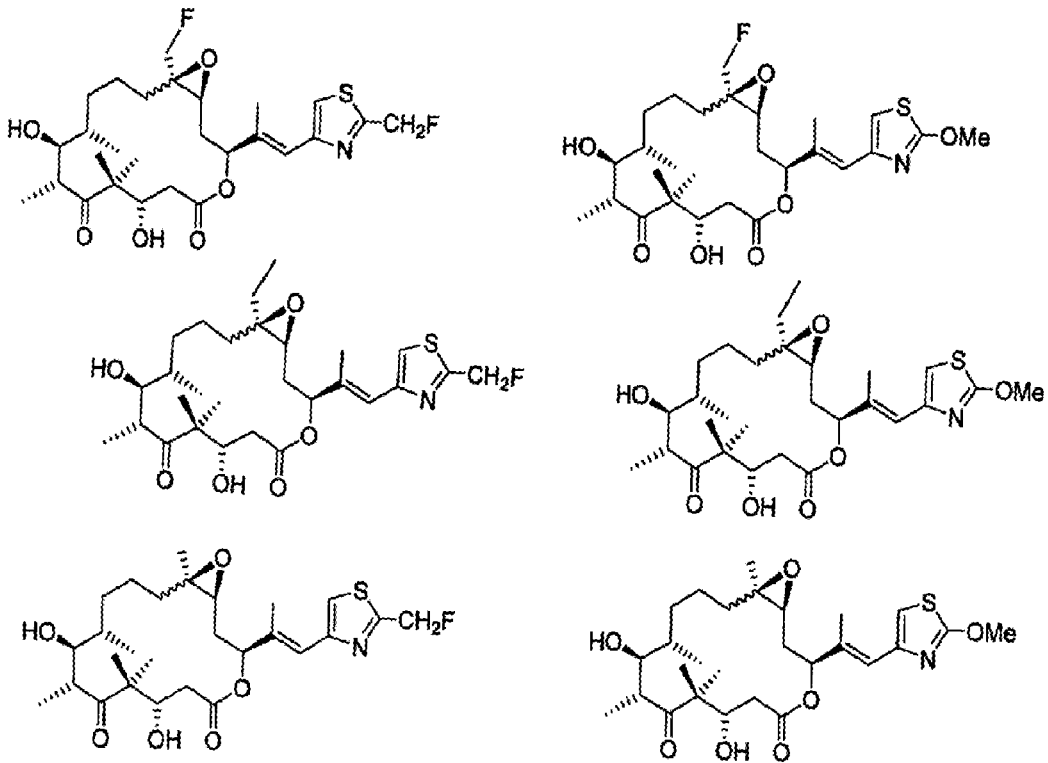

UNITED STATES PATENT AND TRADEMARK OFFICE
CERTIFICATE OF CORRECTION

PATENT NO.         : 6,531,497 B1
APPLICATION NO. : 09/720070
DATED                 : March 11, 2003
INVENTOR(S)       : Kyriacos Costa Nicolaou et al.

It is certified that error appears in the above-identified patent and that said Letters Patent is hereby corrected as shown below:

In column 86 Line 1-20 of the patent, formula of Claim 7 should read as follows:

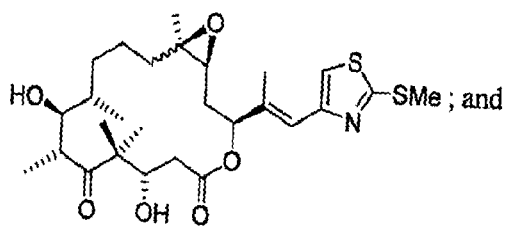 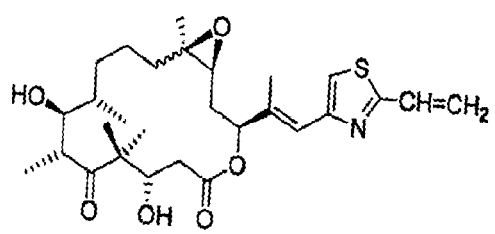

UNITED STATES PATENT AND TRADEMARK OFFICE
CERTIFICATE OF CORRECTION

PATENT NO. : 6,531,497 B1  
APPLICATION NO. : 09/720070  
DATED : March 11, 2003  
INVENTOR(S) : Kyriacos Costa Nicolaou et al.

Page 3 of 5

It is certified that error appears in the above-identified patent and that said Letters Patent is hereby corrected as shown below:

In column 87 Line 35-45 and Line 55-65 of the patent, formula of Claim 11 should read as follows:

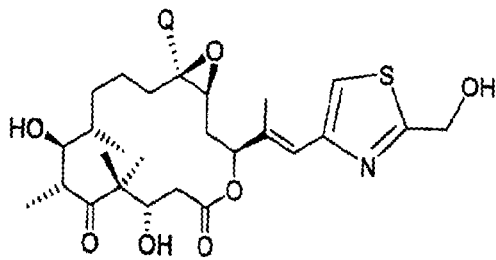 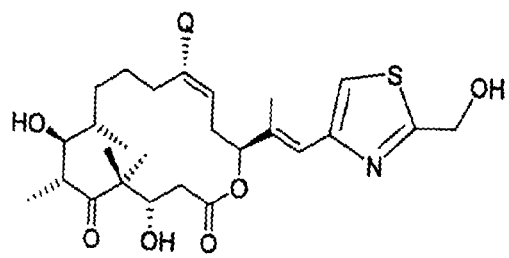

UNITED STATES PATENT AND TRADEMARK OFFICE
CERTIFICATE OF CORRECTION

PATENT NO.        : 6,531,497 B1                                    Page 4 of 5
APPLICATION NO. : 09/720070
DATED              : March 11, 2003
INVENTOR(S)       : Kyriacos Costa Nicolaou et al.

It is certified that error appears in the above-identified patent and that said Letters Patent is hereby corrected as shown below:

In column 89 Line 15-25 of the patent, the formula of Claim 15 should read as follows:

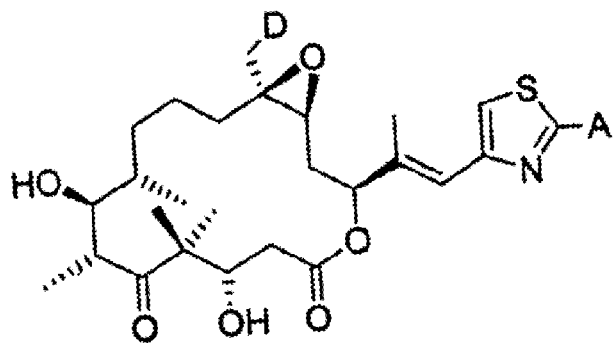

UNITED STATES PATENT AND TRADEMARK OFFICE
CERTIFICATE OF CORRECTION

PATENT NO. : 6,531,497 B1
APPLICATION NO. : 09/720070
DATED : March 11, 2003
INVENTOR(S) : Kyriacos Costa Nicolaou et al.

It is certified that error appears in the above-identified patent and that said Letters Patent is hereby corrected as shown below:

In column 90 Line 6-16 of the patent, the formula of Claim 16 should read as follows:

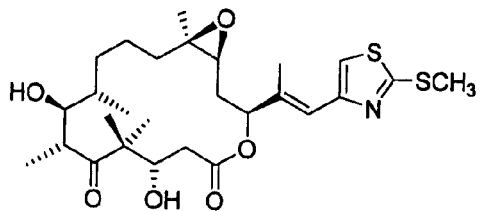

In column 90 Line 20-30 of the patent, the formula of Claim 17 should read as follows:

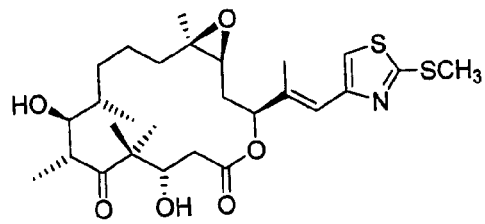

Signed and Sealed this

Twentieth Day of January, 2009

JON W. DUDAS
*Director of the United States Patent and Trademark Office*